United States Patent [19]

Dürckheimer et al.

[11] 4,399,131

[45] Aug. 16, 1983

[54] CEPHEM DERIVATIVES

[75] Inventors: Walter Dürckheimer, Hattersheim am Main; Eberhard Ehlers, Hofheim am Taunus; Hubert Seliger, Frankfurt am Main; Elmar Schrinner, Wiesbaden, all of Fed. Rep. of Germany

[73] Assignee: Hoechst AG, Frankfurt am Main, Fed. Rep. of Germany

[21] Appl. No.: 146,780

[22] Filed: May 5, 1980

Related U.S. Application Data

[63] Continuation of Ser. No. 896,156, Apr. 13, 1978, abandoned.

[30] Foreign Application Priority Data

Apr. 15, 1977 [DE] Fed. Rep. of Germany ....... 2716677

[51] Int. Cl.³ .................. A61K 31/545; C07D 501/34
[52] U.S. Cl. ...................................... 424/246; 544/21;
544/22; 544/23; 544/25; 544/27; 544/28
[58] Field of Search ....................... 544/28, 21, 22, 23,
544/25, 27; 424/246

[56] References Cited

U.S. PATENT DOCUMENTS

| | | | |
|---|---|---|---|
| 3,926,957 | 12/1975 | Gregson et al. ................. | 260/239.1 |
| 3,932,385 | 1/1976 | Cook et al. ..................... | 260/239.1 |
| 3,971,778 | 7/1976 | Cook et al. .......................... | 424/246 |
| 4,020,058 | 4/1977 | Cocker et al. ...................... | 424/246 |
| 4,075,337 | 2/1978 | Marx et al. .......................... | 424/246 |
| 4,092,474 | 5/1978 | Yoshioka et al. ..................... | 544/17 |
| 4,098,888 | 7/1978 | Ochiai et al. ........................ | 424/246 |
| 4,152,432 | 5/1979 | Heymes et al. ........................ | 544/28 |
| 4,166,115 | 8/1979 | Takaya et al. ........................ | 544/30 |
| 4,203,899 | 5/1980 | Ochiai et al. ........................ | 544/27 |
| 4,237,128 | 12/1980 | Cimarusti et al. .................... | 544/28 |
| 4,252,802 | 2/1981 | Denzel et al. ........................ | 544/28 |
| 4,254,260 | 3/1981 | Takaya et al. ........................ | 544/27 |

FOREIGN PATENT DOCUMENTS

| | | |
|---|---|---|
| 2204060 | 8/1972 | Fed. Rep. of Germany . |
| 2223375 | 11/1972 | Fed. Rep. of Germany . |
| 2625015 | 12/1976 | Fed. Rep. of Germany . |
| 2137899 | 12/1972 | France . |
| 2192805 | 2/1974 | France . |
| 78703 | 5/1982 | Rep. of Korea . |

OTHER PUBLICATIONS

Flynn, "Cephalosporins and Penicillins," pp. 562-563, (1972).
J. J. de Koning, Rec. Adv. Chem. Beta-Lactam-Antib., Cambridge, Eng., 28.30.6.1976, ed. by J. Elks, The Chem. Soc., Burlington House, London, 1977, pp. 161-166.
Schroeder et al., "The Peptides", vol. I, Academic Press, New York, 1965, pp. xxiii-xxvi.
Gregory (Editor), "Recent Advances in the Chemistry of Beta-Lactam Antibiotics", Special Publn. No. 38, Royal Society of Chemistry, London, Proc. 2nd Intl. Symposium 6/30-7/20/80, pp. 46-56.

Primary Examiner—Paul M. Coughlan, Jr.
Attorney, Agent, or Firm—Curtis, Morris & Safford

[57] ABSTRACT

What are disclosed are cephem compounds of the formula

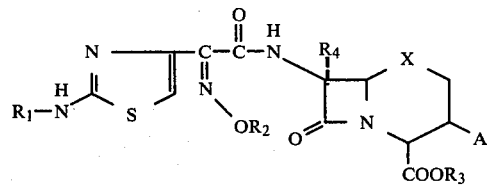

in which $R_1$ denotes hydrogen, an optionally substituted alkyl, acyl, arylsulfonyl or alkylsulfonyl group or an amino-protective group which is known from peptide chemistry, $R_2$ denotes hydrogen or an optionally substituted alkyl, alkenyl, alkinyl, cycloalkyl, aralkyl, acyl, aryl, arylsulfonyl, alkylsulfonyl or heterocyclic group, $R_3$ denotes hydrogen, an ester group or a cation, $R_4$ denotes hydrogen, a lower alkoxy group or a group which can be converted to this, X denotes a SO group in the R or S configuration or a $SO_2$ group and A denotes hydrogen, an optionally substituted alkoxy or alkenyloxy group, halogen or a group $—CH_2Y$, in which Y represents hydrogen, halogen or the radical of a nucleophilic compound, and in which the $R_2O$ group is in the syn-position, which compounds are valuable chemotherapeutic agents having a very powerful antimicrobial action against Gram-positive and Gram-negative bacteria and an unexpectedly good action against penicillinase-forming Staphilococci.

9 Claims, No Drawings

CEPHEM DERIVATIVES

This is a continuation, of application Ser. No. 896,156, filed Apr. 13, 1978, now abandoned.

The invention relates to cephem derivatives of the general formula I

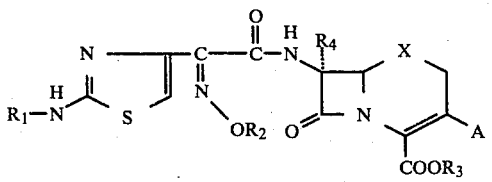

in which $R_1$ denotes hydrogen, an optionally substituted alkyl, acyl, arylsulfonyl or alkylsulfonyl group or an aminoprotective group which is known from peptide chemistry, $R_2$ denotes hydrogen or an optionally substituted alkyl, alkenyl, alkinyl, cycloalkyl, aralkyl, acyl, aryl, arylsulfonyl, alkylsulfonyl or heterocyclic group, $R_3$ denotes hydrogen, an ester group or a cation, $R_4$ denotes hydrogen, a lower alkoxy group or a group which can be converted to this, X denotes a SO group in the R or S configuration or a $SO_2$ group and A denotes hydrogen, an optionally substituted alkoxy or alkenyloxy group, halogen or a group —$CH_2Y$, in which Y represents hydrogen, halogen or the radical of a nucleophilic compound, and in which the $R_2O$ group is in the syn-position.

The invention furthermore relates to a process for the manufacture of cephem derivatives of the general formula I, which comprises (a) reacting lactams of the general formula II

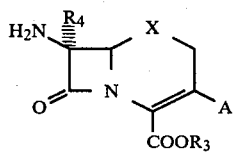

wherein A, X, $R^3$ and $R^4$ have the meanings indicated above, but $R^3$ cannot represent hydrogen, with reactive derivatives of a carboxylic acid of the general formula III

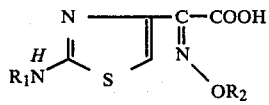

in which the radicals $R^1$ and $R^2$ have the meanings indicated above, but $R^1$ cannot be hydrogen, or (b) oxidising cephem compounds of the general formula IV

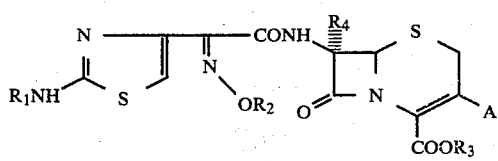

in which the radicals $R_1$, $R_2$, $R_3$, $R_4$ and A have the meanings indicated above, on the sulfur of the cephem ring and, if desired, in the compounds manufactured according to (a) or (b)

($\alpha$) converting a resulting salt into the free carboxylic acid and optionally further esterifying this, or converting a resulting salt directly into an ester, ($\beta$) saponifying a resulting ester and optionally converting the resulting product into a salt, ($\gamma$) splitting off a radical $R_1$, if this denotes a protective group, and ($\delta$) if $R_4$ represents a group which can be converted into a lower alkoxy group, carrying out this conversion, it being possible for one or more of the reactions given under ($\alpha$) to ($\delta$) to be used.

The present invention relates to compounds of the general formula I in which the substituents can have, for example, the following meaning.

$R_1$ can represent hydrogen, optionally substituted alkyl with 1-6 carbon atoms, preferably tert.-butyl, tert.-amyl, benzyl, p-methoxybenzyl, benzhydryl, trityl and phenylethyl, benzyl, benzhydryl and trityl also being amino-protective groups which are known from peptide chemistry, aliphatic acyl with 1-6, preferably 1-4, C atoms, such as, for example, formyl, acetyl or butyryl, it also being possible for such an acyl group to be further monosubstituted or polysubstituted, for example by halogen, such as, for example, fluorine, chlorine or bromine, which can also lead, for example, to the chloroacetyl or trichloroacetyl radicals, which are known from peptide chemistry as amino-protective groups, by aryl, in particular phenyl, which can also carry still further substituents, such as, for example, a heterocyclic radical defined under $R_5$; alkyl with 1-4 C atoms, preferably methyl; alkenyl with 1-4 C atoms, preferably allyl; alkoxy with 1-4 C atoms, preferably methoxy; alkylthio with 1-4 C atoms, preferably methylthio; halogen, preferably chlorine or bromine; sulfamoyl, carbamoyl, carboxyl or trifluoromethyl; alkoxycarbonyl with 1-4 alkyl C atoms, such as, for example, methoxycarbonyl; cyano or nitro; amino; alkylamino with 1-4 C atoms, such as, for example, methylamino or ethylamino; dialkylamino with 1-4 C atoms, such as, for example, dimethyl- or diethyl-amino, or amidino, by a nucleophilic radical, defined under Y, preferably —$SR_5$, by aryloxy, in particular phenoxy, by arylmercapto, in particular phenylmercapto or by arylamino, in particular phenylamino, it also being possible for these aryloxy, arylmercapto and arylamino radicals, for example, to carry the substituents indicated above for aryl (as a substituent of the aliphatic acyl $R_1$), by an optionally substituted hetero-aromatic 5-membered or 6-membered ring with 1 to 4 hetero-atoms, in particular nitrogen, sulfur or oxygen, such as is described in detail under —$SR_5$, by hydroxyl, by alkoxy with 1-4 C atoms, in particular methoxy or ethoxy, by alkylthio with 1-4 C atoms, in particular methylthio or ethylthio, by alkylamino with 1-4 C atoms, in particular methylamino or ethylamino, or by dialkylamino with 1-4 C atoms, in particular dimethyl- or diethyl-amino, which can be closed to form a 5-membered to 7-membered ring which can be optionally interrupted by hetero-atoms, such as, for example, oxygen or nitrogen, such as, for example, morpholine, piperazine or N-alkyl-piperazine in which alkyl has 1-4 C atoms, preferably N-methylpiperazine, aromatic acyl, preferably benzoyl, it also being possible for the aromatic group to be substituted, such as is indicated above for the aryl substituents of the aliphatic acyl radical $R_1$, hetero-aromatic acyl, the hetero-aromatic 5-membered or 6-membered ring with 1 to 4 hetero-atoms, which can also be further substituted, as described above for aryl, being one such as is described in detail under —SR$_5$, optionally substituted alkylsulfonyl with 1-4 C atoms, in particular methylsulfonyl or ethylsulfonyl, arylsulfonyl, preferably phenylsulfonly, which can be substituted in the manner indicated above for aryl, in particular by nitro, amino or alkyl with 1-4 C atoms, such as, for example, methyl, or an amino-protective group which is known from peptide chemistry (compare, for example, Houben-Weyl, volume XV/1, page 46 (1974)), in particular alkoxycarbonyl with 1-4 alkyl C atoms, which is preferably substituted by halogen or cyano, such as, for example, methoxycarbonyl, tert.-butoxycarbonyl, trichloroethoxycarbonyl or cyano-tert.-butoxycarbonyl, or arylalkoxycarbonyl with 1-4 alkyl C atoms, in particular phenylalkoxycarbonyl, it also being possible for the aryl radical to be further substituted, for example by nitro or lower alkoxy, preferably benzyloxycarbonyl, p-nitro- or p-methoxy-benzyloxycarbonyl, 3,5-dimethoxybenzyloxycarbonyl or 2-biphenylyl-4-isopropoxycarbonyl, or trialkylsilyl, in which alkyl can consist of 1-4 C atoms, such as, for example, trimethylsilyl or tert.-butyldimethylsilyl.

$R_2$ can denote, for example, hydrogen, alkyl with 1-4 C atoms, such as, for example, methyl, ethyl, propyl or butyl, preferably methyl, or cycloalkyl with 3-8, preferably 3-6, C atoms, such as, for example, cyclopropyl, cyclobutyl, cyclopentyl or cyclohexyl, it also being possible for alkyl and cycloalkyl to be further monosubstituted or polysubstituted, for example by alkyl with 1-4 C atoms, preferably methyl, by cycloalkyl with 3-8, in particular 3-6, C atoms, such as, for example, cyclopentyl or cyclohexyl, by alkoxycarbonyl with 1-4 alkyl C atoms, preferably methoxycarbonyl or ethoxycarbonyl, by carboxyl; cyano; carbamoyl, which can be mono-substituted or disubstituted by optionally substituted, for example hydroxy-substituted, alkyl with 1-4 C atoms, it also being possible for 2 substituents to be closed to form a 5-membered or 6-membered ring which is optionally interrupted by O or N, such as, for example, morpholino, piperazino, N-methylpiperazino or pyrrolidino, by alkylcarbonyl with 1-4 alkyl C atoms, in particular acetyl, by sulfo or sulfamoyl, by alkoxysulfonyl with 1-C atoms, in particular methoxy- or ethoxy-sulfonyl, by a phosphono group, by hydroxyl, by halogen, preferably chlorine or bromine, by alkoxy with 1-4 C atoms, in particular methoxy or ethoxy, by alkylthio with 1-4 C atoms, in particular methylthio or ethylthio, by acyloxy, in particular aliphatic acyloxy with 1-4 C atoms, such as, for example, acetoxy or benzoyloxy, by carboxyalkoxy with 1-4 alkyl C atoms, in particular carboxymethoxy, or by aryl, preferably phenyl, which can also carry substituents, such as are indicated for the aryl radical substituting the aliphatic acyl ($R_1$), alkenyl with 2-6, preferably 3-5, C atoms, such as, for example, allyl or crotonyl, which can also be further substituted, for example by alkyl with 1-4 C atoms, preferably methyl, by halogen, in particular chlorine or bromine, by carboxyl or carbamoyl, which can be substituted, as indicated above under alkyl ($R_2$), or by alkoxycarbonyl with 1-4 alkyl C atoms, in particular methoxycarbonyl or ethoxycarbonyl, alkinyl with 3-5 C atoms, preferably propargyl, which can also be further substituted, for example by aryl, preferably phenyl, aliphatic, saturated or unsaturated acyl with 1-7, preferably 1-4, C atoms, such as, for example, formyl, acetyl, propionyl, butyryl, hexanoyl, acryloyl, crotonoyl or propioloyl, which can also be further substituted, for example by halogen, such as, for example, chlorine, bromine or fluorine, which leads, for example, to a chloroacetyl, dichloroacetyl or bromoacetyl radical, by amino, by alkylamino with 1-4 C atoms, preferably methyl- or ethyl-amino, or by dialkylamino with 1-4 C atoms, in particular dimethyl- or diethyl-amino, which can also be closed to form a ring which is optionally interrupted by hetero-atoms, such as oxygen, nitrogen or sulfur, such as, for example, morpholine, piperazine or perhydrothiazine, aromatic acyl, such as, for example, benzoyl or naphthoyl, which can also be substituted, for example by alkyl with 1-4 C atoms, in particular methyl, by halogen, preferably chlorine or bromine, by alkoxy with 1-4 C atoms, in particular methoxy, by dialkylamino with 1-4 C atoms, in particular dimethyl- or diethylamino, which can also be closed to form a ring which is optionally interrupted by hetero-atoms, such as, for example, oxygen or nitrogen and which has already been described above, or by trifluoromethyl, heterocyclic acyl, which is derived from heterocyclic 5-membered or 6-membered rings with 1 to 4 hetero-atoms, such as, for example, sulfur, oxygen and nitrogen, such as, for example, thenoyl, furoyl, nicotinoyl, isonicotinoyl or picolinoyl, and which can also be further substituted, for example by substituents such as are indicated above for aromatic acyl ($R_2$), optionally substituted arylsulfonyl, in particular phenylsulfonyl, p-tolylsulfonyl and p-amino-phenylsulfonyl, optionally substituted alkylsulfonyl with 1-7, preferably 1-4, C atoms, in particular methyl- or ethyl-sulfonyl, aryl, preferably phenyl, or, for example, 1- or 2-naphthyl, which can also be further substituted, for example by substituents such as are indicated above for aromatic acyl ($R_2$), or a heterocyclic group, which is derived from a heterocyclic 5-membered or 6-membered ring with 1-4 hetero-atoms, such as, for example, sulfur, oxygen and nitrogen, such as, for example, thienyl, furyl, pyridyl or picolinyl, and can also be further substituted, for example by substituents such as are indicated above for aromatic acyl ($R_2$).

$R_3$ can represent, for example, hydrogen, an ester group or a cation.

If $R_3$ denotes an ester group, possible examples of this are straight-chain or branched alkyl with 1 to 12, preferably 1 to 6, C atoms, such as, for example, methyl, ethyl, i-propyl, tert.-butyl, hexyl as well as, for example, octyl or dodecyl, straight-chain or branched alkenyl with 2 to 12, preferably 3 to 5, C atoms, such as, for example, allyl, crotyl, pentenyl as well as dodecenyl, or straight-chain or branched alkinyl with 3-12, preferably 3-5, C atoms, such as, for example, propinyl, butinyl, pentinyl as well as dodecinyl, it also being possible for these alkyl, alkenyl or alkinyl groups to be monosubstituted or polysubstituted by identical or different substituents, for example by halogen, in particular chlorine or bromine, whereby, for example, a trichloromethyl radical results, by hydroxyl, by alkoxy with 1 to 4 C atoms, in particular methoxy or ethoxy, once or twice, preferably twice, by carbocyclic or heterocyclic aryl, such as, in particular, phenyl, or radicals which are derived from hetero-aromatic 5-membered or 6-membered rings with 1 to 4 hetero-atoms, such as, for example, sulfur, oxygen and nitrogen, such as, for example, thienyl, furyl or pyridyl, which can also carry still further substituents, for example those which have been given above in detail for the aryl substituent of the aliphatic acyl group ($R_1$), by carbocyclic or heterocyclic aryloxy, such as, in particular, phenoxy, or radicals which are derived from hetero-aromatic 5-membered or 6-membered rings with 1 to 4 hetero-atoms, such as, for example, sulfur, oxygen and nitrogen, such as, for example, pyridinoxy, which can also carry further substituents, such as have been indicated above, for example, for the aryl substituent of the alkyl radical $R_3$, by carboxyl or cyano, by carbamoyl, which can also be substituted, for example by one or two alkyl groups with 1–4 C atoms, preferably methyl; or lower aralkyl, preferably benzyl, by alkoxycarbonyl with 1–4 alkyl C atoms, such as, for example, methoxycarbonyl, by alkylcarbonyloxy with 1–6, preferably 1–4, alkyl C atoms, such as acetoxy, pivaloyloxy or also hexanoyloxy, by cycloalkylcarbonyloxy with 3–7 cycloalkyl C atoms, such as, for example, cyclohexylcarbonyloxy, by aroyloxy, such as, for example, benzoyloxy, by carbocyclic or heterocyclic arylalkylcarbonyl with 1–4 alkyl C atoms, such as, for example, phenylacetyl or thienylacetyl, by carbocyclic or heterocyclic aryloxyalkylcarbonyl with 1–4 alkyl C atoms, such as for example phenoxyacetyl or thienyloxy acetyl, by alkylcarbonyl with 1–6, preferably 1–4, alkyl C atoms, such as, for example, acetyl, propionyl or butyryl, which can also be monosubstituted or polysubstituted, for example by oxyimino; alkoxyimino, as defined in more detail under $R_2$, in particular methoxyimino; or alkoxycarbonyl with 1–4 alkyl C atoms, in particular methoxy- or ethoxycarbonyl; by carbocyclic or heterocyclic arylcarbonyl, such as, for example, benzoyl or thenoyl, which can also carry further substituents, such as, for example, alkyl with 1–4 C atoms, such as, preferably, methyl or ethyl; alkoxy with 1–4 C atoms, preferably methoxy or ethoxy; halogen, preferably chlorine or bromine; sulfamoyl; trifluoromethyl; alkylamino with 1–4 C atoms, such as methyl- or ethyl-amino; or dialkylamino with 1–4 C atoms, such as dimethyl- or diethyl-amino, which can also be closed to form a 5-membered to 7-membered ring which is optionally interrupted by hetero-atoms, such as, for example, oxygen, nitrogen or sulfur, such as, for example, morpholine or piperazine, or by optionally substituted aryl, preferably phenyl, trialkylsily with 1–4 C atoms in the alkyl group, such as, for example, trimethylsilyl, or indanyl or phthalidyl.

If $R_3$ denotes a cation, it represents an inorganic metal ion or an organic ammonium ion. Examples which may be mentioned are, in particular, pharmacologically acceptable alkali metal ions or alkaline earth metal ions, preferably the sodium, potassium, calcium or magnesium ion, the ammonium ion and, from the organic ammonium ions, in particular, an optionally substituted, alkylated ammonium ion, such as, for example, the triethylammonium or diethanolammonium ion, as well as the morpholineammonium, benzylammonium, procaineammonium, L-arginineammonium and L-lysineammonium ion.

$R_4$ can represent, for example, hydrogen, lower alkoxy with 1–4 C atoms, preferably methoxy, or a group which can be converted into such an alkoxy group, such as, for example, halogen, preferably bromine, or saturated or unsaturated alkylthio with 1–4 C atoms, such as, for example, methylthio, ethylthio, i-propylthio or allylthio.

A can denote, for example, hydrogen, alkoxy with 1–4 C atoms, such as methoxy, ethoxy or butoxy, in particular methoxy, it also being possible for the alkyl chain, with the exception of that having 2 C atoms, to be substituted, for example by hydroxyl or by halogen, preferably chlorine or bromine, alkoxycarbonyl with 1–4 alkyl C atoms, in particular methoxy- or ethoxycarbonyl, alkenyloxy with 3–6 C atoms, such as, for example, allyloxy, which can be substituted in the same manner as the alkoxy group (A) above, halogen, preferably chlorine or bromine, or —CH$_2$Y, wherein Y, in addition to hydrogen or halogen, such as, for example, fluorine, chlorine or bromine, can also represent the radical of a nucleophilic compound.

Examples which may be mentioned of such radicals of a nucleophilic compound, preferably of a S-, N- or O-nucleophilic compound, are acyloxy, hydroxyl, alkoxy, amino, alkyl- or dialkyl-amino, mercapto, optionally substituted pyridinium, quinolinium or isoquinolinium, optionally substituted carbamoyloxy or carbamoylthio, azido or a group —SR$_5$, wherein R$_5$ denotes an optionally substituted acyl, alkyl or aryl radical or an optionally substituted 5-membered or 6-membered heterocyclic ring which is optionally fused to an aromatic 5-membered or 6-membered ring, or the radical

in which Z represents sulfur or oxygen and $R_6$ and $R_7$, which can be identical or different, represent alkyl, alkenyl, alkoxy, alkenyloxy, optionally substituted phenyl or a carbocyclic ring with 3–8 C atoms.

Some of the groups which are possible, according to the invention, as the nucleophilic radical Y are illustrated in more detail in the following text.

If Y represents acyloxy, possible acyl radicals are, for example, aliphatic acyl radicals with 1–4 C atoms, such as, for example, acetoxy or propionyloxy. Acetoxy is particularly preferred.

If Y represents alkoxy, possible radicals here are straight-chain or branched alkoxy radicals with, for example, 1–8 C atoms, preferably with 1–4 C atoms, such as, for example, methyl, ethyl, n-propyl, i-propyl, n-butyl or i-butyl.

If Y represents a pyridine, quinoline or isoquinoline radical, it is bonded via nitrogen and can be substituted, for example by lower alkyl, such as, for example, methyl or ethyl, lower alkoxy, such as, for example, methoxy or ethoxy, or carbamoyl. However, it is preferably unsubstituted.

If Y represents a carbamoyloxy or carbamoylthio group, this group can be monosubstituted or polysubstituted on the nitrogen, for example by lower alkyl with 1–4 C atoms, such as, for example, methyl or ethyl, it also being possible for the two substituents to be linked with one another to form a ring, for example to form a 5-membered or 6-membered ring, which can also be interrupted by a hetero-atom, such as, for example, oxygen, sulfur or nitrogen. The unsubstituted carbamoyl group is preferred.

Y can furthermore represent azido, as well as monosubstituted or disbustituted amino. Possible substituents are, in particular, alkyl with 1–4 C atoms, such as, for example, methyl or ethyl, it also being possible, in the case of a dialkylamino group, for the substituents to be closed to form a 5-membered or 6-membered ring which is optionally interrupted by hetero-atoms, such as, for example, morpholine or piperazine. The amino group ca, for example, also be substituted by alkoxy with 1–4 C atoms, such as, for example, methoxy or ethoxy, or by aryl, preferably phenyl, which can also carry further substituents, such as, for example, alkyl with 1–4 C atoms, preferably methyl, sulfamoyl, trifluoromethyl or halogen, such as, for example, chlorine or bromine.

If Y denotes amino, in order to avoid the formation of a ring $R_3$ must represent an ester group. This can also then be appropriate if Y denotes a hydroxyl, mercapto or monosubstituted amino group.

If Y represents a group —$SR_5$ and $R_5$ represents an acyl radical, possible acyl radicals are optionally substituted aliphatic, aromatic or heterocyclic acyl radicals, for example aliphatic acyl with 1–4 C atoms, such as, for example, acetyl or propionyl, aromatic acyl, such as, for example, benzoyl or toluoyl, and heterocyclic acyl which is derived from 5-membered or 6-membered rings with 1–4 hetero-atoms, such as, for example, nitrogen, sulfur or oxygen, such as, for example, nicotinoyl, isonicotinoyl, picolinoyl, furoyl, thenoyl, thiazoloyl, oxazoloyl, triazoloyl or thiadiazoloyl. The acetyl and propionyl radicals are preferred. $R_5$ can also denote optionally substituted aryl, preferably phenyl, the substituents corresponding to those which can be in the aryl substituting the aliphatic acyl radical ($R_1$).

If $R_5$ denotes an alkyl radical, a possible radical here is stragiht-chain or branched alkyl with, for example, 1–8 C atoms, preferably 1–4 C atoms, such as, for example, methyl, ethyl, n-propyl, i-propyl, n-butyl or i-butyl, in particular methyl and ethyl, which can also be optionally substituted, for example by amino, hydroxyl, carboxyl or carbalkoxy with 1–4 alkyl C atoms, in particular methoxycarbonyl, or by phenyl which is optionally substituted by alkyl or alkoxy with 1–4 C atoms, in particular methyl or methoxy, nitro or halogen, in particular chlorine or bromine.

If $R_5$ represents a heterocyclic radical, possible radicals are optionally substituted five-membered or six-membered rings which have 1 to 4 hetero-atoms, such as, for example, oxygen, sulfur and/or nitrogen, in particular nitrogen, optionally together with sulfur or oxygen as ring atoms.

If the radical $R_5$ denotes a heterocyclic radical, it can also be bonded to a fused aromatic 5-membered or 6-membered ring system, for example a pyridine or triazole ring, preferably to a benzene ring, but the heterocyclic ring which is not fused to a ring system is preferred. The heterocyclic ring system which forms the radical $R_5$ can also be completely or partially hydrogenated, but preferably non-hydrogenated.

The following fundamental ring systems may be mentioned as examples of the radical $R_5$: thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl, dihydropyrimidyl, tetrahydropyrimidyl and purinyl, as well as benzo-fused derivatives, for example benzoxazolyl, benzthiazolyl, benzimidazolyl and indolyl.

5-membered ring systems with a sulfur or oxygen atom and 1 to 3 nitrogen atoms, such as thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, preferably oxazol-2-yl, and oxadiazolyl, such as 1,3,4-oxadiazol-5-yl, are preferred. Furthermore, 5-membered ring systems with 2 to 4 nitrogen atoms, such as imidazolyl, preferably imidazol-2-yl, triazolyl, preferably 1,3,4-triazol-5-yl and 1,2,3- and 1,2,4-triazol-5-yl, and tetrazolyl, preferably 1 H-tetrazol-5-yl and 2 H-tetrazolyl, are preferred. Benzofused derivatives, in particular benzoxazol-2-yl, benzthiazol-2-yl and benzimidazol-2-yl, are also preferred.

Furthermore, preferred possible ring systems are 6-membered ring systems with 1 to 3, preferably 1 to 2, nitrogen atoms, such as, for example, pyridyl, such as pyrid-2-yl, pyrid-3-yl and pyrid-4-yl, pyrimidyl, preferably pyrimid-2-yl and pyrimid-4-yl, triazinyl, preferably 1,3,4-triazin-2-yl and 1,3,5-triazin-4-yl, pyridazinyl, in particular pyridazin-3-yl, and pyrazinyl. The pyridyl, pyrimid-2-yl, pyrimid-4-yl and pyridazinyl radicals, in particular the pyridine N-oxides and pyridazine N-oxides, are preferred.

If the radical $R_5$ denotes a heterocyclic radical, it can be monosubstituted or polysubstituted, examples of possible substituents being the following: straight-chain or branched alkyl groups with, for example, 1 to 15 carbon atoms, such as, for example, methyl, ethyl, n-propyl, i-propyl, n-butyl, tert.-butyl, n-hexyl, undecyl and pentadecyl, preferably those with 1–4 carbon atoms, such as, for example, methyl and ethyl, as well as lower alkyl groups with 1 to 4 carbon atoms, such as, for example, methyl, which are substituted, for example by aryl, such as, for example, phenyl or thienyl, by aryloxy, for example phenoxy, by low-molecular alkoxy, such as, for example, methoxy and ethoxy, by lower alkoxycarbonyl, such as, for example, methoxy- or ethoxy-carbonyl, by halogen, such as, for example, chlorine or bromine, by hydroxyl, by aliphatic acylamido, preferably with 1 to 4 C atoms, such as, for example, acetamido, by aromatic acylamido, such as, for example, benzamido, by amino, by alkylamino with 1 to 4 C atoms, such as, for example, methyl- or ethyl-amino, by dialkylamino with 1–4 C atoms, such as, for example, dimethyl- or diethylamino, it also being possible for the alkyl radicals of the dialkylamino group to be closed to form a 5-membered to 7-membered ring which is optionally interrupted by hetero-atoms, such as, for example, oxygen or nitrogen, such as, for example, morpholino or piperazino, by trifluoromethyl, by cyano, by carbamoyl, by carboxyl, by carboxyalkoxy with 1–4 alkyl C atoms, such as, for example, carboxymethoxy, by cyanoalkoxy with 1 to 4 alkyl C atoms, such as, for example, cyanomethoxy, by carbamoylalkoxy with 1–4 alkyl C atoms, such as, for example, carbamoylmethoxy, by alkoxycarbonyloxy with 1–4 alkyl C atoms, such as, for example, methoxycarbonyloxy, by sulfo, by alkylsulfo, preferably with 1–4 C atoms, such as, for example, methylsulfonyl, by sulfamoyl, by phosphonyl, by alkylcarbamoyl with 1–4 alkyl C atoms, such as, for example, methylcarbamoyl, by dialkylcarbamoyl with 1–4 alkyl C atoms, such as, for example, dimethylcarbamoyl, by alkyl- or dialkylsulfamoyl with 1–4 C atoms, such as, for example, methyl- or dimethyl-sulfamoyl, by carboxyalkylcarboxamido, preferably with 1–4 alkyl C atoms, such as, for example, succinamic acid, by cyanoalkylcarboxamido, preferably with 1–4 alkyl C atoms, such as, for example, malonic acid mononitrile-amide, or by alkoxycarbonylalkylcarboxamido, preferably with 1–4 C atoms in each alkyl group, it also being possible for the carboxamido nitrogen to be further substituted, such as, for example, methyl-succinamate and methyl N-methyl-succinamate.

If $R_5$ denotes a heterocyclic radical, it can furthermore be substituted by cycloalkyl with 3 to 8 C atoms, such as, for example, cyclopentyl and cyclohexyl, or by alkoxy with 1-4 C atoms, such as, for example, methoxy and ethoxy, alkenyl with 2-4 C atoms, such as, for example, allyl, alkenyloxy with 3-5 C atoms, such as, for example, allyloxy, alkyl- and alkenyl-thio with 1-4 C atoms, such as, for example, methylthio and allylthio, alkoxycarbonyl with 1-4 alkyl C atoms, such as, for example, methoxycarbonyl, alkylcarbonyl with 1-4 alkyl C atoms, such as, for example, acetyl, arylcarbonyl, such as, for example, benzoyl, carboxyalkoxycarbonyl with 1-4 C atoms, such as, for example, carboxymethoxycarbonyl, cyanoalkoxycarbonyl with 1-4 alkyl C atoms, such as, for example, cyanomethoxycarbonyl, carbamoylalkoxycarbonyl with 1 to 4 alkyl C atoms, such as, for example, carbamoylmethoxycarbonyl, alkoxycarbonylamino with 1-4 alkoxy C atoms, such as, for example, ethoxycarbonylamino, carboxyalkylthio with 1-4 alkyl C atoms, such as, for example, carboxymethylthio, amino, arylamino, such as, for example, phenylamino, heteroarylamino, such as, for example, pyrid-2-yl-amino and pyrid-4-yl-amino, monoalkyl- and dialkyl-amino with 1-4 C atoms, such as, for example, methylamino, dimethylamino, ethylamino and diethylamino, it also being possible for the two alkyl substituents to be closed to form a 5-membered to 7-membered ring which is optionally interrupted by hetero-atoms, such as, for example, oxygen or nitrogen, such as, for example, morpholino, piperidino, pyrrolidino and piperazino, carboxyalkylamino with 1-4 alkyl C atoms, such as, for example, carboxymethylamino, cyanoalkylamino with 1-4 alkyl C atoms, such as, for example, cyanomethylamino, alkoxycarbonylalkylamino with 1-4 alkoxy and alkyl C atoms, such as, for example, methoxycarbonylmethylamino, sulfoalkylamino with 1-4 C atoms, such as, for example, sulfomethylamino, sulfamoylalkylamino with 1 to 4 C atoms, such as, for example, sulfamoylmethylamino, alkylsulfamoylalkylamino with 1-4 alkyl C atoms in each case, such as, for example, methylsulfamoylmethylamino, dialkylsulfamoylalkylamino with 1-4 alkyl C atoms in each case, such as, for example, dimethylsulfamoylmethylamino, alkoxysulfonylalkylamino with 1-4 alkoxy and alkyl C atoms, such as, for example, methoxysulfonylmethylamino, oxido, hydroxyl, hydroxyalkyl with 1-4 alkyl C atoms, such as, for example, hydroxymethyl and hydroxyethyl, carboxyalkylcarbonyloxy with 1-4 alkyl C atoms, such as, for example, carboxymethylcarbonyloxy, cyanoalkylcarbonyloxy with 1 to 4 alkyl C atoms, such as, for example, cyanomethylcarbonyloxy, alkoxycarbonylalkylcarbonyloxy with 1-4 alkyl C atoms in each case, such as, for example, methoxycarbonylmethylcarbonyloxy, carboxyalkoxy with 1-4 alkyl C atoms, such as, for example, carboxymethoxy, cyanoalkoxy with 1-4 alkyl C atoms, such as, for example, cyanomethoxy, alkoxycarbonylalkoxy with 1-4 alkoxy C atoms, such as, for example, methoxycarbonylmethoxy, carbamoylalkoxy with 1-4 alkyl C atoms, such as, for example, carbamoylmethoxy, carbamoylalkylcarbonyloxy with 1-4 alkyl C atoms, such as, for example, carbamoylmethylcarbonyloxy, sulfoalkoxy with 1-4 C atoms, such as, for example, sulfomethoxy, sulfamoylalkoxy with 1-4 C atoms, such as, for example, sulfamoylmethoxy, nitro, cyano, halogen, preferably chlorine, trifluoromethyl, mercapto, carboxyl, carbamoyl, carboxyalkylaminocarbonyl with 1-4 alkyl C atoms, such as, for example, carboxymethylaminocarbonyl, carbamoylalkylaminocarbonyl with 1-4 alkyl C atoms, such as, for example, carbamoylmethylaminocarbonyl, alkoxycarbonylalkylaminocarbonyl with 1-4 alkoxy and alkyl C atoms, such as, for example, methoxycarbonylmethylaminocarbonyl, aryl radicals, such as, for example, phenyl, substituted phenyl, such as, for example, alkoxyphenyl with 1-4 alkoxy C atoms, such as, for example, methoxyphenyl and ethoxyphenyl, halogenophenyl, such as, for example, chlorophenyl, hydroxyphenyl, aminophenyl, alkylamino- or dialkylamino-phenyl with 1-4 alkyl C atoms, such as, for example, methylamino- or dimethylamino-phenyl, alkylphenyl, in particular alkylphenyl with 1-4 alkyl C atoms, such as, for example, tert.-butylphenyl, tolyl or cetylphenyl, hydroxyalkylphenyl with 1-4 alkyl C atoms, such as, for example, hydroxyethylphenyl, halogenoalkylphenyl with 1-4 alkyl C atoms, such as, for example, trifluoromethylphenyl or chloromethylphenyl, alkoxyalkylphenyl with 1-4 alkoxy and alkyl C atoms, such as, for example, methoxymethylphenyl, alkenylphenyl with 2 to 6, preferably 3-5, alkenyl C atoms, such as, for example, allylphenyl, alkenyloxyphenyl with 2-6, preferably 3-5, alkenyloxy C atoms, such as, for example, allyloxyphenyl, cyanophenyl, carbamoylphenyl, carboxyphenyl, alkoxycarbonylphenyl with 1-4 alkyl C atoms, such as, for example, methoxycarbonylphenyl, alkylcarbonyloxyphenyl with 1-4 alkyl C atoms, such as, for example, acetoxyphenyl, sulfophenyl, alkoxysulfophenyl with 1-4 alkoxy C atoms, such as, for example, methoxysulfophenyl, sulfamoylphenyl, nitrophenyl, biphenyl or optionally correspondingly substituted naphthyl radicals or heterocyclic radicals which are derived from heterocyclic 5-membered or 6-membered rings with 1 to 4 hetero-atoms, in particular nitrogen, sulfur or oxygen, such as, for example, pyridyl, furyl, quinolyl, isoquinolyl, thienyl, thiazolyl, N-pyrrolyl, pyrrolyl, imidazolyl, pyrazolyl, isoxazolyl, tetrazolyl and triazolyl.

If $R_5$ denotes a heterocyclic radical, possible substituents are also: cyanoalkylaminocarbonyl with 1-4 C atoms, such as, for example, cyanomethylaminocarbonyl, carboxyalkylcarboxamido with 1-4 C atoms, such as, for example, succinamic acid, alkoxyalkylcarboxamido with 1-4 C atoms, such as, for example, methylsuccinamate, cyanoalkylcarboxamido with 1-4 C atoms, such as, for example, malonic acid nitrile-monoamide, alkylcarbamoyl with 1-4 C atoms, such as, for example, methylaminocarbonyl, dialkylcarbamoyl with 1-4 C atoms, such as, for example, dimethylaminocarbonyl, it also being possible for the two alkyl radicals to be closed to form a carbocyclic ring with 5-7 C atoms, which can be interrupted by nitrogen, sulfur or oxygen, such as, for example, morpholinocarbonyl, alkoxycarbonylalkoxyalkyl with 1-4 C atoms, such as, for example, methoxycarbonylmethoxyalkyl, alkylcarbamoylalkoxyalkyl with 1-4 C atoms, such as, for example, methylcarbamoylmethoxymethyl, alkoxyalkylaminocarbonylalkyl, such as, for example, methoxymethylaminocarbonylmethyl, an amino group or an amino group which is monosubstituted by lower alkyl, it being possible for the amino group to be acylated by lower aliphatic or aromatic carboxylic acids, such as, for example, acetamido or benzamido, as well as an aryl or hetero-aromatic radical which is substituted by trifluoromethyl or alkylcarboxyl with 1-4 C atoms. The number of C atoms, 1-4, indicated in this paragraph in each case relates to an alkyl group contained in the radicals.

Of the 5-membered rings with 2–4 hetero-atoms, such as nitrogen, sulfur and oxygen, preferably at least one heteroatom being nitrogen, and 6-membered rings with 1–3 heteroatoms, in particular nitrogen atoms, which are preferred, according to the invention, for $R_5$, the following radicals of the general formulae II–VII may be mentioned as examples of particularly preferred radicals. In the definitions of the substituents, in each case "lower" denotes a carbon atom number of 1–4, or, in the case of an unsaturated radical, a C atom number of 2–4.

(a) A thiazolyl radical of the general formula V

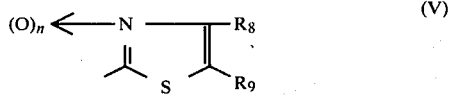

in which $R_8$ and $R_9$ can be identical or different and represent hydrogen, straight-chain or branched lower alkyl, which can be optionally substituted by halogen, lower alkoxy, hydroxyl, amino, lower alkylamino, lower dialkylamino, trifluoromethyl or phenyl, straight-chain or branched lower alkenyl, a carbocyclic ring with 3–8 carbon atoms, amino, lower alkylamino, lower dialkylamino, lower aliphatic acylamido, lower carboxyalkyl, lower alkoxycarbonylalkyl, lower carbamoylalkyl, carboxyl, carbamoyl, cyano, cyanoalkyl, lower alkoxycarbonyl, lower carboxyalkylaminocarbonyl, lower alkoxycarbonylalkylaminocarbonyl, cyanoalkylaminocarbonyl, lower carboxyalkylcarboxamido, lower alkoxycarbonylalkylcarboxamido, lower cyanoalkylcarboxamido, lower carboxyalkylthio, an optionally substituted hetero-aryl radical or a phenyl radical which is optionally substituted by one or two halogen atoms, lower alkyl, lower alkoxy, hydroxyl, lower alkylamino, lower dialkylamino, lower alkylthio, cyano or trifluoromethyl, it being possible for $R_8$ and $R_9$ together to form an optionally substituted carbocyclic ring with 5–7 carbon atoms, and n represents 0 or 1.

Examples which may be mentioned are, in particular: 1,3-thiazol-2-yl, 4-methyl-1,3-thiazol-2-yl, 4-tert.-butyl-1,3-thiazol-2-yl, 4-n-propyl-1,3-thiazol-2-yl, 4-ethyl-1,3-thiazol-2-yl, 5-amino-1,3-thiazol-2-yl, 5-acetamido-1,3-thiazol-2-yl, 5-methylamino-1,3-thiazol-2-yl, benzothiazol-2-yl, 5-chloro-benzothiazol-2-yl, 4-methyl-3-oxy-1,3-thiazol-2-yl, 3-oxy-4-phenyl-1,3-thiazol-2-yl, 4-(4-chlorophenyl)-3-oxy-1,3-thiazol-2-yl, 3-oxy-1,3-thiazol-2-yl, 4-(4-bromophenyl)-3-oxy-1,3-thiazol-2-yl, 3-oxy-4-(p-tolyl)-1,3-thiazol-2-yl, 4-(p-methoxyphenyl)-3-oxy-1,3-thiazol-2-yl, 4-methyl-3-oxy-5-phenyl-1,3-thiazol-2-yl, 5-methyl-3-oxy-4-phenyl-1,3-thiazol-2-yl, 5-methyl-1,3-thiazol-2-yl, 4-trifluoromethyl-1,3-thiazol-2-yl, 4-phenyl-1,3-thiazol-2-yl, 4,5-dimethyl-1,3-thiazol-2-yl, 4-(3-pyridyl)-1,3-thiazol-2-yl, 4-carboxymethyl-1,3-thiazol-2-yl, 3-carboxy-4-methyl-1,3-thiazol-2-yl, 4-carboxy-1,3-thiazol-2-yl, 4-ethoxycarbonyl-5-amino-1,3-thiazol-2-yl, 5-amino-4-carboxy-1,3-thiazol-2-yl, 5-carboxymethylaminocarbonyl-1,3-thiazol-2-yl, 5-carboxymethylcarboxamido-1,3-thiazol-2-yl, 5-carboxymethyl-4-phenyl-1,3-thiazol-2-yl, 4-(5-nitro-thien-2-yl)-1,3-thiazol-2-yl, 4-(4-carboxythien-2-yl)-1,3-thiazol-2-yl, 4-(1-methyl-pyrrol-2-yl)-1,3-thiazol-2-yl, 4-(5-carbamoyl-fur-2-yl)-1,3-thiazol-2-yl and 5-carboxy-4-methyl-1,3-thiazol-2-yl.

(b) A pyridyl radical of the general formula VI

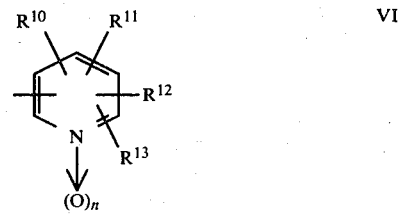

in which $R^{10}$ to $R^{13}$ can be identical or different and denote hydrogen, halogen, lower, straight-chain or branched alkyl or alkenyl, trifluoromethyl, lower alkylcarbonyl, amino, lower alkylamino, lower dialkylamino, carboxyl, carbamoyl, cyano, lower alkylaminocarbonyl, lower dialkylaminocarbonyl, lower alkoxycarbonyl, hydroxyl, lower alkoxy, lower hydroxyalkyl, lower alkylthio or nitro and n represents 0 or 1.

Examples which may be mentioned are, in particular: 1-oxy-pyrid-2-yl, 3-methyl-1-oxy-pyrid-2-yl, 4-methyl-1-oxy-pyrid-2-yl, 1-oxy-pyrid-4-yl, 5-methyl-1-oxy-pyrid-2-yl, 6-methyl-1-oxy-pyrid-2-yl, 3-ethoxy-1-oxy-pyrid-2-yl, 5-bromo-1-oxy-pyrid-2-yl, pyrid-2-yl, pyrid-3-yl, pyridin-4-yl, 3-hydroxy-pyrid-2-yl, 3-nitro-pyrid-2-yl, 5-nitro-pyrid-2-yl, 2-amino-6-methyl-pyrid-3-yl, 4-chloro-1-oxy-pyridin-2-yl, 2-carboxy-pyrid-4-yl, 3-carboxy-pyrid-5-yl and 4-carboxy-pyrid-5-yl.

(c) Oxadiazolyl, thiadiazolyl and triazolyl radicals of the general formulae VII, VII a and VII b

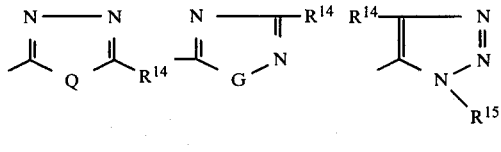

in which Q represents oxygen, sulfur or $>$N-$R^{15}$ and G represents oxygen or sulfur, and wherein $R^{14}$ denotes hydrogen, lower, straight-chain or branched alkyl, lower straight-chain or branched alkenyl, a carbocyclic ring with 5–7 carbon atoms, hydroxyl, lower hydroxyalkyl, lower alkoxy, lower alkylthio, lower alkoxyalkyl, an amino group, which can be optionally substituted by one or two lower alkyl radicals which together can also form a carbocyclic ring with 5–7 carbon atoms, lower aliphatic or aromatic acylamido, a lower aminoalkyl group, which can be optionally substituted by one or two lower, branched or straight-chain alkyl radicals, which together can also form a carbocyclic ring with 5–7 carbon atoms, or acylated by a lower aliphatic or aromatic carboxylic acid, trifluoromethyl, lower alkoxycarbonylalkylamido, lower carboxyalkylamido, lower cyanoalkylamido, lower alkoxycarboxyalkoxyalkyl, lower carboxyalkyl, lower alkoxycarbonylalkyl, lower cyanoalkyl, carboxyl, carbamoyl, cyano, lower carbamoylalkyl, lower alkoxycarbonyl, lower alkylcarbamoyl, lower dialkylcarbamoyl, lower sulfoalkyl, lower sulfamoylalkyl, lower alkylsulfamoylalkyl, lower dialkylsulfamoylalkyl, lower alkylcarbamoylalkyl, lower dialkylcarbamoylalkyl, lower alkoxycarbonylalkoxyalkyl, lower carboxyalkoxyalkyl, lower carbamoylalkoxyalkyl, lower alkylcarbamoylalkoxyalkyl, lower alkoxyalkylaminocarbonylalkyl, lower carboxyalkylthio and an aryl or heterocyclic radical, preferably a phenyl, naphthyl, thienyl, furyl, thiazolyl, pyrrolyl, imidazolyl, pyrazolyl, isoxazolyl, quinolyl, isoquinolyl or pyridyl radical, which is optionally substituted by one or two halogen atoms, hydroxyl, lower alkoxy, lower, straight-chain or branched alkyl, lower, straight-chain or branched alkenyl, trifluoromethyl, cyano, amino, carboxyl, lower alkoxycarbonyl, sulfo, carbamoyl, sufamoyl, lower alkylcarboxy, lower alkylcarbonyl, lower alkylamino, nitro or lower dialkylamino, or an arylamino or heteroarylamino group or lower arylalkyl, and in which $R^{15}$ can be hydrogen, lower straight-chain or branched alkyl, lower straight-chain or branched alkenyl, lower carboxyalkyl, lower alkoxycarbonylalkyl, lower cyanoalkyl, lower sulfoalkyl, lower sulfamoylalkyl, lower alkylsulfamoylalkyl, lower dialkylsulfamoylalkyl, lower alkylcarbamoylalkyl, lower dialkylcarbamoylalkyl, lower alkoxycarbonylalkoxyalkyl, lower carboxyalkoxyalkyl, lower carbamoylalkoxyalkyl, lower alkylcarbamoylakoxyalkyl, hydroxyl, lower hydroxyalkyl, an amino group which can be optionally acylated with a lower aliphatic carboxylic acid or alkylated with one or two lower alkyl radicals, lower arylalkyl, lower alkoxyalkyl, a carbocyclic ring with 5 to 7 carbon atoms, a pyrrolyl radical, which can be optionally substituted by one or two lower alkyl groups, or an aryl or heterocyclic radical, preferably a phenyl or pyridine radical, which can be optionally substituted by carboxyl, cyano, trifluoromethyl, carbamoyl, amino, lower alkylamino, lower dialkylamino, lower alkyl, sulfo, sulfamoyl, lower alkoxycarbonyl, hydroxyl, lower hydroxyalkyl, lower alkylcarbonyl or lower alkoxy.

Examples which may be mentioned are, in particular: for

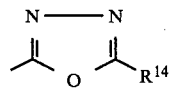

1,3,4-oxadiazol-5-yl, 2-methyl-1,3,4-oxadiazol-5-yl, 2-phenyl-1,3,4-oxadiazol-5-yl, 2-(4-fluorophenyl)-1,3,4-oxadiazol-5-yl, 2-(2-bromophenyl)-1,3,4-oxadiazol-5-yl, 2-(2-methoxyphenyl)-1,3,4-oxadiazol-5-yl, 2-cyclohexyl-1,3,4-oxadiazol-5-yl, 2-(2-pyridyl)-1,3,4-oxadiazol-5-yl, 2-(3-pyridyl)-1,3,4-oxadiazol-5-yl, 2-(4-pyridyl)-1,3,4-oxadiazol-5-yl, 2-(2-furyl)-1,3,4-oxadiazol-5-yl, 2-(3-furyl)-1,3,4-oxadiazol-5-yl, 2-(2-thienyl)-1,3,4-oxadiazol-5-yl, 2-propyl-1,3,4-oxadiazol-5-yl, 2-butyl-1,3,4-oxadiazol-5-yl, 2-(2-hydroxyphenyl)-1,3,4-oxadiazol-5-yl, 2-ethyl-1,3,4-oxadiazol-5-yl, 2-(4-nitrophenyl)-1,3,4-oxadiazol-5-yl, 2-(3-thienyl)-1,3,4-oxadiazol-5-yl, 2-(4-chlorophenyl)-thienyl-1,3,4-oxadiazol-5-yl, 2-(2-thiazolyl)-1,3,4-oxadiazol-5-yl, 2-(3-nitrophenyl)-1,3,4-oxadiazol-5-yl, 2-(2-tolyl)-1,3,4-oxadiazol-5-yl, 2-(3-tolyl)-1,3,4-oxadiazol-5-yl, 2-(4-hydroxyphenyl)-1,3,4-oxadiazol-5-yl, 2-benzyl-1,3,4-oxadiazol-5-yl, 2-(1-naphthyl)-1,3,4-oxadiazol-5-yl, 2-(2-pyrrolyl)-1,3,4-oxadiazol-5-yl, 2-(4-imidazolyl)-1,3,4-oxadiazol-5-yl, 2-(5-pyrazolyl)-1,3,4-oxadiazol-5-yl, 2-(3,5-dimethyl-4-isoxazolyl)-1,3,4-oxadiazol-5-yl, 2-(ethoxycarbonylmethoxymethyl)-1,3,4-oxadiazol-5-yl, 2-(carboxymethoxymethyl)-1,3,4-oxadiazol-5-yl, 2-carbamoyl-1,3,4-oxadiazol-5-yl, 2-(N-methylcarbamoyl)-1,3,4-oxadiazol-5-yl, 2-(N-ethylcarbamoyl)-1,3,4-oxadiazol-5-yl, 2-(N,N-dimethylcarbamoyl)-1,3,4-oxadiazol-5-yl and 2-(N,N-dimethylaminomethyl)-1,3,4-oxadiazol-5-yl, for

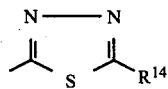

1,3,4-thiadiazol-5-yl, 2-butyl-1,3,4-thiadiazol-5-yl, 2-propyl-1,3,4-thiadiazol-5-yl, 2-phenyl-1,3,4-thiadiazol-5-yl, 2-amino-1,3,4-thiadiazol-5-yl, 2-ethyl-1,3,4-thiadiazol-5-yl, 2-acetamido-1,3,4-thiadiazol-5-yl, 2-methylamino-1,3,4-thiadiazol-5-yl, 2-(N-methylacetamido)-1,3,4-thiadiazol-5-yl, 2-isobutylamino-1,3,4-thiadiazol-5-yl, 2-piperidino-1,3,4-thiadiazol-5-yl, 2-pyrrolidino-1,3,4-thiadiazol-5-yl, 2-aminomethyl-1,3,4-thiadiazol-5-yl, 2-acetamidomethyl-1,3,4-thiadiazol-5-yl, 2-benzamido-1,3,4-thiadiazol-5-yl, 2-(β-piperidinoethyl)-1,3,4-thiadiazol-5-yl, 2-(2-pyridylamino)-1,3,4-thiadiazol-5-yl, 2-(3-pyridylamino)-1,3,4-thiadiazol-5-yl, 2-(1,3-thiazol-2-ylamino)-1,3,4-thiadiazol-5-yl, 2-(1,3,4-triazolyl-2-amino)-1,3,4-thiadiazol-5-yl, 2-(tetrazolyl-5-amino)-1,3,4-thiadiazol-5-yl, 2-dimethylaminomethyl-1,3,4-thiadiazol-5-yl, 2-methylaminomethyl-1,3,4-thiadiazol-5-yl, 2-ethyl-1,3,4-thiadiazol-5-yl, 2-trifluoromethyl-1,3,4-thiadiazol-5-yl, 2-methylthio-1,3,4-thiadiazol-5-yl, 2-(2-pyridyl)-1,3,4-thiadiazol-5-yl, 2-(3-pyridyl)-1,3,4-thiadiazol-5-yl, 2-(4-pyridyl)-1,3,4-thiadiazol-5-yl, 2-(2-thienyl)-1,3,4-thiadiazol-5-yl, 2-(2-furyl)-1,3,4-thiadiazol-5-yl, 2-(3-furyl)-1,3,4-thiadiazol-5-yl, 2-methyl-1,3,4-thiadiazol-5-yl, 2-isopropyl-1,3,4-thiadiazol-5-yl, 2-(4-methoxyphenyl)-1,3,4-thiadiazol-5-yl, 2-(4-chlorophenyl)-1,3,4-thiadiazol-5-yl, 2-(1-naphthyl)-1,3,4-thiadiazol-5-yl, 2-(2-quinolyl)-1,3,4-thiadiazol-5-yl, 2-(1-isoquinolyl)-1,3,4-thiadiazol-5-yl, 2-(β-methoxycarbonylpropionylamido)-1,3,4-thiadiazol-5-yl, 2-(β-carboxypropionylamido)-1,3,4-thiadiazol-5-yl, 2-carboxymethoxymethyl-1,3,4-thiadiazol-5-yl, 2-ethoxycarbonylmethyl-1,3,4-thiadiazol-5-yl, 2-carboxymethyl-1,3,4-thiadiazol-5-yl, 2-(α-carboxyacetamido)-1,3,4-thiadiazol-5-yl, 2-(α-cyanoacetamido)-1,3,4-thiadiazol-5-yl, 2-methoxycarbamoyl)-acetamido-1H-1,3,4-thiadiazol-5-yl, 2-(N,N-dimethylcarbamoylmethyl)-1H-1,3,4-thiadiazol-5-yl, 2-(N,N-diethylcarbamoylmethyl)-1H-1,3,4-thiadiazol-5-yl, 2-(N,N-dipropylcarbamoylmethyl)-1H-1,3,4-thiadiazol-5-yl, 2-(N,N-dibutylcarbamoylmethyl)-1H-1,3,4-thiadiazol-5-yl, 2-(2-acetamidoethyl)-1,3,4-thiadiazol-5-yl, 2-(2-aminoethyl)-1,3,4-thiadiazol-5-yl, 2-hydroxymethyl-1,3,4-thiadiazol-5-yl, 2-(2-hydroxyethyl)-1,3,4-thiadiazol-5-yl, 2-(isobutyryloxymethyl)-1,3,4-thiadiazol-5-yl, 2-(ethoxycarbonylmethoxymethyl)-1,3,4-thiadiazol-5-yl, 2-(carbamoylmethoxymethyl)-1,3,4-thiadiazol-5-yl, 2-(N-methylcarbamoyl)-1,3,4-thiadiazol-5-yl, 2-isobutyl-1,3,4-thiadiazol-5-yl, 2-methoxypropylaminocarbonylmethyl-1,3,4-thiadiazol-5-yl, 2-carboxyethyl-1,3,4-thiadiazol-5-yl, 2-sulfoethyl-1,3,4-thiadiazol-5-yl, 2-carboxy-1,3,4-thiadiazol-5-yl, 2-phenylamino-1,3,4-thiadiazol-5-yl, 2-o-carboxybenzoylamino-1,3,4-thiadiazol-5-yl, 2-(1-carboxyethylthio)-1,3,4-thiadiazol-5-yl and 2-(1-carboxy-1-methylethyl)-1,3,4-thiadiazol-5-yl, for

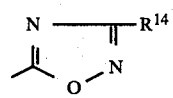

1,2,4-oxadiazol-5-yl, 3-methyl-1,2,4-oxadiazol-5-yl and 3-phenyl-1,2,4-oxadiazol-5-yl, for

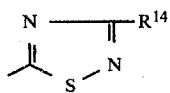

1,2,4-thiadiazol-5-yl, 3-phenyl-1,2,4-thiadiazol-5-yl, 3-methylmercapto-1,2,4-thiadiazol-5-yl, 3-methyl-1,2,4-thiadiazol-5-yl and 3-ethyl-1,2,4-thiadiazol-5-yl, for

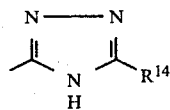

2-methyl-1H-1,3,4-triazol-5-yl, 2-ethyl-1H-1,3,4-triazol-5-yl, 2-amino-1H-1,3,4-triazol-5-yl, 1H-1,3,4-triazol-5-yl, 2-trifluoromethyl-1H-1,3,4-triazol-5-yl, 2-($\beta$-piperidinoethyl)-1H-1,3,4-triazol-5-yl, 2-($\beta$-diethylaminoethyl)-1H-1,3,4-triazol-5-yl, 2-hydroxy-1H-1,3,4-triazol-5-yl, 2-(4-pyridyl)-1H-1,3,4-triazol-5-yl, 2-tert.-butyl-1H-1,3,4-triazol-5-yl, 2-(3-pyridyl)-1H-1,3,4-triazol-5-yl, 2-(2-pyridyl)-1H-1,3,4-triazol-5-yl, 2-acetamido-1H-1,3,4-triazol-5-yl, 2-propionylamido-1H-1,3,4-triazol-5-yl, 2-benzamido-1H-1,3,4-triazol-5-yl, 2-(2-thienyl)-1H-1,3,4-triazol-5-yl, 2-(2-furyl)-1H-1,3,4-triazol-5-yl, 2-(3-furyl)-1H-1,3,4-triazol-5-yl, 2-methoxymethyl-1H-1,3,4-triazol-5-yl, 2-(4-sulfamoyl-phenyl)-1H-1,3,4-triazol-5-yl, 2-phenyl-1H-1,3,4-triazol-5-yl, 2-(4-methoxyphenyl)-1H-1,3,4-triazol-5-yl, 2-(4-chlorophenyl)-1H-1,3,4-triazol-5-yl, 2-(2-methyl-pyrid-4-yl)-1H-1,3,4-triazol-5-yl, 2-phenoxymethyl)-1H-1,3,4-triazol-5-yl, 2-ethoxymethyl-1H-1,3,4-triazol-5-yl, 2-(2-ethoxyethyl)-1H-1,3,4-triazol-5-yl, 2-amino-ethyl-1H-1,3,4-triazol-5-yl, 2-acetamidomethyl-1H-1,3,4-triazol-5-yl, 2-ethoxycarbonylmethyl-1H-1,3,4-triazol-5-yl, 2-($\beta$-carbomethoxypropionylamido)-1H-1,3,4-triazol-5-yl, 2-carboxymethyl-1H-1,3,4-triazol-5-yl, 2-carboxymethoxymethyl-1H-1,3,4-triazol-5-yl, 2-ethoxycarbonylmethoxymethyl-1H-1,3,4-triazol-5-yl, 2-ethoxycarbonyl-1H-1,3,4-triazol-5-yl, 2-carbamoyl-1H-1,3,4-triazol-5-yl, 2-carbamoylmethoxymethyl-1H-1,3,4-triazol-5-yl and 2-(N-ethylcarbamoylmethoxymethyl)-1H-1,3,4-triazol-5-yl, for

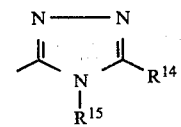

in which $R^{15} \neq$ hydrogen 2-amino-1-methyl-1,3,4-triazol-5-yl, 1-methyl-1,3,4-triazol-5-yl, 1-methyl-2-trifluoromethyl-1,3,4-triazol-5-yl, 1,2-dimethyl-1,3,4-triazol-5-yl, 2-hydroxy-1-methyl-1,3,4-triazol-5-yl, 1-methyl-2-(3-pyridyl)-1,3,4-triazol-5-yl, 1-methyl-2-(4-pyridyl)-1,3,4-triazol-5-yl, 2-(2-furyl)-1-methyl-1,3,4-triazol-5-yl, 1-methyl-2-(2-thienyl)-1,3,4-triazol-5-yl, 1-methyl-2-(2-pyridyl)-1,3,4-triazol-5-yl, 2-(3-furyl)-1-methyl-1,3,4-triazol-5-yl, 1-methyl-2-phenyl-1,3,4-triazol-5-yl, 1-ethyl-1,3,4-triazol-5-yl, 1-ethyl-2-(3-pyridyl)-1,3,4-triazol-5-yl, 1-ethyl-2-(4-pyridyl)-1,3,4-triazol-5-yl, 1-ethyl-2-(2-pyridyl)-1,3,4-triazol-5-yl, 2-(3-furyl)-1-methyl-1,3,4-triazol-5-yl, 1-ethyl-2-trifluoromethyl-1,3,4-triazol-5-yl, 1-ethyl-2-(2-furyl)-1,3,4-triazol-5-yl, 1-ethyl-2-(2-thienyl)-1,3,4-triazol-5-yl, 1,2-diethyl-1,3,4-triazol-5-yl, 1-propyl-2-(3-pyridyl)-1,3,4-triazol-5-yl, 2-(2-furyl)-1-propyl-1,3,4-triazol-5-yl, 1-propyl-1,3,4-triazol-5-yl, 1-isopropyl-1,3,4-triazol-5-yl, 1-allyl-1,3,4-triazol-5-yl, 1-butyl-1-(2-furyl)-1,3,4-triazol-5-yl, 1-cyclohexyl-1,3,4-triazol-5-yl, 1-benzyl-1,3,4-triazol-5-yl, 1-hydroxy-1,3,4-triazol-5-yl, 1-methoxymethyl-1,3,4-triazol-5-yl, 1-phenyl-1,3,4-triazol-5-yl, 2-methyl-1-phenyl-1,3,4-triazol-5-yl, 1-(4-chlorophenyl)-1,3,4-triazol-5-yl, 2-hydroxy-1-phenyl-1,3,4-triazol-5-yl, 2-amino-1-phenyl-1,3,4-triazol-5-yl, 1-phenyl-2-propyl-1,3,4-triazol-5-yl, 2-(1-piperidinomethyl)-1-phenyl-1,3,4-triazol-5-yl, 2-($\beta$-diethylaminoethyl)-1-phenyl-1,3,4-triazol-5-yl, 1-(4-ethoxyphenyl)-2-($\beta$-piperidinoethyl)-1,3,4-triazol-5-yl, 1-(4-chlorophenyl)-2-dimethylaminomethyl-1,3,4-triazol-5-yl, 1-phenyl-2-(4-pyridyl)-1,3,4-triazol-5-yl, 1-(3-pyridyl)-1,3,4-triazol-5-yl, 2-hydroxy-1-(2-pyridyl)-1,3,4-triazol-5-yl, 1-(4-pyridyl)-1,3,4-triazol-5-yl, 1-(2-pyridyl)-1,3,4-triazol-5-yl, 1-(4-ethoxyphenyl)-2-hydroxy-1,3,4-triazol-5-yl, 1-(4-chlorophenyl)-2-hydroxy-1,3,4-triazol-5-yl, 1-amino-2-trifluoromethyl-1,3,4-triazol-5-yl, 1-amino-2-(2-hydroxyphenyl)-1,3,4-triazol-5-yl, 1-amino-2-phenyl-1,3,4-triazol-5-yl, 1-amino-2-(4-fluorophenyl)-1,3,4-triazol-5-yl, 1-amino-2-(2-bromophenyl)-1,3,4-triazol-5-yl, 1-amino-2-(2-methoxyphenyl)-1,3,4-triazol-5-yl, 1-amino-2-(4-pyridyl)-1,3,4-triazol-5-yl, 1-amino-2-(2-thienyl)-1,3,4-triazol-5-yl, 1-amino-2-cyclohexyl-1,3,4-triazol-5-yl, 1-amino-2-methyl-1,3,4-triazol-5-yl, 2-ethyl-1-amino-1,3,4-triazol-5-yl, 2-phenyl-1-phenylamino-1,3,4-triazol-5-yl, 2-ethyl-1-ethylamino-1,3,4-triazol-5-yl, 1-amino-2-methylthio-1,3,4-triazol-5-yl, 1-amino-2-mercapto-1,3,4-triazol-5-yl, 1-amino-2-benzyl-1,3,4-triazol-5-yl, 1-acetamido-2-ethyl-1,3,4-triazol-5-yl, 2-ethyl-1-(2,5-dimethyl-pyrrol-1-yl)-1,3,4-triazol-5-yl, 2-ethyl-1-(pyrrol-1-yl)-1,3,4-triazol-5-yl, 1-methyl-2-(4-sulfamoylphenyl)-1,3,4-triazol-5-yl, 1-allyl-2-(4-sulfamoylphenyl)-1,3,4-triazol-5-yl, 1-phenyl-2-(4-sulfamoylphenyl)-1,3,4-triazol-5-yl, 1-amino-1,3,4-triazol-5-yl, 1-(4-ethoxyphenyl)-2-(4-pyridyl)-1,3,4-triazol-5-yl, 1-(4-ethoxyphenyl)-2-(3-pyridyl)-1,3,4-triazol-5-yl, 1-(4-methoxyphenyl)-2-(4-pyridyl)-1,3,4-triazol-5-yl, 1-(4-ethoxyphenyl)-2-phenyl-1,3,4-triazol-5-yl, 1-(4-ethoxyphenyl)-2-(4-aminophenyl)-1,3,4-triazol-5-yl, 1,2-diphenyl-1,3,4-triazol-5-yl, 1,2-di-p-tolyl-1,3,4-triazol-5-yl, 1-allyl-2-phenyl-1,3,4-triazol-5-yl, 1-amino-2-carboxymethyl-1,3,4-triazol-5-yl, 2-carboxymethyl-1-methyl-1,3,4-triazol-5-yl, 2-carboxymethoxymethyl-1-methyl-1,3,4-triazol-5-yl, 1-carboxymethyl-2-trifluoromethyl-1,3,4-triazol-5-yl, 1-carbamoylmethyl-2-trifluoromethyl-1,3,4-triazol-5-yl, 1-sulfoethyl-2-trifluoromethyl-1,3,4-triazol-5-yl, 2-ethoxycarbonylmethoxymethyl-1-methyl-1,3,4-triazol-5-yl, 2-carbamoyl-1-methyl-1,3,4-triazol-5-yl, 2-carbamoylmethoxymethyl-1-methyl-1,3,4-triazol-5-yl, 2-ethoxycarbonyl-1-(4-methoxybenzyl)-1,3,4-triazol-5-yl and 1-amino-2-carboxymethylthio-1,3,4-triazol-5-yl, and for

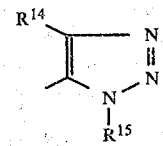

1H-1,2,3-triazol-5-yl, 1-methyl-1,2,3-triazol-5-yl, 1,4-dimethyl-1,2,3-triazol-5-yl, 1H-4-methyl-1,2,3-triazol- 5-yl, 1,4-diethyl-1,2,3-triazol-5-yl, 4-carboxy-1H-1,2,3-triazol-5-yl, 4-(2-carboxyethyl)-1H-1,2,3-triazol-5-yl, 4-(3-carboxypropyl)-1H-1,2,3-triazol-5-yl, 4-(1-carboxy-1-methylethyl)-1H-1,2,3-triazol-5-yl, 4-(2-carboxy-2-methylpropyl)-1H-1,2,3-triazol-5-yl, 4-N-methylcarbamoyl-1H-1,2,3-triazol-5-yl, 4-N-ethylcarbamoyl-1H-1,2,3-triazol-5-yl, 4-N-propylcarbamoyl-1H-1,2,3-triazol-5-yl and 4-N-butylcarbamoyl-1H-1,2,3-triazol-5-yl.

(d) A triazolyl radical of the general formula VIII

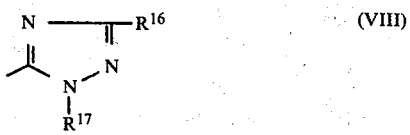

(VIII)

in which $R^{16}$ and $R^{17}$, which can be identical or different, denote lower straight-chain or branched alkyl, lower straight-chain or branched alkenyl, lower alkoxyalkyl, hydroxyl, hydroxyalkyl, lower alkoxy, lower alkylcarbonyl or an optionally substituted phenyl radical, and furthermore $R^{16}$ can represent hydrogen.

Examples which may be mentioned are, in particular: 1-methyl-1,2,4-triazol-5-yl, 1-butyl-1,2,4-triazol-5-yl, 1-phenyl-1,2,4-triazol-5-yl, 1-methoxymethyl-1,2,4-triazol-5-yl, 1,3-dimethyl-1,2,4-triazol-5-yl, 1-allyl-1,2,4-triazol-5-yl, 3-hydroxy-1-methyl-1,2,4-triazol-5-yl, 3-hydroxy-1-isopropyl-1,2,4-triazol-5-yl, 3-hydroxy-1-phenyl-1,2,4-triazol-5-yl, 3-ethyl-1-methyl-1,2,4-triazol-5-yl and 3methyl-1-phenyl-1,2,4-triazol-5-yl.

(e) A pyrimidinyl and pyridazinyl radical of the general formulae IX, IX a and IX b

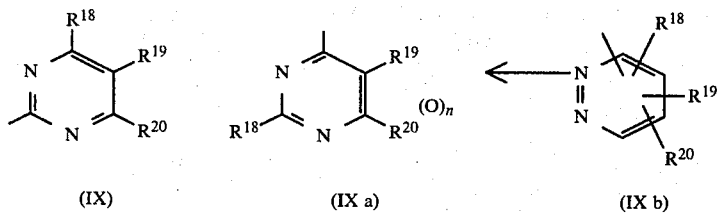

(IX)      (IX a)      (IX b)

in which $R^{18}$ to $R^{20}$, which can be identical or different, denote hydrogen, halogen, lower straight-chain or branched alkyl, lower straight-chain or branched alkenyl, mercapto, lower alkylthio, hydroxyl, lower hydroxyalkyl, lower alkoxy, lower alkylcarbonyl, lower alkoxyalkyl, an amino group which can be optionally substituted by one or two lower alkyl radicals, lower carboxyalkyl, carboxyl, cyano, lower alkoxycarbonyl, a carbamoyl group which can be optionally substituted by one or two lower alkyl groups, which in turn can form a carbocyclic ring with 5-7 C atoms which can be optionally interrupted by nitrogen or sulfur, lower alkoxycarbonylalkylamido, lower carboxyalkylamido, lower cyanoalkyl, an optionally substituted phenyl radical or lower carboxyalkylthio and the heterocyclic rings can also be partially hydrogenated and n represents 0 or 1.

Examples which may be mentioned are, in particular: for

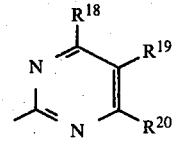

4,6-diamino-pyrimidin-2-yl, 4-amino-6-hydroxy-pyrimidin-2-yl, 5,6-diamino-4-hydroxy-pyrimidin-2-yl, 4,5-diamino-pyrimidin-2-yl, 4-hydroxy-6-methyl-pyrimidin-2-yl, 4,6-dihydroxy-pyrimidin-2-yl, 4-hydroxy-pyrimidin-2-yl, 4-hydroxy-6-propyl-pyrimidin-2-yl, pyrimidin-2-yl, 4-methyl-pyrimidin-2-yl, 4,6-dimethyl-pyrimidin-2-yl, 4-mercapto-pyrimidin-2-yl, 4-methylthio-pyrimidin-2-yl, 1,4,5,6-tetrahydropyrimidin-2-yl, 4-hydroxy-6-methyl-pyrimidin-2-yl-5-acetic acid, 4-hydroxy-pyrimidin-2-yl-5-carboxylic acid, 4-amino-pyrimidin-2-yl-5-carboxylic acid, methyl 4-amino-pyrimidin-2-yl-5-carboxylate, ethyl 4-amino-pyrimidin-2-yl-5-carboxylate, 4-hydroxy-pyrimidin-2-yl-5-acetic acid, 4-hydroxy-5-piperidino-carbonyl-pyrimidin-2-yl, 4-chloro-pyrimidin-2-yl-5-carboxylic acid, 4-(β-carboxy-propionylamido)-6-hydroxy-pyrimidin-2-yl and 5-cyanoethyl-4-hydroxy-6-methylpyrimidin-2-yl, for

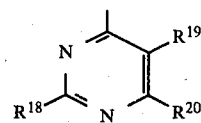

2-hydroxy-pyrimidin-4-yl, pyrimidin-4-yl, 5-ethoxycarbonyl-6-methyl-2-phenyl-pyrimidin-4-yl, 6-ethoxy-5-ethoxycarbonyl-2-phenyl-pyrimidin-4-yl, 5-ethoxycarbonyl-6-amino-2-phenyl-pyrimidin-4-yl, 5-cyano-2-hydroxy-6-methyl-pyrimidin-4-yl, 5-acetyl-2,6-dimethyl-pyrimidin-4-yl, 5-ethoxycarbonyl-2,6-dimethyl-pyrimidin-4-yl, 2-hydroxy-6-methyl-pyrimidin-4-yl, 6-mercapto-2-methyl-pyrimidin-4-yl, 6-mercaptopyrimidin-4-yl, 2-amino-6-mercapto-pyrimidin-4-yl, 6-mercapto-2-methylthio-pyrimidin-4-yl, 6-carboxymethylthio-pyrimidin-4-yl, 6-carboxymethylthio-2-methyl-pyrimidin-4-yl and 2-amino-4-carboxymethylthio-pyrimidin-4-yl, and for

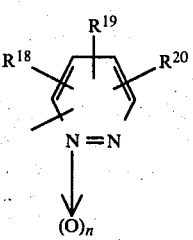

6-methoxy-2-oxy-pyridazin-3-yl, 6-butoxy-2-oxy-pyridazin-3-yl, 6-ethoxy-2-oxy-pyridazin-3-yl, 6-chloro-2-oxy-pyridazin-3-yl, 2-oxy-pyridazin-3-yl, 6-methyl-1-oxy-pyridazin-3-yl, 6-methyl-2-oxy-pyridazin-3-yl, pyridazin-3-yl, 6-hydroxy-pyridazin-3-yl, 6-chloro-1-oxy-pyridazin-3-yl, 5-ethoxycarbonyl-6-hydroxy-pyridazin-3-yl, 5-carboxy-6-hydroxy-pyridazin-3-yl, 4-ethoxy-carbonyl-6-hydroxy-pyridazin-3-yl, 4-methyl-6-hydroxy-pyridazin-3-yl, 4-ethyl-6-hydroxy-pyridazin-3-yl, 5-ethoxycarbonyl-6-hydroxy-4-methyl-pyridazin-3-yl, 5-ethoxycarbonyl-4-ethyl-6-hydroxy-pyridazin-3-yl, 4-ethoxycarbonyl-5-ethyl-6-hydroxy-pyridazin-3-yl, 4-ethoxycarbonyl-6-hydroxy-5-methylpyridazin-3-yl and 6-mercaptopyridazin-3-yl.

(f) A tetrazolyl radical of the general formula X

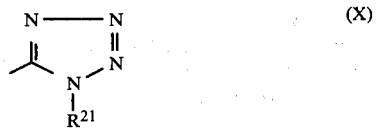

in which $R^{21}$ represents hydrogen, lower straight-chain or branched alkyl, lower branched or straight-chain alkenyl, lower alkoxyalkyl, an optionally substituted aryl or heteroaryl radical, a carbocyclic ring with 5–7 C atoms, lower arylalkyl, lower carboxyalkyl, lower cyanoalkyl, lower alkoxycarbonylalkyl, lower sulfoalkyl, lower sulfamoylalkyl, lower alkylsulfoalkyl, lower alkylsulfamoylalkyl, lower dialkylsulfamoylalkyl, lower carbamoylalkyl, lower alkylcarbamoylalkyl, lower dialkylcarbamoylalkyl, lower aminoalkyl, lower hydroxyalkyl or lower alkylamidoalkyl.

Examples which may be mentioned are, in particular: tetrazol-5-yl, 1-ethyl-tetrazol-5-yl, 1-allyl-tetrazol-5-yl, 1-phenyl-tetrazol-5-yl, 1-butyl-tetrazol-5-yl, 1-benzyl-tetrazol-5-yl, 1-(4-fluorophenyl)-tetrazol-5-yl, 1-isopropyl-tetrazol-5-yl, 1-(2-pyridyl)-tetrazol-5-yl, 1-cyclohexyl-tetrazol-5-yl, 1-(2,4-dichlorophenyl)-tetrazol-5-yl, 1-(2-tolyl)-tetrazol-5-yl, 1-(4-nitrophenyl)-tetrazol-5-yl, 1-(4-dimethylaminophenyl)-5-yl, 1-methoxymethyl-tetrazol-5-yl, 1-methyl-tetrazol-5-yl, 1-propyl-tetrazol-5-yl, 1-cyclopentyl-tetrazol-5-yl, 1-(4-chlorophenyl)-tetrazol-5-yl, 1-carboxymethyl-tetrazol-5-yl, 1-carboxyethyl-tetrazol-5-yl, 1-cyanomethyl-tetrazol-5-yl, 1-sulfomethyl-tetrazol-5-yl, 1-sulfoethyl-tetrazol-5-yl, 1-sulfopropyl-tetrazol-5-yl, 1-sulfamoyl-tetrazol-5-yl, 1-sulfamoylethyl-tetrazol-5-yl, 1-(2-N,N-dimethyl-sulfamoylethyl)-tetrazol-5-yl, 1-(3-sulfamoylpropyl)-tetrazol-5-yl, 1-(2-sulfo-1-methylethyl)-tetrazol-5-yl, 1-(4-sulfobutyl)-tetrazol-5-yl, 1-(2-carbamoylethyl)-tetrazol-5-yl, 1-(N-methylcarbamoylmethyl)-tetrazol-5-yl, 1-(N,N-dimethylcarbamoylmethyl)-tetrazol-5-yl, 1-(2-carbamoylpropyl)-tetrazol-5-yl, 1-(3-carboxypropyl)-tetrazol-5-yl, 1-(2-carboxy-1-methylethyl)-tetrazol-5-yl, 1-(4-dimethylaminophenyl)-tetrazol-5-yl, 1-acetamidoethyl-tetrazol-5-yl, 1-(2-hydroxyethyl)-tetrazol-5-yl, 1-ethoxycarbonylmethyl-tetrazol-5-yl, 1-(2-aminoethyl)-tetrazol-5-yl and 1-(3-methoxypropyl)-tetrazol-5-yl.

If in the definition of the radicals $R^8$ to $R^{21}$ substituents or references to particular ring systems occur which are not explained in more detail, they correspond to the preceding statements concerning the general substitution possibilities of the radical $R^5$ in the meaning of "heterocyclic radical". At the same time, they are illustrated further by the particular accompanying tabular summary of specific radicals.

Further examples of heterocyclic $R_5$ radicals which may be mentioned are: 1,2,3-thiadiazol-5-yl, 1,2,4-thiadiazol-3-yl, 1,2,5-thiadiazol-3-yl, 1,2,3-oxadiazol-5-yl, 4,5-dimethyl-oxazol-2-yl, 4-phenyl-oxazol-2-yl, benzoxazol-2-yl, oxazolin-2-yl, imidazol-2-yl, imidazolin-2-yl, benzimidazolin-2-yl, 1-methyl-imidazolin-2-yl, 2-furyl, 2-thiophenyl, 2-pyrrolyl, 2-thiazolinyl, 3-isoxazolyl, 3-pyrazolyl, thiatriazol-5-yl, purin-yl, pyrazinyl, 2-methylmercapto-6-phenyl-1,3,5-triazin-4-yl, 5-methyl-6-hydroxy-1,3,4-triazin-2-yl, 5-phenyl-4H-1,3,4-thiadiazin-2-yl, 5-hydroxy-4H-1,3,4-thiadiazin-2-yl, 3-hydroxy-tetrazol-[4,5-b]-pyridazin-6-yl and tetrazol-[4,5-b]-pyridazin-6-yl.

If $R^5$ represents the radical

the radicals $R^6$ and $R^7$, which can be identical or different, can have the following meanings: straight-chain or branched alkyl with 1–4 C atoms, such as, for example, methyl, ethyl, propyl, butyl or isobutyl, preferably methyl, straight-chain or branched alkenyl with 2–4 C atoms, such as, for example, allyl, straight-chain or branched alkoxy with 1–4 C atoms, such as, for example, methoxy, ethoxy, propoxy or isobutoxy, straight-chain or branched alkenyloxy with 1–4 C atoms, such as, for example, allyloxy, aryl, in particular phenyl, which can also be substituted, for example by alkyl or alkoxy with 1–4 C atoms, in particular methyl or methoxy, or by halogen, in particular chlorine, or a carbocyclic ring with 3–8 C atoms, such as, for example, cyclohexyl.

Examples which may be mentioned are, in particular:

(α) If Y denotes

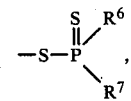

the radical of dimethyl-dithiophosphinic acid, butyl-methyl-dithiophosphinic acid, ethylmethyl-dithiophosphinic acid, isobutyl-methyl-dithiophosphinic acid, methyl-phenyl-dithiophosphinic acid, diphenyl-dithiophosphinic acid, O-methyl-methyl-dithiophosphonic acid, O-ethyl-methyl-dithiophosphonic acid, O-ethyl-ethyl-dithiophosphonic acid, O-ethyl-propyl-dithiophosphonic acid, O-methyl-(4-methoxyphenyl)-dithiophosphonic acid, O-methyl-isobutyl-dithiophosphonic acid, O-methyl-cyclohexyl-dithiophosphonic acid, O,O-dimethyl-dithiophosphoric acid, O,O-diethyl-dithiophosphoric acid and O,O-di-propyl-dithiophosphoric acid, and (β) if Y denotes

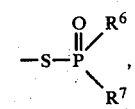

the radical of O-methyl-methyl-thiophosphonic acid, O-ethyl-methyl-thiophosphonic acid, isobutyl-methylthiophosphinic acid, O-ethyl-ethyl-thiophosphonic acid and O-ethyl-propyl-thiophosphonic acid.

The nomenclature of R. S. Cahn, Ch. ingold and V. Prelog, Angew. Chemie 78 (1966), page 413, is used for characterising the configuration of the SO group in the cephem ring. An SO group in the R configuration has an oxygen atom in the α-position and a SO group in the S configuration has an oxygen atom in the β-position. α and β are previous designations for asymmetric atoms and are customary, in particular, in the case of naturally occurring substances.

In order to obtain the compounds of the formula I with the $R_2O$ group in the syn-position, which in the present text is represented throughout as

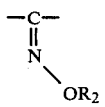

to differentiate from the anti-position

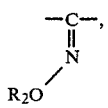

it is appropriate to ensure that the starting material of the general formula III is already present as the syn-compound. If the mild reaction conditions customary for reactions with syn-compounds are then adhered to, synend products are as a rule obtained. Nevertheless it can sometimes happen that a small amount of the corresponding anticompound is also obtained as an impurity in the end product, and, if desired, this can be separated by methods which are known in the laboratory, such as, for example, recrystallisation.

Lactams of the general formula II which can be employed according to the invention are described in Dutch Patent application No. 7,309,912. Possible starting materials are lactams of the formula XI

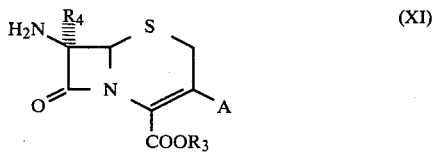

wherein A, $R_3$ and $R_4$ have the meanings indicated above. The lactams of the formula XI are known from the literature or can be manufactured according to information in the literature, for example according to the information in E. F. Flynn, Cephalosporins and Penicillins, Chemistry and Biology, Academic Press, New York and London, 1972, or German Offenlegungsschrift No. 2,359,402.

The lactams of the formula XI can preferably be oxidized in the form of the free acids or in the form of esters, but also in the form of salts. It is advantageous to protect the 7-amino group by amino-protective groups which can be easily split off, such as are customary, for example, in peptide chemistry. Examples of groups which may be used and can be split off under acid conditions are: tert.-butyl, benzhydryl, tert.-butoxycarbonyl, trityl, benzyloxycarbonyl, 3,5-dimethoxybenzyloxycarbonyl and trialkylsilyl, such as, for example, trimethylsilyl. Protection of the amino group in the form of a Schiff's base, which can be split under acid conditions, by reaction with reactive carbonyl compounds, such as, for example, benzaldehyde, salicylaldehyde, p-nitrobenzaldehyde, furfurol, 5-nitrofurfurol, acetylacetone or ethyl acetoacetate, has also proved suitable. The Schiff's base can also be split by reaction with hydrazine and its derivatives, preferably a Girard reagent, phenylhydrazine or 2,4-dinitrophenylhydrazine.

Examples of suitable methods for oxidizing the sulfur in the cephem ring are the methods which are known from the literature which lead to the formation of SO and $SO_2$ bonds by the oxidation of sulfides, such as are described, for example, by F. Korte in Methodicum Chimicum, volume 7 (1976), Hauptgruppenelemente und deren Verbindungen (Main Group Elements and their Compounds), pages 693–698, and the oxidizing agents mentioned in the Dutch application given above or in E. F. Flynn, Cephalosporins and Penicillins, Chemistry and Bilogy, Academic Press, New York and London, 1972, preferably photosensitized oxidation using oxygen, peroxides, hydroperoxides, peracids, singlet-oxygen, hydrogen peroxide and mixtures thereof with inorganic or organic, oxidation-resistant acids, such as, for example, phosphoric acid, formic acid, acetic acid and trifluoroacetic acid. The peracids can also be produced in situ by mixing the acids with hydrogen superoxide. 3-Chloroperbenzoic acid is advantageously employed direct.

Suitable solvents for the oxidation are all the solvents which are stable under the reaction conditions, such as, for example, dioxan, tetrahydrofuran, chloroform, methylene chloride, acetic acid, formic acid, trifluoroacetic acid, glycol dimethyl ether, benzene, chlorobenzene, tetramethylurea, dimethylformamide and dimethylacetamide.

The reaction conditions and the amount of oxidizing agent depend on the desired end product and on the substituents present on the cephem skeleton. 2 oxidation equivalents (corresponding to one active oxygen atom) or a slight excess are sufficient for the manufacture of the R and S sulfoxides. The oxidation to the sulfone requires at least 4 oxidation equivalents, an excess of oxidizing agent also being possible in order to accelerate the reaction.

The reaction temperatures can be between about −20° and +80° C., but the oxidation, above all in the case of the manufacture of the sulfoxides, is carried out at as low a temperature as possible, preferably −20° to +20° C.

Derivatives of the formula XI which are protected on the 7-amino group in the form of a Schiff's base are particularly suitable for the manufacture of the lactams of the formula II with the R configuration. Acyl amino-protective groups on the 7-amino group give predominantly 1-sulfoxides with the S configuration.

The separation and characterization of R and S sulfoxides is achieved on the basis of their different solubilities and their different migration rates in chromatographic separations. A further differentiation between the R and S sulfoxides is achieved with the aid of NMR spectroscopy (compare the literature by E. H. Flynn indicated above).

The amino-protective groups are split off under the conditions for the particular protective group, which are indicated in the literature. If $R_3$ is a group which is unstable towards acid, such as, for example, tert.-butyl, and if this is to be retained for secondary reactions, suitable amino-protective groups are, in particular, those which can be split off using hydrazine derivatives, thioureas or bases.

The carboxylic acids of the general formula III used, according to the invention, for acylating the lactams of the general formula II can be manufactured by various processes.

Thus, for example, compounds of the formula III in which R₁ denotes hydrogen and R₂ denotes acyl are obtained by reaction of thiourea with

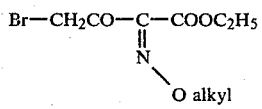

and subsequent saponification of the ester group, whereby the reaction should appropriately be effected with a stoichiometric amount of thiourea at room temperature in a water-containing solvent, such as, for example, acetone, and the reaction should not be carried out for longer than a few hours, for example a maximum of about 2–3 hours.

It is also possible to react the α-carbonyl group of a 2-aminothiazole-4-glyoxylic acid alkyl or aralkyl ester, substituted on the amino group by R₁, with a hydroxylamine compound of the general formula H₂N-OR₂ and then to saponify the resulting ester in a manner which is in itself known.

The manufacture of the aminothiazole-glyoxylic acid esters used for this reaction is described in German Patent application No. P 2,710,902.0. Most of the hydroxylamine derivatives required for the reaction are known, or they can be easily manufactured according to the information in the literature.

The reaction of the two components is carried out under the conditions, described in the literature, for the reaction of glyoxylic acid derivatives with hydroxylamine and its O-derivatives.

Compounds of the formula III in which R₁ represents an acyl group can be obtained easily and in high yields by acylating the compounds described above of the general formula

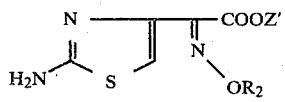

in which Z' represents lower alkyl or aralkyl, with reactive carboxylic acid derivatives.

It has proved favorable to use acid halides, in particular acid chlorides and acid bromides. However, it is particularly advantageous to employ symmetric or unsymmetric anhydrides. The acylation is carried out in the presence of bases, such as, for example, triethylamine, preferably at room temperature or, in particular, at temperatures which are lowered still further, in organic solvents which do not interfere with the reaction, in particular in halogenated hydrocarbons, such as, for example, methylene chloride, chloroform or tetrachloroethylene. The resulting esters are then converted into the free carboxylic acids.

If in the formula III R₁ in the meaning of acyl represents an aliphatic acyl radical which is also substituted by a nucleophilic radical defined under Y, such as, for example, a nitrogen- or oxygen-nucleophile, but in particular by the S-nucleophilic group R₅-S-, R₅ having the meaning indicated above, the acylation described above is appropriately carried out with activated α-halogenoalkyl acid derivatives, such as, for example, chloroacetyl chloride, α-bromopropionyl chloride or bromoacetyl bromide, which can also further carry a aryl, preferably phenyl, in the α-position, and the halogen is then reacted with a mercaptan of the formula HS-R₅ and thus replaced by —SR₅.

The replacement reaction is carried out in organic or inorganic solvents, preferably in water, in the presence of organic or inorganic bases, such as, for example, triethylamine or sodium bicarbonate, for example at temperatures between about 10° and 80° C., but in particular at room temperature.

If in the formula III the radical R₁ represents an arylsulfonyl or alkylsulfonyl group, these compounds of the formula III are obtained by reacting activated alkylsulfonic acid derivatives or arylsulfonic acid derivatives with compounds of the formula

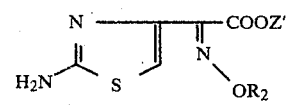

and then saponifying the product.

Possible activated sulfonic acid derivatives are, in particular, the sulfonic acid halides known from the literature, such as, for example, sulfonic acid chlorides, as well as the symmetric anhydrides.

The reaction is carried out in the presence of bases in organic solvents which do not interfere with the reaction. Suitable bases are, above all, organic bases, such as, for example, N,N-dimethylaniline or triethylamine. Examples of possible organic solvents which do not interfere with the reaction are halogenated hydrocarbons, such as, for example, methylene chloride or chloroform, or tertiary amides, such as, for example, dimethylformamide or dimethylacetamide. The reaction is appropriately carried out at room temperature.

If in the general formula III the radical R₁ represents a group which can be easily removed again, its introduction into the amino group can be effected in the manner known from peptide chemistry for amino-protective groups (compare the book mentioned below by Schröder and Lübke, The Peptides, volume 1 (1965), page 3). If such a group is, for example, triphenylmethyl, its introduction can be effected with triphenylchloromethane, the reaction appropriately being carried out in an organic solvent, such as, for example, halogenated hydrocarbons, in the presence of bases.

Chloroform and methylene chloride have proved particularly suitable halogenated hydrocarbons here. Bases which can be mentioned are, in particular, tertiary amines, such as, for example, triethylamine or N-methylmorpholine.

It is appropriate, not only in the manufacture of the carboxylic acid III which contans a group

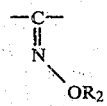

in the syn-position, but also in all other reactions, to use reaction conditions which are as mild and gentle as possible, such as are known to the expert, from the literature, for reactions with syn-compounds and β-lactams, such as, for example, no elevated temperatures, reaction times which are as short as possible, no substantial excesses of an acid reactant and the like, in order to avoid any possible flipping over of the oxime group into the anti-form and a splitting of the β-lactam ring.

The reactive derivatives of the carboxylic acids of the general formula III

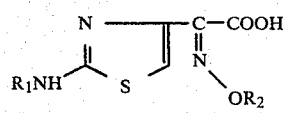

which are employed, according to the invention, for the acylation reaction (a) and which are capable of amide formation can be obtained from the carboxylic acids by processes which are known from the literature. Examples of reactive derivatives which may be mentioned are the activated esters, such as, for example, p-nitrophenyl esters or trichlorophenyl esters, azides or anhydrides. A preferred process for activating the carboxyl group consists in converting it into a symmetric anhydride. The processes for the manufacture of symmetric anhydrides are known from the literature and correspond to the methods generally used in peptide chemistry. For example, the inner anhydrides, which are subsequently reacted with the aminocephemcarboxylic acids of the formula II in organic solvents, are obtained from the carboxylic acids of the general formula III using condensing agents, such as, for example, N,N-disubstituted carbodiimides, such as, for example, dicyclohexylcarbodiimide.

The manufacture of the compounds of the general formula I by acylating compounds of the formula II with the carboxylic acids of the formula III can be carried out under variable experimental conditions, for example using various solvents. Examples of suitable solvents are organic solvents, such as, for example, halogenated hydrocarbons, for example methylene chloride or chloroform, but also water or mixtures of water and organic solvents, which are mixed intensively with water. In order to carry out the reaction well, it is appropriate to dissolve the aminolactam derivatives of the formula II.

If lactams of the general formula II in which $R_3$ represents one of the ester groups defined above are used, the reaction is preferably carried out in organic solvents, in which most of the esters are readily soluble. Examples of such solvents which may be mentioned are halogenated hydrocarbons, such as, for example, methylene chloride or chloroform, but also tertiary amides, such as, for example, dimethylformamide or dimethylacetamide.

The ester groups listed above under $R_3$ include on the one hand those such as, for example, are known from peptide chemistry as carboxyl-protective groups which can be easily split off (compare, for example, E. Schröder and K. Lübke, The Peptides, volume 1, Academic Press, New York and London, 1965, page 52). However, they preferably include ester groups, the use of which can be therapeutically advantageous in the administration of the end products. In this case also the restrictions can be somewhat flexible, since, for example, a benzhydryl ester is therapeutically usable and at the same time can also serve as a protective group.

If lactams of the general formula II in which $R_3$ represents hydrogen are used, the compounds must be dissolved, with the addition of bases.

Suitable bases which can be used for the solution are inorganic or organic bases. Thus, tertiary amines, such as triethylamine, N,N-dimethylaniline or N-methylmorpholine, have proved particularly suitable for the preparation of solutions in organic solvents, and alkali metal bicarbonates, such as sodium bicarbonate or potassium bicarbonate, and tertiary amines have proved particularly suitable for the preparation of aqueous solutions. In general, the bases are added in at least stoichiometric amount, relative to the desired reaction. An excess of base of, for example, about 0.1 to 2, in particular about 0.2 to 0.8, moles can be advantageous.

In the case of compounds of the formula II which are sensitive towards bases, depending on the course of the reaction, the pH can be kept constant at about 4 to 8, preferably 6 to 7, by continuously adding the base.

The aminolactam derivatives of the formula II can be dissolved in a wide temperature range. However, appropriately it should not exceed a temperature of about 40° C. In the case of derivatives which are sensitive towards bases, it is advisable, however, to choose a temperature range from about 0° to 15° C.

The activated derivatives of the carboxylic acids of the general formula III are added to the lactams of the formula II, which are present in solution or appropriately in suspension. The reaction is carried out in a manner which is in itself known. If water or mixtures of water and organic solvents are used as the reaction medium, it is advisable to maintain the temperature in a range from about −5° to +10° C. If organic solvents are used, it is also possible to carry out the acylation at temperatures up to about 65° C., preferably at room temperature.

In order to carry out the reaction better, the activated carboxylic acid derivatives of the formula III are taken up in a solvent which does not interfere with the reaction and are introduced in dilute form. If the acylation is carried out in an aqueous medium, it is possible to use, for example, anhydrous ketones, such as acetone or methyl ethyl ketone, or, with intensive stirring, ethers, such as, for example, diethyl ether or diisopropyl ether, as solvents for the activated carboxylic acid derivatives.

If the acylation is carried out in a non-aqueous medium, it is advisable to use the same solvent for diluting the acid derivatives as is used for the acylation.

In order to achieve higher yields, the activated acid derivatives of the formula III are employed in an at least stoichiometric amount. An excess of about 5–25% can prove appropriate.

Compounds of the formula I can also be obtained by interchanging the stages described above of oxidation of lactams of the formula XI to give the sulfoxide or sulfone of the formula II and acylation with carboxylic acids of the formula III. Thus, it is possible to first acylate the lactams of the formula XI, wherein A, $R_3$ and $R_4$ have the meaning indicated above, but $R_3$ cannot be hydrogen, with carboxylic acids of the formula III in which the radicals $R_1$ and $R_2$ have the abovementioned meaning, to give the cephem compounds of the formula IV. The acylation is carried out in the manner described for the reaction of compounds of the general formula II and III. The subsequent oxidation to the sulfoxide or sulfone of the general formula I can be carried out under the reaction conditions indicated for the oxidation of the lactams of the general formula XI to give the compounds of the formula II. Protection of the 7-amino group is thereby superfluous since, because of the preceding step of acylation with acids of the formula III, the 7-amino group is no longer attacked. The oxidation of compounds of the general formula IV predominantly gives sulfoxides with the S configuration, which may also contain R sulfoxides which can then be separated off in the manner described above.

Compounds of the formula IV in which A denotes —$CH_2Y$, wherein Y represents the radical of a S-nucleophilic or N-nucleophilic compound with the meanings indicated above, can be manufactured in a manner which is in itself known, for example by reacting compounds of the formula IV in which $R_3$ represents hydrogen or a cation and the radical A denotes, for example, —$CH_2$—$OCOCH_3$ or —$CH_2$— halogen with a compound containing a S-nucleophilic or N-nucelophilic radical, in particular with S-nucleophilic compounds of the formula $HSR_5$, hydrazoic acid as well as optionally substituted pyridine, quinoline or isoquinoline compounds.

The reaction can be carried out by reacting one mole of a compound of the formula IV, in which the radicals $R_1$, $R_2$ and $R_4$ have the meaning indicated above, $R_3$ represents hydrogen or a cation and A represents, for example, acetoxymethyl, with at least one mole of a compound containing the nucleophilic radical Y, in particular of the compounds mentioned above as preferred, in a solvent which does not interfere with the reaction.

An excess of the nucleophiles, in particular of the thiol, pyridine, quinoline or isoquinoline component, has an advantageous effect on the yield. Should small amounts of the corresponding anti-compound be obtained here, they can be removed in the customary manner, for example by recrystallization.

Examples of solvents which do not interfere with the reaction are water, acetone, chloroform, nitrobenzene, methylene chloride, ethylene chloride, dimethylformamide, methanol, ethanol, ether, tetrahydrofuran, dimethylsulfoxide or any other solvents which do not have an adverse effect on the reaction. Strongly polar solvents are favorable, preferably water. Of the solvents, the hydrophilic solvents, preferably acetone, methanol, ethanol, dimethylformamide and dimethylsulfoxide, can also be used in mixtures with water.

The reaction is carried out in a pH range from 5 to 8, preferably at the neutral pH value.

If the compound IV (in which $R_3$=hydrogen and A is, for example, acetoxymethyl or chloromethyl) or the nucleophilic compound, in particular HS—$R_5$, is used in the free form, the reaction is preferably carried out in the presence of a base, for example an inorganic base, such as an alkali metal hydroxide, alkali metal carbonate or alkali metal bicarbonate, such as, for example, sodium bicarbonate or potassium bicarbonate, an organic base, such as a trialkylamine, or a tertiary ammonium base. The compounds of the formula IV and the HS—$R_5$ can also be employed directly in the form of their salts, preferably the sodium or potassium salts.

The reaction temperature can be varied within a wide range. As a rule, the reaction is carried out at room temperature or the mixture is warmed up to the reflux temperature of the solvents or solvent mixtures used, but appropriately not above about 80° C.

Compounds of the formula IV in which $R_3$ represents hydrogen or a cation can be converted into an ester ($R_3$=an ester group) by reacting such an acid or salt of the formula IV with a compound of the formula $R_3$-B, wherein B represents a leaving group, such as, for example, halogen, for example chlorine, bromine or iodine, or a methylsulfonyloxy or tosyloxy group, in a manner which is in itself known in a pH range from 5-8, preferably at the neutral pH value.

The isolation of the compounds of the formula I from the reaction medium can be effected by methods which are in themselves known, which depend on the solubility of the resulting compounds, and in general leads to amorphous or crystalline end products.

Thus, for example, the reaction products can be taken up in water or organic solvents, if appropriate after concentrating or evaporating the solution, and after appropriate purification operations, such as, for example, filtration, trituration or centrifugation, can be precipitated in the form of the free carboxylic acids ($R_3$=hydrogen) by adding mineral acids, appropriately in an approximately stoichiometric amount, to the clarified reaction mixture. Suitable mineral acids are, in particular, dilute acids, such as dilute hydrochloric acid or sulfuric acid. It is also possible to use very low-molecular weight organic acids, such as, for example, formic acid or trifluoroacetic acid, or also arylsulfonic acids, such as, for example, toluenesulfonic acids or naphthalenesulfonic acids. Lyophilization of the solution can occasionally also be appropriate.

If symmetric anhydrides of the carboxylic acids of the formula III have been used as the starting component, the carboxylic acid constituent liberated during the acylation must be separated by customary experimental methods, which depend, for example, on its solubility, crystallinity or ease of extraction.

If desired, protective groups which have been introduced for intermediate protection of the amino group of the aminothiazole radical can be removed by processes which are known from the literature, such as are described, for example, for peptide chemistry. For example, if $R_1$ represents a triphenylmethyl group, the splitting off is effected in an acid medium. Mixtures of formic acid and water, in particular mixtures of water and formic acid in the ratio 1:1 to 4:1, have proved suitable.

The compounds of the formula I containing a free amino and carboxyl group can be isolated by known experimetal methods, for example in the case where a triphenylmethyl group is split off as triphenylcarbinol, by filtering off the triphenylcarbinol and then concentrating the solution.

Esters obtained in the reaction according to the invention, the ester group of which has a protective group for the carboxyl group, such as, for example, p-methoxybenzyl, p-nitrobenzyl or tert.-butyl esters, can, if desired, also be converted into the free carboxylic acids of the formula I in a manner which is known from the literature. However, as already mentioned, it is also possible to retain for therapeutic use ester groups which also serve as carboxyl-protective groups, such as, for example, benzhydryl esters.

Compounds of formula I having a free α-oxime group ($R_2$=hydrogen) can be prepared by the process of the invention, for example by exchange of Y in the definition of acetoxy and X=S in compounds of formula I in which $R_2$ denotes hydrogen with subsequent oxidation to obtain the sulfoxide X=SO), or by splitting off a group $R_2$ having the character of a protective group from compounds of formula I in known manner by acid hydrolysis or hydrogenolysis, groups of this type being, for example tert.butyloxycarbonyl, dibenzyl, carbobenzyloxy, formyl, trichloroethoxycarbonyl, 2-tetrahydropyranyl, preferably triphenylmethyl.

For acid hydrolysis there may be used, for example, formic acid, triflucoracetic acid or acetic acid, which can be used either in anhydrous form or in aqueous solutions.

Preferred agents for acid hydrolysis are anhydrous trifluoroacetic acid, aqueous formic acid or acetic acid if tert. butoxycarbonyl or triphenylmethyl shall be split off. Dibenzyl or carbobenzyloxy, for example, are preferably split off by catalytic hydrogenation agents.

If $R_2$ denotes chloroacetyl, this may be split off also with thiourea, preferably in a neutral or acid medium (cf. JACS 90 (1968), page 4508).

Simultaneously with $R_2$, a radical $R_1$ denoting a protective group can be split off by acid hydrolysis, hydrogenolysis or with thiourea. It is the same with the radical $R_3$ provided it can be eliminated by hydrolysis or hydrogenolysis. In the case of compounds containing radicals $R_1$, $R_2$ and $R_3$ having the function of protective groups which can be split off in different manner only, for example by hydrolysis and hydrogenolysis or with different hydrolysis agents, these methods should be applied successively.

The resulting acids of the formula I can be converted into their physiologically acceptable salts, in particular into alkali metal salts, such as, for example, the sodium salts, or into salts with organic bases, preferably tertiary amines, such as, for example, the procaine salt.

The conversion into salts can be effected in a manner which is in itself known by reacting a carboxylic acid of the general formula I with the desired base, for example with sodium bicarbonate, or the sodium salts of organic carboxylic acids, such as, for example, sodium acetate, sodium propionate, sodium hexanoate or sodium 2-ethyl-hexanoate, or potassium acetate.

It is also possible to isolate salts directly from the reaction solution, for example by precipitation with suitable organic solvents or by lyophilization.

Compounds of the formula I in which $R_3$ represents an ester group, in particular a physiologically acceptable ester, can be obtained directly by using the appropriately esterified starting material of the formula II, or they can be obtained by subsequent esterification of compounds of the formula I in which the carboxyl group is present in the free form or as a salt, by processes which are known from the literature. Because it is easier to carry out, subsequent esterification can be advantageous for the manufacture of physiologically acceptable esters and a variation of the ester group.

For example, esters are obtained by subsequent reaction when the salts, preferably the triethylammonium salts or the alkali metal salts, preferably the sodium salts, are reacted with reactive halogenoalkyl compounds, such as, for example, chloroalkyl, bromoalkyl or iodoalkyl compounds, or trialkylammoniumalkyl compounds, in particular the corresponding chloromethyl, bromomethyl, iodoethyl or triethylammoniummethyl compounds. Examples of reactive halogenoalkyl compounds which can be used are halogenomethoxycarbonyl compounds, such as chloromethyl acetate, chloromethyl propionate or chloromethyl pivalate, or the ω-halogenomethyl ketones, such as, for example, ω-bromoacetophenone, chloroacetone or ω-bromoacetophenone substituted in the aryl nucleus, such as, for example, in the phenyl nucleus, such as, for example, ´5-sulfamyl-4-chloro-ω-bromoacetophenone, but also halogenoalkyl-carboxylic acid derivatives, in particular the halogenomethyl-carboxylic acid derivatives, such as chloroacetic acid, bromoacetic acid and bromoacetic acid esters, such as, for example, the low-molecular alkyl esters and optionally the benzyl esters, such as the p-methoxybenzyl ester. Halogenomethyl ketones in which the 2-alkyl group is monosubstituted or polysubstituted by alkoxycarbonyl, oximino, oxido or alkoximino radicals, such as, for example, 1-chloro-(3-methoxyimino-3-carbethoxy)-acetone or 1-bromo-3-methoxyimino-3-carbethoxyacetone, but also bromo-3-oxido-3-carbethoxyacetone, have proved suitable reactive halogenomethyl derivatives.

Further reactive halogenoalkyl derivatives which may be mentioned are the alkyl iodides, such as, for example methyl iodide, ethyl iodide or isopropyl iodide, and the corresponding bromides.

The reaction with diazoalkanes, such as, for example, diazomethane or diazoethane, but also diarylmethyldiazomethane, such as, for example, diphenyldiazomethane, may furthermore be mentioned for the manufacture of optionally substituted esters.

A further esterification method consists in reacting the alkali metal salts, preferably in alcohol, such as, for example, methanol, with alkyl sulfochlorides, such as, for example, methyl sulfochloride.

The reaction of the salts of the cephem compounds of the formula I with alkyl halides is appropriately carried out in a solvent which does not interfere with the reaction, such as, for example, dimethylformamide or dimethylacetamide, or also dimethylsulfoxide. The reaction can be carried out within a wide temperature range, for example at 0° to 80° C., but preferably at 30°–50° C., depending on the activity of the halogenoalkane.

In order to achieve good yields, the halogenoalkane is employed in an at least equimolar amount. An excess of up to 5 equivalents has sometimes proved favorable.

Depending on the desired end product, the process steps (α) to (δ) which are possible according to the invention can be combined with one another, it frequently being possible to rearrange the sequence. These rearrangement possibilities of the reaction steps, which are self-evident to any expert, also belong to the subject of the invention.

If $R_4$ is present in the form of one of the groups described above which can be converted into lower alkoxy, preferably methoxy, this conversion can be carried out in a manner which is known from the literature (compare, for example, German Offenlegungsschrift No. 2,440,790).

The compounds of the general formula I according to the invention are valuable chemotherapeutic agents which possess a very powerful antimicrobial action against Gram-positive and Gram-negative bacteria, have an unexpectedly good action against penicillinase-forming Staphylococci and in some cases also have a fungistatic activity. The high activity of the sulfoxides with the S configuration must be regarded as particularly surprising.

The compounds of the general formula I are distinguished, for example, by a considerable antimicrobial activity against a number of bacteria against which the known cephalosporins are scarcely active.

Since the compounds of the formula I furthermore exhibit favorable toxicological and pharmacokinetic properties, they are valuable antimicrobial active compounds for the treatment of infectious diseases.

The invention thus also relates to medicinal formulations for the treatment of microbial infections, which are characterized in that they contain one or more of the compounds according to the invention.

The products according to the invention can also be used in combination with other active compounds, for example from the series of penicillins, aminoglycosides, cephalosporins or compounds which influence the systematics of bacterial infections, such as, for example, antipyretic agents, analgesic agents or antiphlogistic agents.

The compounds of the general formula I can be administered orally, intramuscularly or intravenously.

Medicinal formulations which contain on or more compounds of the general formula I as the active compound can be prepared by mixing the compound(s) of the general formula I with one or more pharmacologically acceptable excipients or diluents, such as, for example, fillers, emulsifiers, lubricants, flavor-correcting agents, dyestuffs or buffer substances, and converting the mixture into a suitable galenic formulation form, such as, for example, tablets, dragees, capsules or a solution or suspension suitable for parenteral administration. Examples of excipients or diluents which may be mentioned are tragacanth, lactose, talc, agar-agar, polyglycols, ethanol and water. Suspensions or solutions in water can preferably be used for parenteral administration. It is also possible to administer the active compounds as such, without excipients or diluents, in a suitable form, for example in capsules.

Suitable doses of the compounds of the general formula I are about 0.4 to 20 g/day, preferably 0.5 to 4 g/day, for an adult having a body weight of about 60 kg. Individual doses or, in general, multiple doses may be administered, it being possible for the individual dose to contain the active compound in an amount of about 50 to 1,000 mg, preferably 100 to 500 mg.

In addition to the compounds described in the embodiment examples, it is also possible, for example, to manufacture according to the invention the following compounds given in the table, the substituents $R_1$, $R_2$, $R_3$, $R_4$ and A indicated for the particular compound relating to the basic structure of the general formula XII

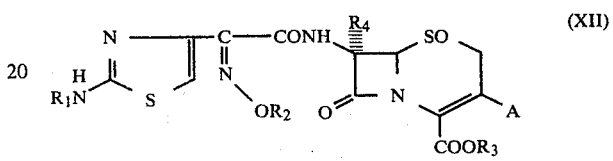

in which the group —$OR_2$ is in the syn-position and SO is in the R or S configuration.

| $R_1$ | $R_2$ | $R_3$ | $R_4$ | A |
|---|---|---|---|---|
| H | H | H | H | $CH_3$ |
| H | H | H | H | $-CH_2OCOCH_3$ |
| H | H | H | $-OCH_3$ | $-CH_2OCOCH_3$ |
| H | H | H | H | $-CH_2OH$ |
| H | H | H | H | $-CH_2OCOC_2H_5$ |
| H | H | H | H | $-CH_2OCOC_4H_9$ |
| H | H | H | H | $-CH_2OCONH_2$ |
| H | H | H | H | $-CH_2OCONHCH_3$ |
| H | H | H | H | $-CH_2SCOCH_3$ |
| H | H | H | H | $-CH_2SCOC_2H_5$ |
| H | H | H | H | $-CH_2SCOCH(CH_3)_2$ |
| H | H | H | $-OCH_3$ | $-CH_2-SCOCH_3$ |
| H | H | H | H | $-Cl$ |
| H | H | H | H | $-OCH_3$ |
| H | H | H | H | $-CH_2Cl$ |
| H | H | H | H | $-CH_2F$ |
| H | H | H | H | $-OC_4H_9$ |
| H | $-CH_3$ | H | $-OCH_3$ | $-CH_3$ |
| H | $-CH_3$ | H | $-OCH_3$ | $-CH_2OH$ |
| H | $-CH_3$ | H | $-OCH_3$ | $-CH_2OCOCH_3$ |
| H | $-CH_3$ | H | H | $-CH_2OCOC_2H_5$ |
| H | $-CH_3$ | H | H | $-CH_2OCOC_4H_9$ |
| H | $-CH_3$ | H | H | $-CH_2OCONH_2$ |
| H | $-CH_3$ | H | H | $-CH_2OCONHC_2H_5$ |
| H | $-CH_3$ | H | H | $-CH_2SCOCH_3$ |
| H | $-CH_3$ | H | H | $-CH_2SCOC_2H_5$ |
| H | $-CH_3$ | H | H | $-CH_2-S-CO-\phantom{}$⟨C₆H₅⟩ |
| H | $-CH_3$ | H | H | $-CH_2SCO-CH_2C_6H_5$ |
| H | $-CH_3$ | H | H | $-CH_2S-CO-$⟨thienyl⟩ |
| H | $-CH_3$ | H | H | $-CH_2S-CO-$⟨pyridyl⟩ |
| H | $-CH_3$ | H | H | $-CH_2S-CO-$⟨thiazolyl⟩ |

-continued

| R₁ | R₂ | R₃ | R₄ | A |
|---|---|---|---|---|
| H | —CH₃ | H | H | —Cl |
| H | —CH₃ | H | H | —OCH₃ |
| H | —CH₃ | H | H | —CH₂Cl |
| H | —CH₃ | H | H | —O—C₄H₉ |
| H | —CH₃ | H | OCH₃ | —OCH₃ |
| H | —CH₃ | —CH₃ | H | —CH₂OCOCH₃ |
| H | —CH₃ | —C₄H₉ | H | —CH₂OCOCH₃ |
| H | —CH₃ | —CH₂CH=CH₂ | H | —CH₂OCOCH₃ |
| H | —CH₃ | —C(C₂H₅)(CH₃)(CH₃) | H | —CH₂OCOCH₃ |
| H | —CH₃ | —C₈H₁₇ | H | —CH₂OCOCH₃ |
| H | —CH₃ | —C₁₂H₂₅ | H | —CH₂OCOCH₃ |
| H | —CH₃ | —CH₂C≡CH | H | —CH₂OCOCH₃ |
| H | —CH₃ | —CH₂CCl₃ | H | —CH₂OCOCH₃ |
| H | —CH₃ | —CH₂C₆H₅ | H | —CH₂OCOCH₃ |
| H | —CH₃ | —CH₂-(3,5-di-OCH₃-C₆H₃) | H | —CH₂OCOCH₃ |
| H | —CH₃ | —CH₂-(4-NO₂-C₆H₄) | H | —CH₂OCOCH₃ |
| H | —CH₃ | —CH₂-(2-thienyl) | H | —CH₂OCOCH₃ |
| H | —CH₃ | —CH(C₆H₅)₂ | H | —CH₂OCOCH₃ |
| H | —CH₃ | —CH₂-(2-thiazolyl) | H | —CH₂OCOCH₃ |
| H | —CH₃ | —CH₂CO₂H | H | —CH₂OCOCH₃ |
| H | —CH₃ | —CH₂—CO₂C₂H₅ | H | —CH₂OCOCH₃ |

-continued

| R₁ | R₂ | R₃ | R₄ | A |
|---|---|---|---|---|
| H | —CH₃ | —CH₂—CO₂C(CH₃)₃ | H | —CH₂OCOCH₃ |
| H | —CH₃ | —CH₂CO₂—C₆H₅ | H | —CH₂COCH₃ |
| H | —CH₃ | —CH₂CONH₂ | H | —CH₂OCOCH₃ |
| H | —CH₃ | —CH₂CONHCH₃ | H | —CH₂OCOCH₃ |
| H | —CH₃ | —CH₂CONHC₄H₉ | H | —CH₂OCOCH₃ |
| H | —CH₃ | —CH₂CON(C₂H₅)₂ | H | —CH₂COCH₃ |
| H | —CH₃ | —CH₂OCOCH₃ | H | —CH₂OCOCH₃ |
| H | —CH₃ | —CH₂OCOC(CH₃)₃ | H | —CH₂OCOCH₃ |
| H | —CH₃ | —CH₂COC₆H₅ | H | —CH₂OCOCH₃ |
| H | —CH₃ | —CH₂—OCOC₆H₅ | H | —CH₂OCOCH₃ |
| H | —CH₃ | —CH₂CO– (thiophene) | H | —CH₂OCOCH₃ |
| H | —CH₃ | —CH₂CO–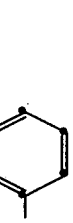 (pyridine) | H | —CH₂OCOCH₃ |
| H | —CH₃ |  (indane) | H | —CH₂OCOCH₃ |

-continued

| R₁ | R₂ | R₃ | R₄ | A |
|---|---|---|---|---|
| H | —CH₃ |  | H | —CH₂OCOCH₃ |
| H | —CH₃ |  | H | —CH₂SCOCH₃ |
| H | —CH₃ | —CH₂OCOC(CH₃)₃ | H | —CH₂SCOCH₃ |
| H | —CH₃ | —Si(CH₃)₃ | H | —CH₂OCOCH₃ |
| H | —CH₃ | —CH₂OCOC(CH₃)₃ | H | —Cl |
| H | —CH₃ | —CH₂OCOC(CH₃)₃ | H | —OCH₃ |
| H | —CH₃ | —CH₂OCOC(CH₃)₃ | OCH₃ | CH₂—O—CONH₂ |
| H | —C₂H₅ | H | H | —CH₂OCOCH₃ |
| H | —C₂H₅ | H | H | —CH₂OCOC(CH₃)₃ |
| H | —C₂H₅ | H | H | —CH₂OH |
| H | —C₂H₅ | H | H | —CH₂—OCONH₂ |
| H | —C₂H₅ | H | H | —CH₂OCONH—CH(CH₃)₂ |
| H | —C₂H₅ | H | H | —CH₂—SCOCH₃ |
| H | —C₂H₅ | H | H | —CH₂—SCOC₄H₉ |
| H | —C₂H₅ | H | H | —Cl |
| H | —C₂H₅ | H | H | —OCH₃ |
| H | —C₂H₅ | H | H | 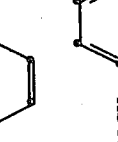—CH₂—SCO |
| H | —C₂H₅ | H | H | —CH₂—S—COCH₂ |
| H | —C₂H₅ | H | H | —CH₃ |

-continued

| R₁ | R₂ | R₃ | R₄ | A |
|---|---|---|---|---|
| H | —C₂H₅ | —C(CH₃)₃ | H | —CH₂OCOCH₃ |
| H | —C₂H₅ | —CH(C₆H₅)₂ | H | —CH₂OCOCH₃ |
| H | —C₂H₅ | —CH₂OCOC(CH₃)₃ | H | —CH₂OCOCH₃ |
| H | —C₂H₅ | indanyl | H | —CH₂OCOCH₃ |
| H | —C₂H₅ | 4-NO₂-benzyl | H | —CH₂OCOCH₃ |
| H | —C₂H₅ | —CH₂—CO₂H | H | —CH₂OCOCH₃ |
| H | —C₂H₅ | —CH₂CCl₃ | H | —CH₃ |
| H | —n-C₃H₇ | —H | —OCH₃ | —OCH₃ |
| H | —n-C₃H₇ | —H | H | —OCH₃ |
| H | —n-C₃H₇ | H | H | —Cl |
| H | —n-C₃H₇ | H | H | —CH₂—SCOCH₃ |
| H | —n-C₃H₇ | H | H | —CH₂—O—CONH₂ |
| H | —n-C₃H₇ | H | H | —CH₂SCOCH₂—C₆H₅ |
| H | —n-C₃H₇ | —C(CH₃)₃ | H | —CH₂OCOCH₃ |
| H | —n-C₃H₇ | indanyl | H | —CH₂SCOC₄H₉ |
| H | —n-C₃H₇ | —CH₂OCOC(CH₃)₃ | H | —CH₂OCOCH₃ |
| H | —i-C₃H₇ | H | —OCH₃ | —CH₂OCOCH₃ |
| H | —i-C₃H₇ | H | H | —CH₂OH |
| H | —i-C₃H₇ | H | H | —Cl |
| H | —i-C₃H₇ | H | H | —OCH₃ |
| H | —i-C₃H₇ | H | H | —CH₂OCONH₂ |
| H | —i-C₃H₇ | H | H | —CH₂SCOCH₃ |

-continued

| R₁ | R₂ | R₃ | R₄ | A |
|---|---|---|---|---|
| H | —i-C₃H₇ | —C(CH₃)₃ | H | —CH₂OCOCH₃ |
| H | —i-C₃H₇ | —CH₂OCOC(CH₃)₃ | H | —CH₂OCOCH₃ |
| H | —n-C₄H₉ | H | —OCH₃ | —CH₂OCOCH₃ |
| H | —n-C₄H₉ | H | H | —CH₂SCOCH₃ |
| H | —n-C₄H₉ | H | H | —CH₂OCONH₂ |
| H | —n-C₄H₉ | H | H | —CH₂OH |
| H | —n-C₄H₉ | H | H | —Cl |
| H | —n-C₄H₉ | H | H | —OCH₃ |
| H | —n-C₄H₉ | H | H | —CH₂Cl |
| H | —n-C₄H₉ | H | H | —O—CH₂—CH₂OCH₃ |
| H | —n-C₄H₉ | H | H | —O—CH₂—CH=CH₂ |
| H | —n-C₄H₉ | H | H | —O—(CH₂)₂O—n-C₄H₉ |
| H | —i-C₄H₉ | H | H | —CH₂OCOCH₃ |
| H | —i-C₄H₉ | H | H | —C₂SCOCH₃ |
| H | —CH₂—CH=CH₂ | H | H | —CH₂OH |
| H | —CH₂—CH=CH₂ | H | H | —CH₂OCOCH₃ |
| H | —CH₂—CH=CH₂ | H | —OCH₃ | —CH₂SCOCH₃ |
| H | —CH₂—CH=CH₂ | H | —OCH₃ | —CH₂OCOCH₃ |
| H | —CH₂—CH=CH₂ | H | H | —CH₂—SCOCH₃ |
| H | —CH₂—CH=CH₂ | H | H | —CH₂OCONH₂ |
| H | —CH₂—CH=CH₂ | H | H | —Cl |
| H | —CH₂—CH=CH₂ | H | H | —OCH₃ |
| H | —CH₂—CH=CH₂—CH₃ | H | H | —CH₂Cl |
| H | —CH₂—CH=CH—CH₃ | H | H | —CH₂OH |
| H | —CH₂—C≡CH | H | H | —CH₂OCOCH₃ |
| H | —CH₂CO₂CH₃ | H | H | —CH₂OCOCH₃ |
| H | —CH₂CO₂CH₃ | H | H | —CH₂OH |
| H | —CH₂CO₂CH₃ | H | H | —CH₃ |
| H | —CH₂CO₂CH₃ | H | H | —CH₂OCH₃ |
| H | —CH₂CO₂CH₃ | H | H | —OCH₃ |
| H | —CH₂CO₂C₂H₅ | H | H | —Cl |
| H | —CH₂—CO₂C₂H₅ | H | H | —CH₂—OCOCH₃ |
| H | CH₃ —CH—CO₂C₂H₅ | H | H | —CH₃ |
| H | C₂H₅ —CH—CO₂C₂H₅ | H | H | —CH₂OCOCH₃ |
| H | —CH₂CO₂C(CH₃)₃ | H | H | —CH₂OCOCH₃ |
| H | 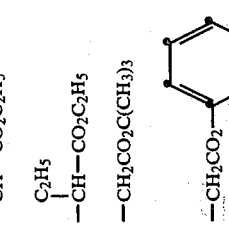 —CH₂CO₂— | H | H | —CH₂OCOCH₃ |
| H | —CH₂CO₂H | H | H | —CH₂OCOCH₃ |
| H | —CH₂CO₂H | H | —OCH₃ | —CH₂OCOCH₃ |

-continued

| R₁ | R₂ | R₃ | R₄ | A |
|---|---|---|---|---|
| H | —CH₂CO₂H | H | H | —CH₃ |
| H | —CH₂CO₂H | H | H | —CH₂OH |
| H | —CH₂CO₂H | H | H | —CH₂SCOCH₃ |
| H | —CH₂CO₂H | H | H | —CH₂OCONH₂ |
| H | —CH₂CO₂H | H | H | —CH₂Cl |
| H | —CH₂CO₂H | H | H | —OCH₃ |
| H | —CH₂CO₂H | H | —OCH₃ | —Cl |
| H | $\overset{CH_3}{-CH-CO_2H}$ | H | H | —CH₂OCOCH₃ |
| H | $\overset{C_2H_5}{-CH-CO_2H}$ | H | H | —CH₂OCOCH₃ |
| H | —CH₂—CH₂CO₂H | H | H | —CH₂OCOCH₃ |
| H | —CH₂CONH₂ | H | H | —CH₂OCOCH₃ |
| H | —CH₂CONHCH₃ | H | H | —CH₂OCOCH₃ |
| H | —CH₂CONH—$\overset{OH}{\underset{CH_2}{CH_2}}$—CH₂ | H | H | —CH₂OCOCH₃ |
| H | —CH₂CONHC₄H₉ | H | H | —CH₂OCOCH₃ |
| H | —CH₂CON⟨ ⟩ (pyrrolidine ring) | H | H | —CH₂OCOCH₃ |
| H | —CH₂CON⟨ ⟩O (morpholine ring) | H | H | —CH₂OCOCH₃ |
| H | —CH₂SO₂NH₂ | H | H | —CH₂OCOCH₃ |
| H | —CH₂SO₃H | H | H | —CH₂OCOCH₃ |
| H | —CH₂CH₂OH | H | H | —CH₂SCOCH₃ |
| H | —CH₂CH₂OCH₃ | H | H | —CH₂OCOCH₃ |
| H | —CH₂—OCOCH₃ | H | H | —CH₂OCOCH₃ |
| H | —CH₂—CH₂SO₃C₂H₅ | H | H | —CH₂OCOCH₃ |
| H | —CH₂—C₆H₅ | H | H | —CH₂OCOCH₃ |

-continued

| R₁ | R₂ | R₃ | R₄ | A |
|---|---|---|---|---|
| H | -CH₂-C₆H₄-Cl (4-Cl) | H | H | -CH₂OCOCH₃ |
| H | -CH₂-C₆H₄-OCH₃ (4-OCH₃) | H | H | -CH₂OCOCH₃ |
| H | -CH₂-C₆H₄- | H | OCH₃ | -CH₂OCOCH₃ |
| H | -CH₂-C₆H₄-CH₃ | H | H | -CH₂SCO-C₆H₄-CH₃ |
| H | cyclopentyl-CH(-CO₂H)- | H | H | -CH₂OCOCH₃ |
| H | cyclohexyl-CH(-CO₂H)- | H | H | -CH₂OCOCH₃ |
| H | cyclopropyl-CH(-CO₂H)- | H | H | -CH₂OCOCH₃ |

-continued
| R₁ | R₂ | R₃ | R₄ | A |
|---|---|---|---|---|
| H |  —CH—CO₂H | H | H | —CH₂OCOCH₃ |
| H |  —CO₂H | H | H | —CH₂OCOCH₃ |
| H |  —CO₂H | H | H | —CH₂OCOCH₃ |
| H |  —CO₂H | H | H | —CH₂OCOCH₃ |
| H |  —CO₂H | H | H | —CH₂OCOCH₃ |
| H |  —CH₂— | H | H | —CH₂OCOCH₃ |
| H |  —CH₂— | H | H | —CH₂OCOCH₃ |
| H |  —CH₂— (NO₂) | H | H | —CH₂OCOCH₃ |
| H | —CH=O | H | H | —CH₂OCOCH₃ |
| H | —COCH₃ | H | H | —CH₂OCOCH₃ |

-continued

| R₁ | R₂ | R₃ | R₄ | A |
|---|---|---|---|---|
| H | —COCH₂Cl | H | H | —CH₂Cl |
| H | —COCHCl₂ | H | H | —CH₂SCOCH₃ |
| H | —COCH₂N(CH₃)₂ | H | H | —CH₂OCOCH₃ |
| H | —COCH₂N⟨pyrrolidine⟩ | H | H | —CH₂OCOCH₃ |
| H | —SO₂—CH₃ | H | H | —CH₂OCOCH₃ |
| H | —SO₂—C₆H₄—CH₃ | H | H | —CH₂OCOCH₃ |
| H | —SO₂—C₆H₅ | H | OCH₃ | Cl |
| H | —CO—C₆H₅ | H | H | —CH₂OCOCH₃ |
| H | —CO—(2-thienyl) | H | H | —CH₂OCOCH₃ |
| H | —CO—(pyridyl) | H | H | —CH₂OCOCH₃ |
| H | —CH₂—CH=CH—CO₂H | H | H | —CH₂OCOCH₃ |

-continued

| $R_1$ | $R_2$ | $R_3$ | $R_4$ | A |
|---|---|---|---|---|
| H | H | H | H | $-CH_2-S\underset{N}{\overset{N=N}{\diagdown}}\!\!\!\diagup\!\!\!N\!\!-\!\!CH_3$ |
| H | $-C_2H_5$ | H | H | $-CH_2-S\underset{N}{\overset{N=N}{\diagdown}}\!\!\!\diagup\!\!\!N\!\!-\!\!CH_3$ |
| H | $-CH_3$ | H | H | $-CH_2-S\underset{N}{\overset{N=N}{\diagdown}}\!\!\!\diagup\!\!\!N\!\!-\!\!C_2H_5$ |
| H | $-CH_3$ | H | H | $-CH_2-S\underset{N}{\overset{N=N}{\diagdown}}\!\!\!\diagup\!\!\!N\!\!-\!\!CH_2CO_2H$ |
| H | $-CH_3$ | H | $OCH_3$ | $-CH_2S\underset{N}{\overset{N=N}{\diagdown}}\!\!\!\diagup\!\!\!N\!\!-\!\!CH_3$ |
| H | $-CH_2CO_2H$ | H | H | $-CH_2S\underset{N}{\overset{N=N}{\diagdown}}\!\!\!\diagup\!\!\!N\!\!-\!\!CH_2CO_2H$ |
| H | $-CH_3$ | H | H | $-CH_2S\underset{N}{\overset{N=N}{\diagdown}}\!\!\!\diagup\!\!\!N\!\!-\!\!CH_2-SO_3H$ |

-continued

| R$_1$ | R$_2$ | R$_3$ | R$_4$ | A |
|---|---|---|---|---|
| H | —nC$_4$H$_9$ | H | H | —CH$_2$—S—C(=N-N=N)—N—CH$_2$CO$_2$C$_2$H$_5$ |
| H | —CH$_2$—CH=CH$_2$ | H | H | —CH$_2$S—C(=N-N=N)—N—CH$_2$CH=CH$_2$ |
| H | —CH$_3$ | H | H | —CH$_2$S—C(=N-N=N)—N—CH$_2$SO$_2$NH$_2$ |
| H | —CH$_3$ | H | H | —CH$_2$S—C(=N-N=N)—N—C$_6$H$_5$ |
| H | —CH$_2$—C$_6$H$_5$ | H | H | —CH$_2$S—C(=N-N=N)—N—CH$_2$—C$_6$H$_5$ |
| H | —C$_2$H$_5$ | H | H | —CH$_2$S—C(=N-N=N)—N—CH$_2$CONH$_2$ |

-continued
| R₁ | R₂ | R₃ | R₄ | A |
|---|---|---|---|---|
| H | H | H | H |  |
| H | −HC(CH₃)(CH₃) | H | H |  |
| H | −CH₃ | H | H |  |
| H | −CH₃ | H | H |  |
| H | −CH₃ | H | H | 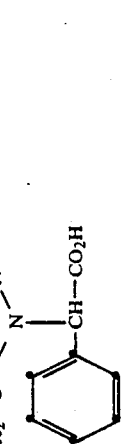 |

-continued

| R₁ | R₂ | R₃ | R₄ | A |
|---|---|---|---|---|
| H | —CH₃ | —CH₂OCO(CH₃)₃ | H | ![structure: -CH₂-S-C(=N-N=N)-N(CH₃)] |
| H | —CH₃ | (indane-type bicyclic structure) | H | ![structure: -CH₂-S-C(=N-N=N)-N(CH₃)] |
| H | —CH₃ | (phthalide-type bicyclic structure with C=O, O) | H | ![structure: -CH₂S-C(=N-N=N)-N(C₆H₅)] |
| HCO— | H | | H | —CH₂OCOCH₃ |
| —COCH₃ | H | | H | —CH₂OCOCH₃ |
| —COCH₂Cl | —CH₃ | H | H | —CH₂OCOCH₃ |
| —COCH₂Br | —CH₃ | H | H | —CH₂OCOCH₃ |
| —nC₄H₈CO— | —CH₃ | H | —OCH₃ | —CH₂OCOCH₃ |
| —COCCl₃ | —CH₃ | H | H | —CH₂OCOCH₃ |
| —CO—CH₂—C₆H₅ | —CH₃ | H | H | —CH₂OCOCH₃ |
| —CO—CH₂—C₆H₄Cl | —CH₃ | H | H | —CH₂OCOCH₃ |
| —COO—CH₂—C₆H₅ | —CH₃ | H | H | —CH₂SCOCH₃ |

-continued

| R₁ | R₂ | R₃ | R₄ | A |
|---|---|---|---|---|
| —CO—C₆H₅ | H | H | H | —CH₂OCOCH₃ |
| thiazoline-CO- | —CH₃ | H | H | —CH₂OCOCH₃ |
| oxazoline-CO- | —CH₃ | H | H | —CH₂OCOCH₃ |
| —COCH₂—C₆H₅ | —C₂H₅ | H | H | —CH₂Cl |
| —CO—CH(C₆H₅)₂ | —CH₃ | H | H | —CH₂OCOCH₃ |
| —COCH(CH₃)—C₆H₅ | —CH₃ | H | H | —CH₂OCOCH₃ |
| —COO—C(CH₃)₃ | —CH₃ | H | H | —CH₂OCOCH₃ |
| —C(C₆H₅)₃ | —CH₂CO₂C₂H₅ | H | H | —CH₂OCOCH₃ |
| —COC₆H₁₃ | —C₂H₅ | H | H | —CH₂OCOCH₃ |
| —SO₂—C₆H₅ | —CH₃ | H | H | —CH₂OCOCH₃ |
| —SO₂—C₆H₄—CH₃ (p) | —CH₃ | H | H | —CH₂OCOCH₃ |

-continued

| R₁ | R₂ | R₃ | R₄ | A |
|---|---|---|---|---|
| —COCH₂—S—C₆H₅ | —CH₃ | H | H | —CH₂—SCOCH₃ |
| —CO—CH₂Cl | —CH₃ | H | H | —CH₂—S—(triazole-N-CH₃) |
| —COOCH₂CCl₃ | —CH₃ | H | H | —CH₂OCOCH₃ |
| —COOCH₂CCl₃ | —H | H | H | —CH₂OCOCH₃ |
| —COOCH₂CCl₃ | —C₂H₅ | H | H | —CH₂OCOCH₃ |
| —CHO | —CH(CH₃)₂ | H | H | —CH₂SCOCH₃ |
| —C(CH₃)₃ | —CH₃ | H | H | —CH₂OCOCH₃ |
| —C(CH₃)₃ | —CH₃ | H | H | —CH₂—S—(triazole-N-CH₃) |
| —CH₃ / —COOC(CH₃)₃ | —CH₃ | H | H | —CH₂OCOCH₃ |
|  | —CH₃ | H | —OCH₃ | —CH₂OCOCH₃ |
| —CH₂—C₆H₅ | —CH₃ | H | H | —CH₂OCOCH₃ |
| —CH₂—C₆H₄(OCH₃) | —C₂H₅ | H | H | —CH₂OCOCH₃ |

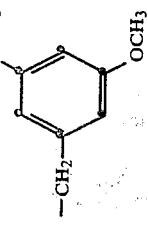

-continued
| R$_1$ | R$_2$ | R$_3$ | R$_4$ | A |
|---|---|---|---|---|
| H | CH$_3$ | CH$_2$OCC(CH$_3$)$_3$ | H |  |
| H | CH$_3$ |  | H |  |
| H | CH$_3$ |  | H |  |
| H | CH$_2$—CH=CH$_2$ | CH$_2$—CCl$_3$ | H |  |
| H | (CH$_3$)$_2$CH | H | H |  |
|  | CH$_3$ | H | H |  |
|  | CH$_3$ | H | H |  |
| H | CH$_2$CO$_2$H | H | H |  |

-continued

| R₁ | R₂ | R₃ | R₄ | A |
|---|---|---|---|---|
| H | CH₂CONH₂ | H | H | N=N-C(CH₃)=... -S- ...=C(SCH₃)- (thiadiazole with CH₃ and CH₂S) |
| H | CH₂CONHCH₃ | H | H | (same as above) |
| H | COOH (on cyclopropane) | H | H | (same) |
| H | C(CH₃)₃ | (benzofuranone ring) | H | (same) |
| H | CH–CO₂H / C₂H₅ | H | H | (same) |
| H | CH₃ | C(CH₃)₃ | H | (same) |
| H | C(=O)CH₃ | H | H | (same) |
| H | C(=O)CH₂Cl | H | H | (same) |
| H | CH₃ | H | OCH₃ | (same) |

-continued
| R₁ | R₂ | R₃ | R₄ | A |
|---|---|---|---|---|
| H | C₂H₅ | H | H | (same heterocyclic group) |
| H | C₃H₇n | H | H | " |
| H | CH₂—CH=CH₂ | H | H | " |
| H | CH₂—CH=CH—CH₃ | H | H | " |
| H | C₄H₉n | H | H | " |
| H | (CH₃)₃C—C₂H₅ (CH₃—C(CH₃)—C₂H₅) | H | H | " |
| H | CH(CH₃)—COOH | H | H | " |
| H | CH(C₃H₇)—COOH | H | H | " |
| H | CH₂COOCH₃ | H | H | " |
| H | CH₂COOC₂H₅ | H | H | " |
Where A in every row is:

-continued

| R₁ | R₂ | R₃ | R₄ | A |
|---|---|---|---|---|
| H | CH₂C(=O)—NC₄H₉ (H on N) | H | H | N=N(CH₃)—S—C(CH₂S)= |
| H | cyclohexyl-COOH | H | H | N=N(CH₃)—S—C(CH₂S)= |
| H | —C(=O)—CH₃ | H | H | N=N(CH₃)—S—C(CH₂S)= |
| H | —C(=O)—CH₂Cl | H | H | N=N(CH₃)—S—C(CH₂S)= |
| H | —C₆H₄—CH₃ | H | H | N=N(CH₃)—S—C(CH₂S)= |
| H | —CH₂—C₆H₅ | H | H | N=N(CH₃)—S—C(CH₂S)= |
| H | —CH₂—C₆H₄—NO₂ | H | H | N=N(CH₃)—S—C(CH₂S)= |
| H | —CH₂—C₆H₄—OCH₃ | H | H | N=N(CH₃)—S—C(CH₂S)= |

-continued
| R₁ | R₂ | R₃ | R₄ | A |
|---|---|---|---|---|
| H | 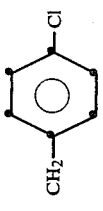 | H | H | 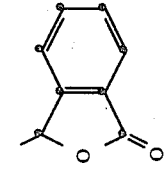 |
| H | —CH—COOH (cyclopropyl) | H | H | 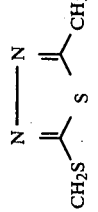 |
| H | —CH—COOH (cyclopentyl) | H | H |  |
| H | CH₂SO₃H | H | H | 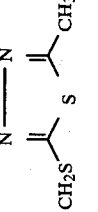 |
| H | CH₂SO₂NH₂ | 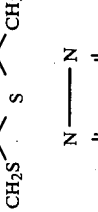 | H |  |
| H | H | CH₂CCl₃ | H |  |
| H | CH₃ | CH₂CCl₃ | H | 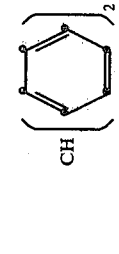 |
| H | CH₃ | 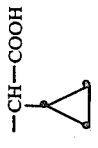 | H |  |

-continued
| $R_1$ | $R_2$ | $R_3$ | $R_4$ | A |
|---|---|---|---|---|
| H | H |  | H | 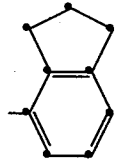 |
| H | H | 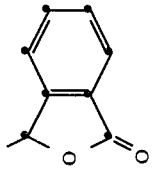 | H | 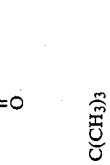 |
| H | H | 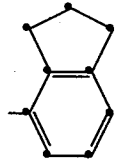 | H |  |
| H | H | $CH_2OCC(CH_3)_3$<br>$\parallel$<br>$O$ | H | 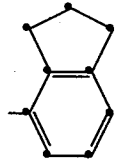 |
| H | H | $C(CH_3)_3$ | H |  |
| H | $CH_3$ | H | H | 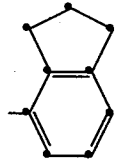 |
| H | $CH_3$ | $C(CH_3)_3$ | H |  |
| H | $CH_3$ | 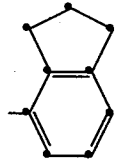 | H |  |
| $ClCH_2C$<br>$\parallel$<br>$O$ | | | | |
| $ClCH_2C$<br>$\parallel$<br>$O$ | | | | |
| $ClCH_2C$<br>$\parallel$<br>$O$ | | | | |

-continued

| $R_1$ | $R_2$ | $R_3$ | $R_4$ | A |
|---|---|---|---|---|
| ClCH$_2$C(=O) | CH$_3$ | -CH$_2$-C$_6$H$_5$ | H | -N=C(CH$_3$)-S-C(CH$_2$S-)= |
| ClCH$_2$C(=O) | -CH$_2$-C$_6$H$_5$ | H | OCH$_3$ | -N=C(CH$_3$)-S-C(CH$_2$S-)= |
| (C$_6$H$_5$)$_3$C- | -CH$_2$-C$_6$H$_4$-NO$_2$ | H | H | -N=C(CH$_3$)-S-C(CH$_2$S-)= |
| BrCH$_2$C(=O) | -CH$_2$-C$_6$H$_4$-OCH$_3$ | 2-isopropoxybenzoyl | H | -N=C(CH$_3$)-S-C(CH$_2$S-)= |
| H | -CH$_2$-C$_6$H$_4$-Cl | indanyl | H | -N=C(CH$_3$)-S-C(CH$_2$S-)= |
| H | CH$_3$ | H | H | -N=C(C$_4$H$_9$)-S-C(CH$_2$S-)= |
| ClCH$_2$C(=O) | C(=O)CH$_3$ | H | H | -N=C(C$_4$H$_9$)-S-C(CH$_2$S-)= |
| H | CH$_3$ | H | H | -N=C(CF$_3$)-S-C(CH$_2$S-)= |

-continued
| $R_1$ | $R_2$ | $R_3$ | $R_4$ | A |
|---|---|---|---|---|
| H | H | CH$_3$ | H | 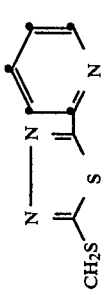 |
| H | 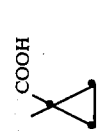 | H | H |  |
| H | 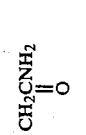 | H | H |  |
| H | H | H | H |  |
| H | CH$_3$ | H | H |  |
| ClCH$_2$C(=O) | CH$_3$ | H | H | 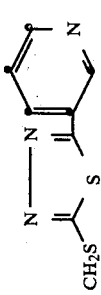 |
| H | CH$_3$ | H | H |  |
| H | CH$_3$ | H | H |  |
| H | CH$_3$ | H | H |  |

-continued
| R₁ | R₂ | R₃ | R₄ | A |
|---|---|---|---|---|
| H | H | H | H | 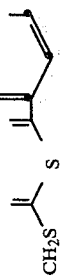 |
| H | H | H | H | 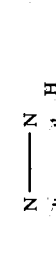 |
| H | CH₃ | H | H | 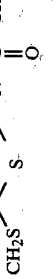 |
| H | CH₃ | 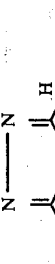 | H |  |
| ClCH₂C(=O) | CH₃ | CH₂OCC(CH₃)₃ (=O) | H | 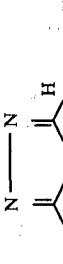 |
| BrCH₂C(=O) | CH₂— | 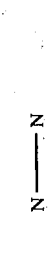 | OCH₃ | 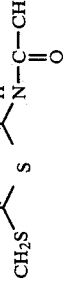 |
| (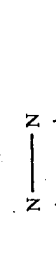)₃C | CH₃ | H | H |  |

-continued
| R₁ | R₂ | R₃ | R₄ | A |
|---|---|---|---|---|
| H | 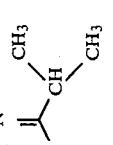 | H | H | 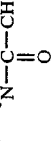 |
| H | H | H | H | 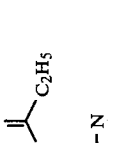 |
| H | H | H | H | 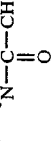 |
| H | CH₃ | H | H | 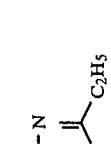 |
| H | CH₃ | CH₂OCC(CH₃)₃<br>‖<br>O | H | 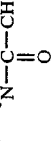 |
| H | CH₃ | 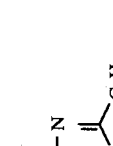 | H | 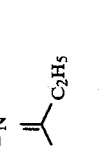 |
| H | CH₃ | 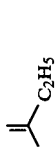 | H |  |
| ClCH₂C=O | CH₃ | C(CH₃)₃ | H | 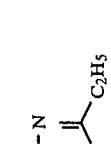 |

-continued
| R₁ | R₂ | R₃ | R₄ | A |
|---|---|---|---|---|
| H | CH₃ | H | H | 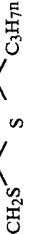 |
| H | H | H | H | 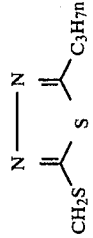 |
| H | CH₃ | H | H | 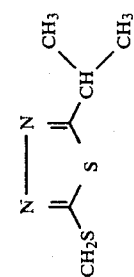 |
| H | CH₂—CH=CH₂ | H | H | 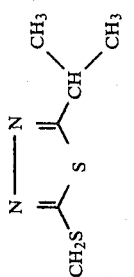 |
| H | CH—COOH<br> \|<br>C₃H₇ | H | H |  |
| H | H | H | H | 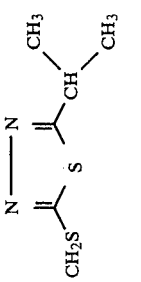 |
| H | CH₃ | H | OCH₃ | 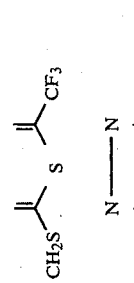 |
| H | CH—COOH (cyclopentyl) | H | H | 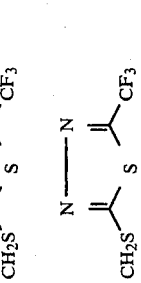 |

-continued

| $R_1$ | $R_2$ | $R_3$ | $R_4$ | A |
|---|---|---|---|---|
| H | CH—COOH—[phenyl] | H | H | [N=N, CH2S, C(CF3)=] thiadiazole |
| H | [cyclopropyl with COOH and CH3] | CH3 | H | [N=N, CH2S, C(CF3)=] thiadiazole |
| ClCH2C(=O)— [phenyl](C)3 | CH3 | H | H | [N=N, CH2S, C(CF3)=] thiadiazole |
| H | CH3 | H | H | [N=N, CH2S, C(CF3)=] thiadiazole |
| H | H | H | H | [N=N, CH2S, C(=)—(4-Cl-phenyl)] thiadiazole |
| H | CH3 | H | H | [N=N, CH2S, C(=)—(4-Cl-phenyl)] thiadiazole |
| H | H | H | OCH3 | [N=N, CH2S] thiadiazole |
| H | CH3 | CH2OCC(CH3)3 (=O) | H | [N=N, CH2S] thiadiazole |

-continued

| R₁ | R₂ | R₃ | R₄ | A |
|---|---|---|---|---|
| H | CH₃ | ![phthalide] | H | N=N–CH=C(SCH₂S)– |
| H | CH₃ | H | H | N=N–C(furan)=C(SCH₂S)– |
| H | CH₃ | H | H | N=N–C(furan)=C(SCH₂S)– |
| H | H | H | H | N=N–C(furan)=C(SCH₂S)– |
| H | H | H | H | N=N–C(furan)=C(SCH₂S)– |
| H | CH₃ | C(CH₃)₃ | H | N=N–C(furan)=C(SCH₂S)– |
| H | H | H | H | N=N–C(thiophene)=C(SCH₂S)– |
| H | CH₃ | H | H | N=N–C(thiophene)=C(SCH₂S)– |

-continued
| $R_1$ | $R_2$ | $R_3$ | $R_4$ | A |
|---|---|---|---|---|
| H | $CH_3$ | $CH_2OCC(CH_3)_3$ with C=O | H |  |
| H | $CH_3$ | (2-isopropylbenzoyloxymethyl group) | H |  |
| H | $CH_3$ | (indanyl group) | H |  |
| H | $CH_2COOH$ | H | H |  |
| H | $CH_2C(=O)NH_2$ | H | H |  |
| H | $CH_2-CO_2CH_3$ | H | H |  |
| H | $C(=O)CH_3$ | H | H |  |
| $ClCH_2C(=O)$ | $CH_3$ | H | H |  |
| $BrCH_2C(=O)$ | $CH_3$ | H | H | |

-continued
| $R_1$ | $R_2$ | $R_3$ | $R_4$ | A |
|---|---|---|---|---|
|  | $CH_3$ | H | H | 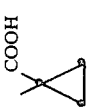 |
| $H_3C-\overset{\underset{\|}{O}}{C}-$ | $CH_3$ | H | H | 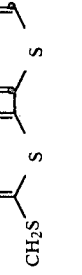 |
| $(CH_3)_3OC-\overset{\underset{\|}{O}}{}$ | $CH_3$ | H | H | 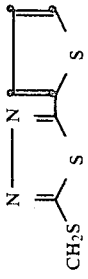 |
| H | 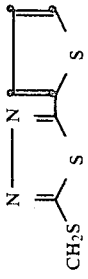 | H | H | 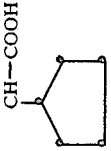 |
| H |  | H | H | 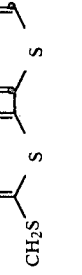 |
| H | $CH_3$ | H | $OCH_3$ | 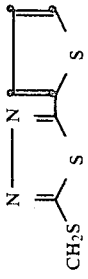 |
| H | 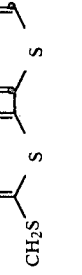 | H | H | 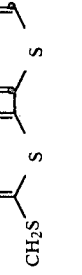 |
| H | H | $CH_2OCC(CH_3)_3$<br>$\overset{\|}{O}$ | H | 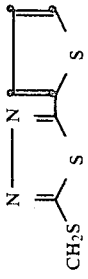 |

-continued
| R₁ | R₂ | R₃ | R₄ | A |
|---|---|---|---|---|
| H | H | H | H | 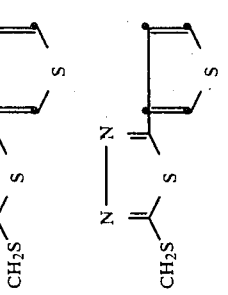 |
| H | CH₃ | H | H | 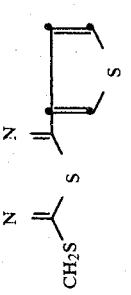 |
| ClCH₂C(=O) | CH₃ | H | H | 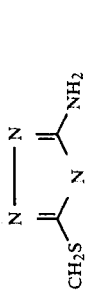 |
| H | H | H | H | 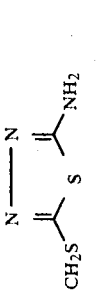 |
| H | CH₃ | H | H | 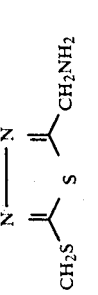 |
| H | CH₃ | H | H | 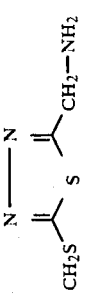 |
| H | H | H | H | 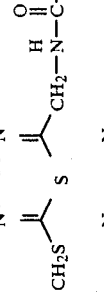 |
| H | CH₃ | H | H | 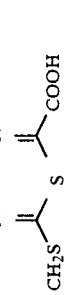 |
| H | H | H | H |  |

-continued

| R₁ | R₂ | R₃ | R₄ | A |
|---|---|---|---|---|
| H | CH₃ | H | H | thiadiazole-CH₂S / COOH |
| H | CH₂COOH | H | H | thiadiazole-CH₂S / COOH |
| H | CH₂C(=O)NH₂ | H | H | thiadiazole-CH₂S / COOH |
| H | 1-methylcyclopropyl-COOH | H | H | thiadiazole-CH₂S / COOH |
| H | 1-cyclohexyl-COOH | H | H | thiadiazole-CH₂S / COOH |
| H | cyclopentyl-CH-COOH | H | H | thiadiazole-CH₂S / COOH |
| H | H | H | H | thiadiazole-CH₂S / C(=O)N(CH₃)₂ |
| H | CH₃ | H | H | thiadiazole-CH₂S / C(=O)N(CH₃)₂ |

-continued

| R₁ | R₂ | R₃ | R₄ | A |
|---|---|---|---|---|
| H | H | | H | $\underset{CH_2S}{\overset{N-N}{\diagdown\diagup}}\!\!\underset{S}{\diagup}\!\!-CONH_2$ |
| H | CH₃ | | H | $\underset{CH_2S}{\overset{N-N}{\diagdown\diagup}}\!\!\underset{S}{\diagup}\!\!-CONH_2$ |
| H | CH₃ | | H | $\underset{CH_2S}{\overset{N-N}{\diagdown\diagup}}\!\!\underset{S}{\diagup}\!\!-CH_2COOH$ |
| H | H | | H | $\underset{CH_2S}{\overset{N-N}{\diagdown\diagup}}\!\!\underset{S}{\diagup}\!\!-CH_2COOH$ |
| H | CH₃ | | H | $\underset{CH_2S}{\overset{N-N}{\diagdown\diagup}}\!\!\underset{S}{\diagup}\!\!-CH_2COOH$ |
| ClCH₂C(=O) | CH₃ | | H | $\underset{CH_2S}{\overset{N-N}{\diagdown\diagup}}\!\!\underset{S}{\diagup}\!\!-CH_2COOH$ |
| BrCH₂C(=O) | CH₃ | | H | $\underset{CH_2S}{\overset{N-N}{\diagdown\diagup}}\!\!\underset{S}{\diagup}\!\!-CH_2COOH$ |
| (C₆H₅)₃C— | CH₃ | | H | $\underset{CH_2S}{\overset{N-N}{\diagdown\diagup}}\!\!\underset{S}{\diagup}\!\!-CH_2COOH$ |
| H | CH₃ | CH₂OC(=O)C(CH₃)₃ | H | $\underset{CH_2S}{\overset{N-N}{\diagdown\diagup}}\!\!\underset{S}{\diagup}\!\!-CH_2CO_2C_2H_5$ |
| H | CH₃ | | H | $\underset{CH_2S}{\overset{N-N}{\diagdown\diagup}}\!\!\underset{S}{\diagup}\!\!-CH_2CO_2C_2H_5$ |

-continued

| R₁ | R₂ | R₃ | R₄ | A |
|---|---|---|---|---|
| H | CH₃ | | H | ![N-N, CH₂S, S, CH₂CO₂C₂H₅] |
| H | H | | H | N—N, CH₂S–S–C(CH₂CO₂C₂H₅) |
| H | cyclopropyl-COOH (1-methyl) | H | H | N—N, CH₂S–S–C(CH₂CO₂C₂H₅) |
| H | cyclopropyl-CH-COOH | H | H | N—N, CH₂S–S–C(CH₂COOH) |
| H₃C-C(=O) | CH₃ | H | H | N—N, CH₂S–S–C(CH₂COOH) |
| H | CH₃ | H | H | N—N, CH₂S–S–C(CH₂COOH) |
| H | CH₃ | H | H | N—N, CH₂S–S–C(CH₂OH) |
| H | CH₃ | H | H | N—N, CH₂S–S–C(CH₂—CH₂OH) |
| H | H | H | H | N—N, CH₂S–S–C(N(CH₃)–C(=O)CH₃) |
| H | H | H | H | N—N, CH₂S–S–C(CH₂OH) |

-continued

| R₁ | R₂ | R₃ | R₄ | A |
|---|---|---|---|---|
| H | CH₂—CH=CH₂ | H | H | hydrazinyl-thiazole with CH₂SH and CH₂OH |
| H | CH₃ | H | H | benzothiazole-hydrazone with CH₂S |
| H | H | H | H | benzothiazole-hydrazone with CH₂S |
| H | C(=O)CH₃ | H | H | benzothiazole-hydrazone with CH₂S |
| H | CH₃ | H | H | benzothiazole N-oxide hydrazone with CH₂S |
| H | CH₃ | H | H | morpholinyl-carbonyl thiazole hydrazone with CH₂S |
| H | CH₃ | H | H | hydrazone-S-CH₂-CO₂H with CH₂S |
| H | H | H | H | thiazole hydrazone-S-CH₂-CO₂H with CH₂S |

-continued

| R₁ | R₂ | R₃ | R₄ | A |
|---|---|---|---|---|
| H | CH₃ | H | H | ![structure with N—N, CH₂S, S—CH₂—CN] |
| H | CH₃ | H | H | ![structure with N—N, CH₂S, S—CH₂—CO₂CH₃] |
| H | CH₃ | H | H | ![structure with N—N, CH₂S, S—CH₂SO₃H] |
| H | CH₃ | H | H | ![structure with N, CH₂S, S, 4-Cl-2-methylphenyl] |
| H | CH₃ | H | H | ![structure with N—N, CH₂S, S—C₃H₇n] |
| H | CH₃ | C(CH₃)₃ | H | ![structure with N—N, CH₂S, S—NH—C(=O)CH₃] |
| H | CH₃ | H | H | ![thiazole structure N, CH₂S, S] |
| H | CH₂COOH | H | H | ![thiazole structure N, CH₂S, S] |
| H | ![cyclohexyl with COOH] | H | H | ![thiazole structure N, CH₂S, S] |

| $R_1$ | $R_2$ | $R_3$ | $R_4$ | A |
|---|---|---|---|---|
| H | CH₂—CH=CH₂ | H | OCH₃ | thiazoline with CH₂S, =CH₂ |
| H | CH₂—CH₃ | benzofuranone | H | thiazoline with CH₂S, =CH₂ |
| H | CH₃ | H | H | thiazoline with CH₂S, =C(CH₃) |
| H | CH₃ | H | OCH₃ | thiazoline with CH₂S, =C(CH₃) |
| ClCH₂C(=O) | cyclopropyl-COOH | H | H | thiazoline with CH₂S, =C(CH₃) |
| BrCH₂C(=O) | CH₃ | H | H | thiazoline with CH₂S, =C(CH₃) |
| (C₆H₅)— | CH₂COOH | benzofuranone | H | thiazoline with CH₂S, =C(CH₃) |
| H | CH(CH₃)CH₃ | H | H | thiazoline with CH₂S, =C(CH₃) |

-continued

| R₁ | R₂ | R₃ | R₄ | A |
|---|---|---|---|---|
| H | CH₃ | H | H | N=C(CF₃)–S–C(CH₂S)  |
| H | CH₃ | C(CH₃)₃ | H | N=C(CF₃)–S–C(CH₂S) |
| H | H | H | H | N=C(CF₃)–S–C(CH₂S) |
| H | CH₃ | H | H | N=C(CF₃)–S–C(CH₂S) |
| ClCH₂C(=O) | C(=O)–CH₃ | H | H | N=C(CF₃)–S–C(CH₂S) |
| H | CH₂–CH=CH–CH₃ | H | H | N=C(C₆H₅)–S–C(CH₂S) |
| H | CH₃ | CH₃ | H | N=C(C₆H₅)–S–C(CH₂S) |
| H | CH₂C(=O)OCH₃ | H | H | N=C(C₆H₅)–S–C(CH₂S) |
| H | CH₃ | H | H | N=C(C₆H₅)–S–C(CH₂S) |

-continued

| R₁ | R₂ | R₃ | R₄ | A |
|---|---|---|---|---|
| H (phenyl-C)₃ | CH—COOH (cyclopropyl) | H | H | N=C(phenyl)–CH₂S–C(CH₂S)=S |
| H | H | H | H | N=C(CH₂COOH)–CH₂S–C(CH₂S)=S |
| H | CH₃ | H | H | N=C(CH₂COOH)–CH₂S–C(CH₂S)=S |
| H | CH₃ | H | H | N=C(C₄H₉n)–CH₂S–C(CH₂S)=S |
| H | CH₃ | H | H | N=C(C₂H₅)–CH₂S–C(CH₂S)=S |
| H | CH₃ | H | H | N=C(H)(NH₂)–CH₂S–C(CH₂S)=S |
| H | CH₃ | H | H | N=C(H)(N(CH₃)–C(=O)CH₃)–CH₂S–C(CH₂S)=S |
| H | CH₃ | H | H | O⁻–N⁺=C(4-OCH₃-phenyl)–CH₂S–C(CH₂S)=S |

-continued

| R₁ | R₂ | R₃ | R₄ | A |
|---|---|---|---|---|
| H | CH₃ | H | H | (4-methylphenyl-N→O)-C(CH₂S-)=N-S- |
| H | CH₃ | H | H | (4-pyridyl)-C(CH₂S-)=N-S- |
| H | CH₃ | H | H | CH₃-C(CH₂S-)=N-S- with CH₂COOH |
| H | CH₃ | H | H | HOOC-C(CH₂S-)=N-S- with CH₃ |
| H | H | H | H | (thienyl)-C(CH₂S-)=N-S- |
| H | CH₃ | H | H | (thienyl)-C(CH₂S-)=N-S- |
| H | CH₃ | H | H | (5-nitrothienyl)-C(CH₂S-)=N-S- |
| (C₆H₅)₃C- | CH₃ | CH₂OC(=O)C(CH₃)₃ | H | HOOCCH₂-C(CH₂S-)=N-S- |

-continued

| $R_1$ | $R_2$ | $R_3$ | $R_4$ | A |
|---|---|---|---|---|
| ClCH$_2$C(=O)- | -CH$_2$-C$_6$H$_4$-NO$_2$ | phthalide-CH$_2$- | H | N=C(CH$_2$S-)(CH$_2$COOH) with S |
| H | CH$_3$ | CH$_2$OCC(CH$_3$)$_3$ (=O) | H | N=C(CH$_2$S-)(CH$_2$COOH) with S |
| H | CH$_3$ | H | H | N=C(CH$_2$S-)(CH$_2$C(=O)C$_2$H$_5$) with S |
| H | CH$_3$ | H | H | N=C(CH$_2$S-)(CH$_2$-C(=O)-OC$_2$H$_5$) with S |
| H | H | H | H | N=C(CH$_2$S-)(thienyl) with S |
| H | CH$_3$ | H | H | N=C(CH$_2$S-)(thienyl) with S |
| H | CH$_3$ | H | H | O←N=C(CH$_2$S-)(phenyl) with S |
| H | CH$_3$ | H | H | O←N=C(CH$_2$S-)(phenyl) with S |

-continued

| R₁ | R₂ | R₃ | R₄ | A |
|---|---|---|---|---|
| H | CH₃ | H | H | (phenyl-substituted oxime thioester structure) |
| H | CH₃ | H | H | (o-methylphenyl-substituted oxime thioester structure) |
| H | CH₃ | H | H | (p-bromophenyl-substituted oxime thioester structure) |
| H | CH₃ | H | H | (methyl-substituted oxime thioester structure) |
| H | H | H | H | (methyl-substituted oxime thioester structure) |
| H | CH₃ | H | H | (methyl-substituted oxime thioester structure) |
| H | CH₃ | H | H | (dimethyl-substituted oxime thioester structure) |
| H | CH₃ | H | H | (oxime thioester structure) |

-continued
| $R_1$ | $R_2$ | $R_3$ | $R_4$ | A |
|---|---|---|---|---|
| H | H | H | H |  |
| H | CH$_3$ | H | H |  |
| H | CH$_3$ | C(CH$_3$)$_3$ | H |  |
| ClCH$_2$C(=O) | CH$_3$ | H | H | |
| BrCH$_2$C(=O) | CH$_2$CH$_3$ | (benzofuranone) | H |  |
| (C$_6$H$_5$)$_3$ | CH$_2$CONH$_2$ | H | H |  |
| H | C(=O)—CH$_3$ | H | H |  |
| H | H | H | H | (with CH$_3$) |
| H | CH$_3$ | H | H |  (with CH$_3$) |

-continued
| $R_1$ | $R_2$ | $R_3$ | $R_4$ | A |
|---|---|---|---|---|
| H | $CH_3$ | $CH_2OCC(CH_3)_3$<br>$\parallel$<br>$O$ | H | 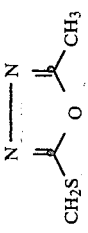 |
| H | $CH_3$ | 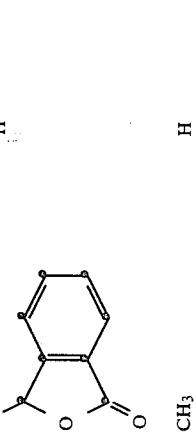 | H |  |
| H | $CH_3$ | $CH_3$ | H | 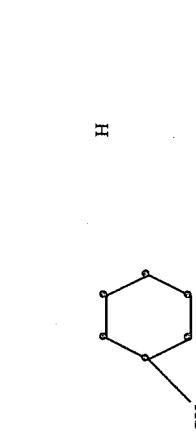 |
| H | $CH_3$ |  | H | 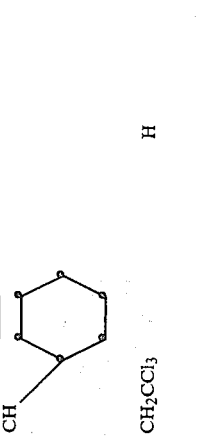 |
| $ClCH_2C$<br>$\parallel$<br>$O$ | $CH_3$ | $CH_2CCl_3$ | H |  |
| $BrCH_2C$<br>$\parallel$<br>$O$ |  | H | H | 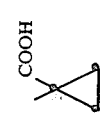 |
|  | $CH_2C$—$NCH_3$<br>$\parallel$ $\;$ $\vert$<br>$O$ $\;$ $H$ | H | H |  |
| H | $H$<br>$C$—$COOH$<br>$C_3H_7$ | H | H |  |

| R₁ | R₂ | R₃ | R₄ | A |
|---|---|---|---|---|
| H | CH₂C(=O)N(H)—C₄H₉ | C(CH₃)₃ | H | N=N, CH₂S, O, CH₃ |
| phenyl-O-CH₂-C(=O)- | CH₃ | (indanyl) | OCH₃ | N=N, CH₂S, O, CH₃ |
| H | CH₃ | H | H | N=N, CH₂S, O, C₂H₅ |
| H | CH₃ | H | H | N=N, CH₂S, O, C₃H₇ |
| H | CH₃ | H | H | N=N, CH₂S, O, C₄H₉ |
| H | CH₃ | H | H | N=N, CH₂S, O, (thienyl) |
| H | CH₃ | H | H | N=N, CH₂S, O, phenyl |
| Cl₃CC(=O) | CH₃ | H | H | N=N, CH₂S, O, phenyl |
| BrCH₂C(=O) | CCH₂Cl(=O) | H | H | N=N, CH₂S, O, phenyl |

-continued

| R₁ | R₂ | R₃ | R₄ | A |
|---|---|---|---|---|
| H | CH₂-C₆H₄-OCH₃ | H | H | N=C(phenyl)-O-C(CH₂S)=N |
| H | 4-CH₃-C₆H₄ | C(CH₃)₃ | H | N=C(phenyl)-O-C(CH₂S)=N |
| (C₆H₅)₃ | CH(CH₃)-COOH | H | H | N=C(phenyl)-O-C(CH₂S)=N |
| H | H | H | H | N=C-S-C(CH₂S)=N (thiazole) |
| H | CH₃ | H | H | N=C-S-C(CH₂S)=N (thiazole) |
| H | CH₃ | H | H | N=C(CONH₂)-O-C(CH₂S)=N |
| H | CH₃ | H | H | N=C(CO₂H)-S-C(CH₂S)=N |
| H | CH₃ | H | H | N=C(CH(CH₃)₂)-O-C(CH₂S)=N |

-continued

| R₁ | R₂ | R₃ | R₄ | A |
|---|---|---|---|---|
| H | CH₃ | H | H | thiophen-2-yl C(CH₂S)=N-N=C(O)- |
| H | CH₃ | H | H | 4-CH₃-C₆H₄- C(CH₂S)=N-N=C(O)- |
| H | CH₃ | H | H | 4-OH-C₆H₄- C(CH₂S)=N-N=C(O)- |
| H | CH₃ | H | H | C₆H₅CH₂- C(CH₂S)=N-N=C(O)- |
| H | CH₃ | H | H | 4-F-C₆H₄- C(CH₂S)=N-N=C(O)- |
| H | CH₃ | H | H | 2-Br-C₆H₄- C(CH₂S)=N-N=C(O)- |
| H | CH₃ | H | H | 2-OCH₃-C₆H₄- C(CH₂S)=N-N=C(O)- |

-continued

| R₁ | R₂ | R₃ | R₄ | A |
|---|---|---|---|---|
| H | CH₃ | H | H | N—N pyrazolyl-CH₂S-oxadiazole |
| H | CH₃ | H | H | N—N imidazolyl-CH₂S-oxadiazole |
| H | CH₃ | H | H | N—N pyridyl-CH₂S-oxadiazole |
| H | CH₃ | H | H | N—N (pyridyl N-oxide)-CH₂S-oxadiazole |
| H | CH₂COOH | H | OCH₃ | N—N CH₂COOH-CH₂S-oxadiazole |
| H | H | H | H | N—N CH₂COOH-CH₂S-oxadiazole |
| H | CH₃ | H | H | N—N CH₂COOH-CH₂S-oxadiazole |
| ClCH₂C(=O) | CH₃ | phthalide | H | N—N CH₂COOCH₃-CH₂S-oxadiazole |

-continued
| R₁ | R₂ | R₃ | R₄ | A |
|---|---|---|---|---|
| H | CH₃ | H | H |  |
| H | CH₃ | H | H | 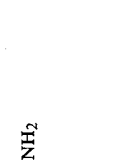 |
| H | CH₃ | H | H | 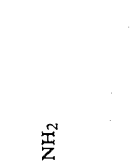 |
| H | CH₃ | H | H |  |
| H | H | H | H |  |
| H | H | H | H |  |
| H | CH₃ | H | H |  |
| H | CH₃ | H | H |  |

-continued

| R₁ | R₂ | R₃ | R₄ | A |
|---|---|---|---|---|
| H | CH₃ | H | H | pyridyl-CH=N-N=C(CH₂S-)-C(=O) |
| H | CH₃ | H | H | pyridyl-CH=N-N=C(CH₂S-)-C(=O) |
| H | CH₃ | H | H | 4-CH₃-C₆H₄-CH=N-N=C(CH₂S-)-C(=O) |
| H | CH₃ | H | H | 4-SO₂NH₂-C₆H₄-CH=N-N=C(CH₂S-)-C(=O) |
| H | CH₃ | H | H | 4-F-C₆H₄-CH=N-N=C(CH₂S-)-C(=O) |
| H | CH₃ | H | H | CF₃-C(=N-N=C(CH₂S-)-C(=O)) |
| ClCH₂C(=O) | $\overset{\|}{\underset{\|}{C}}$—CH₃ (C=O) | H | H | CF₃-C(=N-N=C(CH₂S-)-C(=O)) |
| H | CH₂CO₂C₂H₅ | H | H | CF₃-C(=N-N=C(CH₂S-)-C(=O)) |
| H | CH(C₂H₅)—CO₂C₃H₇ | H | H | CF₃-C(=N-N=C(CH₂S-)-C(=O)) |

-continued

| R₁ | R₂ | R₃ | R₄ | A |
|---|---|---|---|---|
| H | C₄H₉ | H | H | ![](N=N, CH₂S, O, CF₃) |
| H | CH₃ | H | H | ![](N=N, CH₂S, O, CH₂—O—CH₂—CO₂H) |
| H | CH₃ | H | H | ![](N=N, CH₂S, O, CH₂—O—CH₂—CONH₂) |
| H | CH₃ | H | H | ![](N=N, CH₂S, O, CH₂OCH₂—CO₂C₂H₅) |
| H | CH₃ | H | H | ![](N=N, CH₂S, O, CONH₂) |
| H | CH₃ | H | H | ![](N=N, CH₂S, O, H, CONCH₃) |
| H | CH₃ | H | H | ![](N=N, CH₂S, O, C(=O)—N(CH₃)₂) |
| H | H | H | H | ![](N, CH₂S, O) |
| H | CH₃ | H | H | ![](N, CH₂S, O) |

-continued

| R₁ | R₂ | R₃ | R₄ | A |
|---|---|---|---|---|
| H | CH₃ | (3-isopropylphthalide) | H | $\underset{CH_2S}{N}=\overset{}{C}-\overset{O}{C}=N-O$ (ring) |
| H | CH₃ | CH₂OC(=O)C(CH₃)₃ | H | same |
| H | CH₃ | (4-methylindane) | H | same |
| H | CH₃ | –CH(CH₃)–O–C(=O)C(CH₃)₃ | H | same |
| H | H | H | H | same with CH₃ on C |
| H | CH₃ | H | H | same with CH₃ on C |
| H | CH₃ | H | OCH₃ | same with CH₃ on C |
| H | cyclopropyl–CH–COOH | H | H | same with CH₃ on C |

-continued

| R₁ | R₂ | R₃ | R₄ | A |
|---|---|---|---|---|
| H | CH−COOH (cyclopentyl) | H | H | $\underset{CH_3S}{\overset{CH_3}{>}}C=N-O-C(CH_3)=N-$ |
| H | CH₃ | CH₂OCC(CH₃)₃ (O=) | H | $\underset{CH_3S}{\overset{CH_3}{>}}C=N-O-C(CH_3)=N-$ |
| H | CH₂C(=O)NH₂ | CH₂OCC(CH₃)₃ (O=) | H | $\underset{CH_3S}{\overset{CH_3}{>}}C=N-O-C(CH_3)=N-$ |
| H | CH₂COOH | H | H | $\underset{CH_3S}{\overset{CH_3}{>}}C=N-O-C(CH_3)=N-$ |
| H | H | H | H | $\underset{CH_3S}{\overset{Ph}{>}}C=N-O-C(CH_3)=N-$ |
| H | CH₃ | H | H | $\underset{CH_3S}{\overset{Ph}{>}}C=N-O-C(CH_3)=N-$ |
| H | CH₃ | CH₂OCC(CH₃)₃ (O=) | H | $\underset{CH_3S}{\overset{Ph}{>}}C=N-O-C(CH_3)=N-$ |
| H | CH₃ | phthalidyl | H | $\underset{CH_3S}{\overset{Ph}{>}}C=N-O-C(CH_3)=N-$ |

-continued
| R₁ | R₂ | R₃ | R₄ | A |
|---|---|---|---|---|
| H | H | H | H | 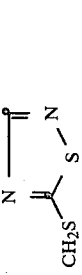 |
| H | CH₃ | H | H | 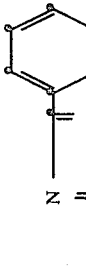 |
| H | CH₃ | (2-isopropoxycarbonylphenyl) | H |  |
| H | CH₃ | CH₂OCC(CH₃)₃‖O | H | 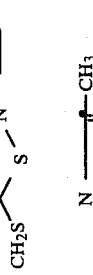 |
| H | CH₃ | H | H | 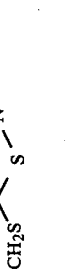 |
| H | CH—COOH (furyl) | H | H |  |
| H | CH₃ | H | H |  |

-continued

| R₁ | R₂ | R₃ | R₄ | A |
|---|---|---|---|---|
| H | CH₃ | ![2-isopropylbenzoate lactone] | H | $\underset{CH_2S}{N}{=}\underset{}{\overset{CH_3}{C}}-N{-}S$ (thiazoline ring) |
| H | CH₃ | CH₂OC(=O)C(CH₃)₃ | H | $\underset{CH_2S}{N}{=}\underset{}{\overset{CH_3}{C}}-N{-}S$ |
| H | CH₃ | ![indanyl] | H | |
| H | H | H | H | $\underset{CH_2S}{N}{=}\underset{}{\overset{C_2H_5}{C}}-N{-}S$ |
| H | CH₃ | H | H | $\underset{CH_2S}{N}{=}\underset{}{\overset{C_2H_5}{C}}-N{-}S$ |
| H | CH₃ | H | H | $\underset{CH_2S}{N}{=}\underset{}{\overset{CH_3}{C}}-\underset{H}{N}{-}N$ |
| ClCH₂CO | CH₃ | H | H | $\underset{CH_2S}{N}{=}\underset{}{\overset{CH_3}{C}}-\underset{H}{N}{-}N$ |
| H | CH₃ | H | H | $\underset{CH_2S}{N}{=}\underset{}{\overset{CH_3}{C}}-\underset{H}{N}{-}N$ |

-continued
| R₁ | R₂ | R₃ | R₄ | A |
|---|---|---|---|---|
| H | CH₃ | CH₂—OCO(CH₃)₃ | H | 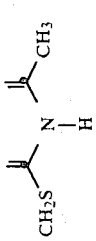 |
| H | CH₃ | H | H | 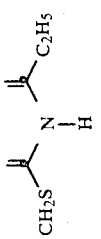 |
| H | H | H | H | 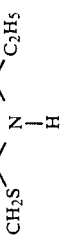 |
| BrCH₂CO | CH₃ | H | H | 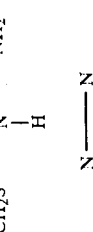 |
| H | CH₃ | H | H | 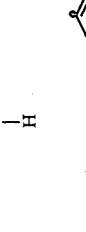 |
| H | CH₃ | H | H | 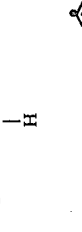 |
| H | C₂H₅ | H | H | 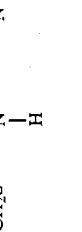 |

-continued
| $R_1$ | $R_2$ | $R_3$ | $R_4$ | A |
|---|---|---|---|---|
| H | CH$_3$ | 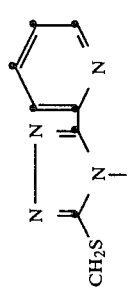 | H | 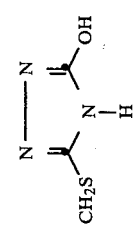 |
| H | CH$_3$ | H | H |  |
| BrCH$_2$CO | CH$_3$ | | H | 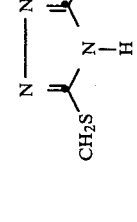 |
| C$_6$H$_5$OCH$_2$CO | CH$_3$ | | H |  |
| C$_6$H$_5$CH$_2$OCO | CH$_3$ | | H | 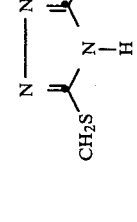 |
| H | CH$_2$CO$_2$H | | H |  |
| H | CH—CO$_2$H<br>\|<br>CH$_3$ | | H |  |

-continued

| R₁ | R₂ | R₃ | R₄ | A |
|---|---|---|---|---|
| H | CH₂—CO₂CH₃ | H | H | CH₂S-[triazole-NH] |
| H | CH₂CO₂C(CH₃)₃ | H | H | CH₂S-[triazole-NH] |
| H | CH—CO₂C₂H₅<br>  |<br>  C₂H₅ | H | H | CH₂S-[triazole-NH] |
| H | CH₂CONH₂ | H | H | CH₂S-[triazole-NH] |
| H | CH₂CONHCH₃ | H | H | CH₂S-[triazole-NH] |
| H | CH₂CON(CH₃)₂ | H | H | CH₂S-[triazole-NH] |
| H | CH₂CON(pyrrolidine) | H | H | CH₂S-[triazole-NH] |

-continued
| $R_1$ | $R_2$ | $R_3$ | $R_4$ | A |
|---|---|---|---|---|
| H |  | H | H |  |
| H |  | H | H | 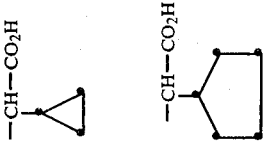 |
| H | 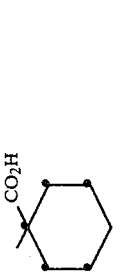 | H | H |  |
| H | 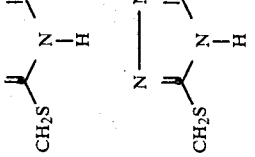 | H | H |  |
| H | $CH_3$ | $-C(CH_3)_3$ | H | 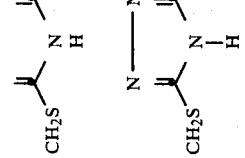 |
| H | $CH_3$ | $CH_2OCOC(CH_3)_3$ | H | 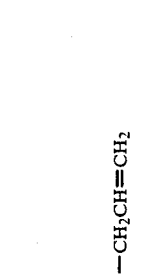 |
| H | $-CH_2CH=CH_2$ | $CH_2OCOC(CH_3)_3$ | H | 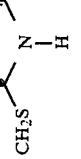 |

-continued

| R₁ | R₂ | R₃ | R₄ | A |
|---|---|---|---|---|
| H | CH₃ | (indane/bicyclic structure) | H | N=N ring with CH₂S, N—H |
| H | CH₃ | (benzofuranone structure) | H | N=N ring with CH₂S, N—H |
| (C₆H₅)₃C | CH₃ | H | H | N=N ring with CH₂S, N—H |
| H | CH₃ | H | OCH₃ | N=N ring with CH₂S, N—H |
| H | H | H | H | N=N ring with CH₂S, N—H |
| H | CH₃ | H | H | N=N ring with CH₂S, N—H (with O-containing ring) |
| H | CH₃ | H | H | N=N ring with CH₂S, N—H (with O-containing ring) |

-continued

| R₁ | R₂ | R₃ | R₄ | A |
|---|---|---|---|---|
| (C₆H₅)₃C | CH₃ | H | H | furan-CH₂S-C(=N-NH)- |
| H | C₃H₇ | H | H | furan-CH₂S-C(=N-NH)- |
| H | CH₃ | C(CH₃)₃ | H | furan-CH₂S-C(=N-NH)- |
| H | CH₃ | CH₂OCOC(CH₃)₃ | H | furan-CH₂S-C(=N-NH)- |
| H | H | H | H | furan-CH₂S-C(=N-NH)- |
| H | CH₃ | H | H | CH₂OCH₃ / CH₂S-C(=N-NH)- |
| H | CH₃ | H | H | 4-(SO₂NH₂)-C₆H₄- / CH₂S-C(=N-NH)- |

-continued

| $R_1$ | $R_2$ | $R_3$ | $R_4$ | A |
|---|---|---|---|---|
| $C_6H_5OCH_2CO$ | $CH_3$ | H | H | N—N(H)—C(CH$_2$S—)=N—(C$_6$H$_4$-SO$_2$NH$_2$) |
| H | —C$_4$H$_9$ | H | H | N—N(H)—C(CH$_2$S—)=N—(C$_6$H$_4$-SO$_2$NH$_2$) |
| H | $CH_3$ | H | OCH$_3$ | N—N(H)—C(CH$_2$S—)=N—(C$_6$H$_4$-SO$_2$NH$_2$) |
| H | $CH_3$ | H | H | N—N(H)—C(CH$_2$S—)=N—C$_6$H$_5$ |
| (C$_6$H$_5$)$_3$C | $CH_3$ | H | H | N—N(H)—C(CH$_2$S—)=N—C$_6$H$_5$ |
| H | $CH_3$ | (phthalide) | H | N—N(H)—C(CH$_2$S—)=N—C$_6$H$_5$ |
| H | H | H | H | N—N(H)—C(CH$_2$S—)=N—C$_6$H$_5$ |

-continued

| R₁ | R₂ | R₃ | R₄ | A |
|---|---|---|---|---|
| H | CH₃ | H | H | -N=C(CH₂S-)-N(H)-N=CH-C₆H₄-OCH₃ |
| H | CH₃ | H | H | -N=C(CH₂S-)-N(H)-N=CH-C₆H₄-Cl |
| H | CH₃ | H | H | -N=C(CH₂S-)-N(H)-N=CH-(pyridyl-CH₃) |
| H | CH₃ | H | H | -N=C(CH₂S-)-N(H)-N=C(CH₂OC₂H₅)- |
| H | CH₃ | H | H | -N=C(CH₂S-)-N(H)-N=C(CH₂OC₆H₅)- |
| H | CH₃ | H | H | -N=C(CH₂S-)-N(H)-N=C(CH₂NHCOCH₃)- |
| H | CH₂CO₂H | H | H | -N=C(CH₂S-)-N(H)-N=C(CH₂NHCOCH₃)- |

-continued

| R₁ | R₂ | R₃ | R₄ | A |
|---|---|---|---|---|
| H | CH₂—CH=CH₂ | H | H | thiadiazole with CH₂S-, N-H, =N-N=, CH₂NHCOCH₃ |
| H | CH₃ | H | H | thiadiazole with CH₂S-, N-H, =N-N=, CH₂CO₂C₂H₅ |
| H | CH₃ | H | H | thiadiazole with CH₂S-, N-H, =N-N=, CH₂CO₂H |
| H | -CH(CH₃)CH₃ | H | H | thiadiazole with CH₂S-, N-H, =N-N=, CH₂CO₂H |
| H | CH₂CONHCH₃ | H | H | thiadiazole with CH₂S-, N-H, =N-N=, CH₂CO₂H |
| H | CH₃ | CH₂OCOC(CH₃)₃ | H | thiadiazole with CH₂S-, N-H, =N-N=, CH₂CONH₂ |
| H | CH₃ | H | H | thiadiazole with CH₂S-, N-H, =N-N=, CH₂CONH₂ |

-continued

| $R_1$ | $R_2$ | $R_3$ | $R_4$ | A |
|---|---|---|---|---|
| H | $CH_2CH=CH_2$ | H | H | $CH_3S\underset{}{\overset{N\!-\!\!\!-\!\!\!-\!N}{\diagup\!\!\!\diagdown}}N\!-\!H$ with $CH_2CONH_2$ |
| H | $CH_3$ | H | H | $CH_3S\underset{}{\overset{N\!-\!\!\!-\!\!\!-\!N}{\diagup\!\!\!\diagdown}}N\!-\!H$ with $CH_2OCH_2\!-\!CO_2H$ |
| H | $CH_3$ | H | H | $CH_3S\underset{}{\overset{N\!-\!\!\!-\!\!\!-\!N}{\diagup\!\!\!\diagdown}}N\!-\!H$ with $CH_2OCH_2\!-\!CONH_2$ |
| $BrCH_2CO$ | $CH_3$ | H | H | $CH_3S\underset{}{\overset{N\!-\!\!\!-\!\!\!-\!N}{\diagup\!\!\!\diagdown}}N\!-\!H$ with $CH_2OCH_2\!-\!CONH_2$ |
| H | $CH_3$ | H | H | $CH_3S\underset{}{\overset{N\!-\!\!\!-\!\!\!-\!N}{\diagup\!\!\!\diagdown}}N\!-\!H$ with $CONH_2$ |
| H | cyclopropyl-$CO_2H$ | H | H | $CH_3S\underset{}{\overset{N\!-\!\!\!-\!\!\!-\!N}{\diagup\!\!\!\diagdown}}N\!-\!H$ with $CONH_2$ |
| $C_6H_5OCH_2CO$ | $CH_3$ | H | H | $CH_3S\underset{}{\overset{N\!-\!\!\!-\!\!\!-\!N}{\diagup\!\!\!\diagdown}}N\!-\!H$ with $CONH_2$ |

-continued

| R₁ | R₂ | R₃ | R₄ | A |
|---|---|---|---|---|
| H | —C(CH₃)₃ | H | H | ![structure] |
| H | CH₂CONHCH₃ | H | H | ![structure] |
| H | CH₃ | ![benzofuranone structure] | H | ![structure] |
| H | H | H | H | ![structure] |
| H | CH₃ | H | H | ![structure] |
| H | CH₃ | H | H | ![structure] |
| H | H | H | H | ![structure] |

-continued

| R₁ | R₂ | R₃ | R₄ | A |
|---|---|---|---|---|
| H | CH₃ | H | H | $-N=C(CH_2S-)-N(CH_3)-C(=N)-NH_2$ |
| H | CH₃ | H | H | $-N=C(CH_2S-)-N(CH_3)-C(=N)-OH$ |
| H | CH₃ | H | H | thiazole-linked: $-N=C(CH_2S-)-N(CH_3)-$ fused thiophene |
| H | CH₂CO₂H | H | H | thiazole-linked: $-N=C(CH_2S-)-N(CH_3)-$ fused thiophene |
| H | n-C₄H₉ | H | H | thiazole-linked: $-N=C(CH_2S-)-N(CH_3)-$ fused thiophene |
| (C₆H₅)₃C | CH₃ | H | H | thiazole-linked: $-N=C(CH_2S-)-N(CH_3)-$ fused thiophene |
| H | H | H | H | thiazole-linked: $-N=C(CH_2S-)-N(CH_3)-$ fused thiophene |

-continued
| $R_1$ | $R_2$ | $R_3$ | $R_4$ | A |
|---|---|---|---|---|
| H | $CH_3$ | H | H | 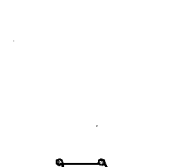 |
| H | $CH_3$ | H | H | |
| H | $C_2H_5$ | H | H | |
| H | $n-C_3H_7$ | H | H | |
| $BrCH_2CO$ | $CH_2CO_2H$ | H | H | |
| H | $CH_2CO_2H$ | H | H | |
| H |  | H | H | |

-continued
| R₁ | R₂ | R₃ | R₄ | A |
|---|---|---|---|---|
| H | CH₂CONHCH₃ | H | H | 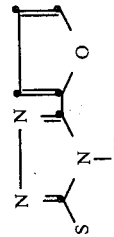 |
| H | CH₃ | 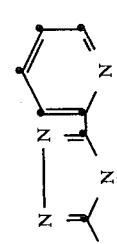 | H | 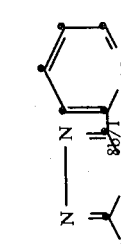 |
| H | CH₃ | H | H | 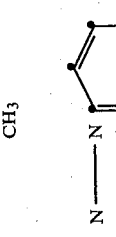 |
| H | CH₂—C≡CH | H | H | 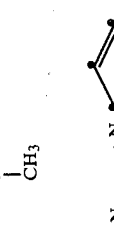 |
| H | CH₃ | CH₂OCOC(CH₃)₃ | H |  |
| H | CH₃ | H | H | |

-continued
| R₁ | R₂ | R₃ | R₄ | A |
|---|---|---|---|---|
| H | —CH₂—CH=CH—CH₃ | H | H | 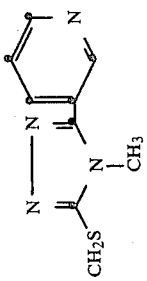 |
| H | H | H | H | 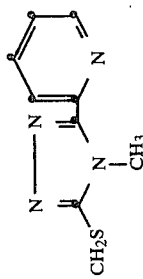 |
| H | H | H | H | 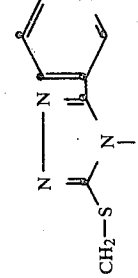 |
| H | CH₃ | —C(CH₃)₃ | H | 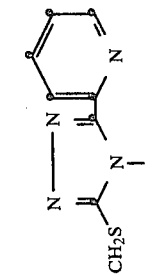 |
| H | CH₃ | H | H | 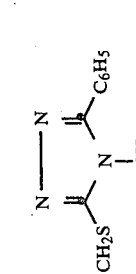 |
| H | CH₃ | $\underset{\parallel}{\text{O}}$<br>CH₂OC—C(CH₃)₃ | H | 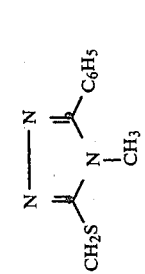 |

-continued

| R₁ | R₂ | R₃ | R₄ | A |
|---|---|---|---|---|
| H | CH₃ | H | H | (pyrazole-CH₂S-C(=N-N-C₂H₅)) |
| H | CH₃ | H | H | (pyridin-2-yl-CH₂S-C(=N-N-C₂H₅)) |
| H | CH₃ | H | H | (pyridin-3-yl-CH₂S-C(=N-N-C₂H₅)) |
| H | CH₃ | H | H | (pyridin-4-yl-CH₂S-C(=N-N-C₂H₅)) |
| H | CH₃ | CH₂OCCH₃ (O=) | H | (pyridinyl-CH₂S-C(=N-N-C₂H₅)) |
| H | CH₃ | H | H | (furan-CH₂S-C(=N-N-C₂H₅)) |
| H | CH₃ | H | H | (furan-CH₂S-C(=N-N-C₂H₅)) |

-continued
| $R_1$ | $R_2$ | $R_3$ | $R_4$ | A |
|---|---|---|---|---|
| H | $C_2H_5$ | H | H | 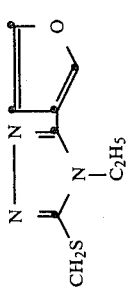 |
| H | $CH_3$ | H | H | 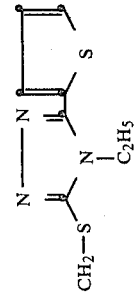 |
| H | $CH_2CO_2H$ | H | H | 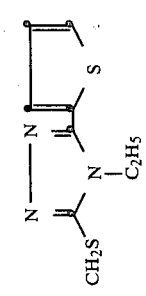 |
| H | $CH_2-CH=CH_2$ | H | H | 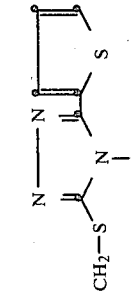 |
| H | $CH_3$ | H | H | 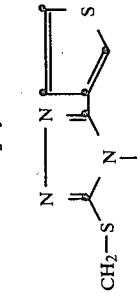 |
| H | $CH_3$ | $C(CH_3)_3$ | H | 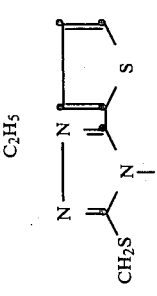 |
| H | H | H | H | 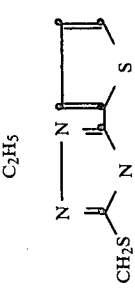 |

-continued

| $R_1$ | $R_2$ | $R_3$ | $R_4$ | A |
|---|---|---|---|---|
| H | CH$_3$ | (phthalide group) | H | thiazole-substituted N-ethyl thiomethyl group |
| H | CH$_3$ | H | H | N-propyl thiomethyl group |
| H | CH$_3$ | H | H | thiazole-substituted N-propyl thiomethyl group |
| H | CH$_3$ | H | H | pyridine-substituted N-propyl thiomethyl group |
| H | CH$_3$ | H | H | oxazole-substituted N-propyl thiomethyl group |
| H | CH$_3$ | CH$_2$OC(=O)—C(CH$_3$)$_3$ | H | oxazole-substituted N-propyl thiomethyl group |
| H | CH$_3$ | H | H | N-allyl thiomethyl group |

-continued

| R₁ | R₂ | R₃ | R₄ | A |
|---|---|---|---|---|
| H | CH₃ | H | H | $\text{CH}_2\text{S}-\overset{\displaystyle N}{\underset{\displaystyle \|}{C}}=N-N(CH_3)(CH_2CH_2CH_2CH_3)$ |
| H | CH₃ | H | H | $\text{CH}_2\text{S}-\overset{\displaystyle N}{\underset{\displaystyle \|}{C}}=N-N(CH_3)(C_6H_{11})$ |
| H | CH₃ | H | H | $\text{CH}_2\text{S}-\overset{\displaystyle N}{\underset{\displaystyle \|}{C}}=N-N(CH_3)(CH_2C_6H_5)$ |
| H | CH₃ | H | H | $\text{CH}_2\text{S}-\overset{\displaystyle N}{\underset{\displaystyle \|}{C}}=N-N(CH_3)(C_6H_5)$ |
| H | CH₃ | H | H | $\text{CH}_2-\text{S}-\overset{\displaystyle N}{\underset{\displaystyle \|}{C}}=N-N(COCH_3)(C_6H_5)$ |
| H | CH₃ | H | H | $\text{CH}_2\text{S}-\overset{\displaystyle N}{\underset{\displaystyle \|}{C}}=N-N(COCF_3)(H)$ |
| H | CH₂CH=CH₂ | H | H | $\text{CH}_2\text{S}-\overset{\displaystyle N}{\underset{\displaystyle \|}{C}}=N-N(COCF_3)(H)$ |

-continued
| R₁ | R₂ | R₃ | R₄ | A |
|---|---|---|---|---|
| H | CH₂CONHCH₃ | H | H |  |
| H | CH—CO₂H<br>  \|<br>  CH₃ | H | H |  |
| H | H | H | H | 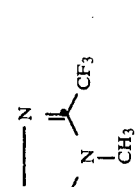 |
| H | CH₃ | H | H | 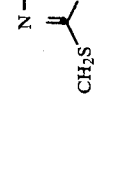 |
| H | n-C₄H₉ | H | H |  |
| H |  | H | H |  |
| H | CH₃ |  | H |  |

-continued

| R₁ | R₂ | R₃ | R₄ | A |
|---|---|---|---|---|
| H | H | H | H | ![](N=N ring with CH₂S, CF₃, N-CH₃) |
| H | CH₃ | H | H | ![](N=N ring with CH₂S, CF₃, N-C₂H₅) |
| H | C₂H₅ | H | H | ![](N=N ring with CH₂S, CF₃, N-C₂H₅) |
| H | CH₃ | H | H | ![](N=N ring with CH₂S, CF₃, N-CH₂CO₂H) |
| H | n-C₃H₇ | H | H | ![](N=N ring with CH₂S, CF₃, N-CH₂CO₂H) |
| H | CH₂CO₂H | H | H | ![](N=N ring with CH₂S, CF₃, N-CH₂CO₂H) |
| H | CH₂CONH₂ | H | H | ![](N=N ring with CH₂S, CF₃, N-CH₂CO₂H) |

-continued

| R₁ | R₂ | R₃ | R₄ | A |
|---|---|---|---|---|
| H | H | H | H | CH₃S–C(=N–N=)–N(CH₂CO₂H)–C(CF₃)= (pyrazole) |
| H | CH₃ | H | H | CH₃S–C(=N–N=)–N(CH₂CONH₂)–C(CF₃)= |
| H | CH₃ | H | H | CH₃–S–C(=N–N=)–N(C₆H₅)–C(CF₃)= |
| H | CH₃ | H | H | CH₃–S–C(=N–N=)–N(NH₂)–C(CF₃)= |
| H | CH₃ | H | H | CH₃–S–C(=N–N=)–N(CH₂–C₆H₅)–C(CF₃)= |
| H | CH₃ | H | H | CH₃S–C(=N–N=)–N(CH₂CO₂C₂H₅)–C(CF₃)= |
| H | CH₃ | indanyl | H | CH₃S–C(=N–N=)–N(CH₂CO₂C₂H₅)–C(CF₃)= |

-continued

| R₁ | R₂ | R₃ | R₄ | A |
|---|---|---|---|---|
| H | CH₃ | H | H | ![structure: N=N-C(SCH₂-)=N-N(C₆H₄Cl)-C(CF₃)=] thiadiazine with 4-Cl-phenyl and CF₃ |
| H | CH₃ | H | H | pyrazole with CH₂S–, N–CH₃, =N–N=, CH₂CO₂H |
| BrCH₂CO | CH₃ | H | H | pyrazole with CH₂S–, N–CH₃, =N–N=, CH₂CO₂H |
| H | C₂H₅ | H | H | pyrazole with CH₂S–, N–CH₃, =N–N=, CH₂CO₂H |
| H | H | H | H | pyrazole with CH₂S–, N–CH₃, =N–N=, CH₂CO₂H |
| H | CH₃ | H | H | pyrazole with CH₂S–, N–CH₃, =N–N=, CH₂CO₂C₂H₅ |

-continued

| R₁ | R₂ | R₃ | R₄ | A |
|---|---|---|---|---|
| H | CH₃ | H | H | (structure: N=N, CH₂S, N-CH₃, CH₂CONH₂) |
| H | CH₃ | H | H | (structure: N=N, CH₂S, N-CH₃, CH₂OCH₂-CO₂H) |
| H | CH₂CONH₂ | H | H | (structure: N=N, CH₂S, N-CH₃, CH₂OCH₂-CO₂H) |
| H | CH–CO₂H, –CH₃ | H | H | (structure: N=N, CH₂S, N-CH₃, CH₂OCH₂-CO₂H) |
| H | CH₃ | H | H | (structure: N=N, CH₂S, N-CH₃, CH₂OCH₂-CONH₂) |
| H | CH₃ | H | H | (structure: N=N, CH₂S, N-CH₃, CH₂OCH₂-CO₂CH₃) |
| H | CH₃ | H | H | (structure: N=N, CH₂S, N-CH₂SO₃H, CF₃) |

-continued

| $R_1$ | $R_2$ | $R_3$ | $R_4$ | A |
|---|---|---|---|---|
| H | $C_2H_5$ | H | H | pyrazole with $CH_2S-$, $-CF_3$, $N-CH_2SO_3H$ |
| H | cyclopropyl-$CO_2H$ | H | H | pyrazole with $CH_2S-$, $-CF_3$, $N-CH_2SO_3H$ |
| H | $CH_3$ | $CH_2OC(=O)-C(CH_3)_3$ | H | pyrazole with $CH_2S-$, $-CF_3$, $N-CH_2SO_2NH_2$ |
| H | $CH_3$ | H | H | pyrazole with $CH_2S-$, $-CF_3$, $N-CH_2SO_2NH_2$ |
| H | $CH_3$ | H | H | pyrazole with $CH_2S-$, $-CF_3$, $N-CH_2CH_2SO_3H$ |
| H | $CH_3$ | H | H | triazole with $CH_2S-$, $N-CH_2SO_3H$ |
| H | $CH_3$ | H | H | triazole with $CH_2S-$, $N-CH_2SO_2NH_2$ |

-continued
| R₁ | R₂ | R₃ | R₄ | A |
|---|---|---|---|---|
| H | CH₃ | H | H |  |
| H | CH₃ | H | H |  |
| H | CH₃ | H | H |  |
| H | CH₃ | H | H |  |
| H | CH₃ | H | H |  |
| H | H | H | H |  |
| H | C₂H₅ | H | H | |

-continued
| $R_1$ | $R_2$ | $R_3$ | $R_4$ | A |
|---|---|---|---|---|
| H | $CH_2-CH=CH_2$ | H | H |  |
| H | $CH_3$ | H | H |  |
| H | $CH_3$ | H | H |  |
| H | $CH_2CO_2H$ | H | H |  |
| H | $CH_3$ |  | H |  |
| H | $CH_2CONH_2$ | H | H | |
| H | $CH_2CONH_2$ | $CH_2OC(O)-C(CH_3)_3$ | H | |

-continued
| $R_1$ | $R_2$ | $R_3$ | $R_4$ | A |
|---|---|---|---|---|
| $C(C_6H_5)_3$ | $CH_3$ | H | H |  |
| H | H | H | H |  |
| H | $CH_3$ | H | H |  |
| H | $C_2H_5$ | H | H |  |
| H | $CH_3$ | H | H |  |
| H | $CH_3$ | $CH_2OCCH_3$ (O=) | H |  |
| H | $CH_3$ | H | H |  |

-continued
| $R_1$ | $R_2$ | $R_3$ | $R_4$ | A |
|---|---|---|---|---|
| BrCH$_2$CO | CH$_3$ | H | H |  |
| H | CH$_3$ | H | H |  |
| C$_6$H$_5$OCH$_2$CO | CH$_3$ | H | H |  |
| H | H | H | H | |
| H | CH$_3$ | H | H |  |
| H | CH$_3$ | H | H |  |
| H | CH$_3$ | H | H |  |

-continued

| R₁ | R₂ | R₃ | R₄ | A |
|---|---|---|---|---|
| H | CH₃ | H | H | (pyridyl-substituted thiazole with NH₂) |
| H | CH₂CONH₂ | H | H | (pyridyl-substituted thiazole with NH₂) |
| H | CH₂CONH₂ | (indanyl) | H | (pyridyl-substituted thiazole with NH₂) |
| H | CH₃ | H | H | (thiazole with CH₂C₆H₅, NH₂) |
| H | CH₃ | H | H | (thiazole with C₂H₅, HNCOCH₃) |
| H | C₂H₅ | H | H | (thiazole with C₂H₅, HNCOCH₃) |
| H | CH₃ | H | H | (thiazole with C₂H₅, HNC₆H₅) |

-continued

| R₁ | R₂ | R₃ | R₄ | A |
|---|---|---|---|---|
| H | COCH₃ | H | H | heterocycle with O, -CH₂S-C(=N-N)-NH |
| H | COCH₂Cl | H | H | heterocycle with O, -CH₂S-C(=N-N)-NH |
| H | COCH₃ | H | H | heterocycle with O, -CH₂S-C(=N-N)-NH |
| H | COCH₃ | H | H | heterocycle with S, -CH₂S-C(=N-N)-NH |
| H | COCH₂Cl | H | H | heterocycle with S, -CH₂S-C(=N-N)-NH |
| H | CH₃ | H | H | -CH₂S-C(=N-N(CH₃))-N-CH₃ |
| H | —CH(CH₃)₂ | H | H | -CH₂S-C(=N-N(CH₃))-N-CH₃ |

-continued

| R$_1$ | R$_2$ | R$_3$ | R$_4$ | A |
|---|---|---|---|---|
| H | C$_2$H$_5$ | H | H | structure with CH$_2$S, N, N—CH$_2$—CH$_2$—CH$_2$—CH$_3$ |
| BrCH$_2$CO | C$_2$H$_5$ | H | H | structure with CH$_2$S, N, N—CH$_2$—CH$_2$—CH$_2$—CH$_3$ |
| H | CH$_2$CO$_2$H | H | H | structure with CH$_2$S, N, N—C$_6$H$_5$ |
| H | CH$_3$ | H | H | structure with CH$_2$S, CH$_3$, N, N—CH$_3$ |
| H | CH$_3$ | CH$_2$OC(=O)—C(CH$_3$)$_3$ | H | structure with CH$_2$S, CH$_3$, N, N—CH$_3$ |
| H | CH$_3$ | H | H | structure with CH$_2$S, N, N—CH$_2$—CH=CH$_2$ |
| H | CH$_2$—CH=CH$_2$ | H | H | structure with CH$_2$S, N, N—CH$_2$—CH=CH$_2$ |

| R₁ | R₂ | R₃ | R₄ | A |
|---|---|---|---|---|
| H | CH₃ | H | H | ![structure with CH₂S-C(=N-N(CH₃))-C(OH)] |
| H | CH₃ | H | H | ![structure with CH₂S-C(=N-N(C₆H₅))-C(OH)] |
| H | CH₃ | H | H | ![structure with CH₂S-C(=N-N(CH₃))-C(CH₂CO₂H)] |
| H | CH₃ | H | H | ![structure with CH₃S-C=C-N(H)-N=N] |
| H | CH₃ | H | H | ![structure with CH₃S-C=C-N(CH₃)-N=N] |
| H | CH₃ | H | H | ![structure with CH₃S-C=C-N(C₂H₅)-N=N] |
| H | CH₃ | H | H | ![structure with CH₃S-C=C-N(C₆H₅)-N=N] |

-continued

| R₁ | R₂ | R₃ | R₄ | A |
|---|---|---|---|---|
| H | CH₃ | H | H | ![structure: CH₃ and CH₂S on C=C, with C-N(H)-N=N] |
| H | CH₃ | H | H | ![structure: CH₃ and CH₂S on C=C, with C-N(CH₃)-N=N] |
| H | CH₃ | H | H | ![structure: HO₂C and CH₂S on C=C, with C-N(H)-N=N] |
| H | CH₃ | H | H | ![structure: H₂NCO and -CH₂S on C=C, with C-N(H)-N=N] |
| H | CH₃ | H | H | ![structure: HO₂C-CH₂ and -CH₂S on C=C, with C-N(H)-N=N] |
| H | CH₃ | H | H | ![structure: H₂NCOCH₂ and -CH₂S on C=C, with C-N(H)-N=N] |

-continued

| R₁ | R₂ | R₃ | R₄ | A |
|---|---|---|---|---|
| H | CH₃ | H | H | H₃CO₂CCH₂-C(CH₂S—)=C(-CH₃)-NH-N=N |
| H | CH₃ | H | H | H₃CO₂CCH₂-C(CH₂S—)=C(-CH₃)-N(CH₃)-N=N |
| H | CH₃ | H | H | pyrimidine with CH₂S- and -OCH₂CO₂H substituents |
| H | CH₂CO₂H | H | H | pyrimidine with CH₂S- and -O-CH₂-CO₂H substituents |
| H | —CH₂—C₆H₅ | H | H | pyrimidine with CH₂S- and -OCH₂-CO₂H substituents |
| H | H | H | H | pyrimidine with CH₂S- and -OCH₂-CO₂H substituents |
| H | CH₃ | H | H | pyrimidine with CH₂S- and -S-CH₂-CO₂H substituents |

-continued

| R₁ | R₂ | R₃ | R₄ | A |
|---|---|---|---|---|
| H | CH₂-C₆H₄-Cl | H | H | pyrimidine with SCH₂CO₂H and CH₃S substituents |
| H | H | H | H | pyrimidine with SCH₂CO₂H and CH₃S substituents |
| H | CH₃ | H | H | pyrimidine with SCH₂CO₂CH₃ and CH₃S substituents |
| BrCH₂CO | CH₃ | CH₂OC(O)C(CH₃)₃ | H | pyrimidine with SCH₂CO₂H and CH₃S substituents |
| H | CH₃ | H | H | pyrimidine with OH and CH₃S substituents |
| H | C₂H₅ | H | H | pyrimidine with OCH₃ and CH₃S substituents |
| H | C₆H₅ | indanyl | H | pyrimidine with OH and CH₃S substituents |

-continued

| R₁ | R₂ | R₃ | R₄ | A |
|---|---|---|---|---|
| H | CH₃ | H | H | pyrimidine with CH₂S- substituent and -OCH₂CO₂H |
| BrCH₂CO | CH₃ | H | H | pyrimidine with CH₂S- substituent and -OCH₂CO₂H |
| (C₆H₅)₃C | CH₃ | H | H | pyrimidine with CH₂S- substituent and -OCH₂CO₂H |
| H | H | H | H | pyrimidine with CH₂S- substituent and -OCH₂CO₂H |
| H | CH₃ | H | H | pyrimidine with CH₂S- substituent and -OCH₂-CO₂C₂H₅ |
| H | CH₃ | H | H | pyrimidine with CH₂S- substituent and -SCH₂-CO₂H |
| H | CH₃ | CH₂OC(=O)CH₃ | H | pyrimidine with CH₂S- substituent and -S-CH₂CO₂H |
| H | H | H | H | pyrimidine with CH₂S- substituent and -S-CH₂CO₂H |

-continued
| R₁ | R₂ | R₃ | R₄ | A |
|---|---|---|---|---|
| H | CH₃ | H | H |  |
| H | CH₂CO₂H | H |   |  |
| H | CH₃ |   |   |  |
| H | CH₂CONHCH₃ |   |   |  |
| H | CH₃ | H | H |  |
| H | CH₃ | H | H |  |
| H | CH₃ | H | H |  |
| H | CH₃ | H | H |  |

-continued

| R₁ | R₂ | R₃ | R₄ | A |
|---|---|---|---|---|
| H | CH₃ | H | H | 3-methyl-6-(methylthio)pyridazine 1-oxide |
| H | CH₃ | H | H | 3-(carboxymethyl)-6-(methylthio)pyridazine 1-oxide |
| H | CH₃ | H | H | 3-(ethoxycarbonylmethyl)-6-(methylthio)pyridazine 1-oxide |
| H | CH₃ | H | H | 4-methyl-3-(ethoxycarbonylmethyl)-6-(methylthio)pyridazine 1-oxide |
| H | CH₃ | H | H | 4-methyl-6-(methylthio)pyridazine 2-oxide |
| H | CH₃ | H | H | 4-(ethoxycarbonylmethyl)-6-(methylthio)pyridazine 2-oxide |

-continued

| R₁ | R₂ | R₃ | R₄ | A |
|---|---|---|---|---|
| H | CH₃ | H | H | pyrimidine ring with CH₃, CH₂CO-OC₂H₅, N→O, CH₃S substituents |
| H | —CH₃ | H | H | —CH₂—S-(2-pyridyl) |
| H | —CH₂—COOH | H | H | —CH₂—S-(2-pyridyl) |
| H | —CH₂—CH=CH₂ | H | H | —CH₂—S-(2-pyridyl) |
| H | —CH₂—CH₃ | phthalide group | H | —CH₂—S-(pyridyl) |
| H | —CH₃ | H | H | —CH₂—S-(3-COOH-2-pyridyl) |
| H | —CH₃ | H | H | —CH₂—S-(2-pyridyl) |

-continued

| R₁ | R₂ | R₃ | R₄ | A |
|---|---|---|---|---|
| Cl—CH₂—C(=O)— | —CH(CH₃)₂ | H | H | —CH₂—S-(pyridine with N) |
| H | —CH₂—CH₂—CH₃ | H | H | —CH₂—S-(pyridine with COOH) |
| H | —CH₃ | H | H | —CH₂—S-(pyridine with NO₂) |
| H | H | H | H | —CH₂—S-(pyridine with CH₃) |
| H | —CH₂—C₆H₅ | H | H | —CH₂—S-(pyridine with CH₃) |
| H | —CH₂—CH₂—CH₂—CH₃ | H | H | —CH₂—S-(pyridine with COOH, CH₃) |
| H | —CH₃ | —CH₂—O—C(=O)—C(CH₃)₃ | H | —CH₂—S-(pyridine with N) |

-continued
| $R_1$ | $R_2$ | $R_3$ | $R_4$ | A |
|---|---|---|---|---|
| H | —CH$_3$ | H | H | 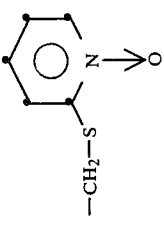 |
|  | —CH$_2$—CH$_3$ | H | H | 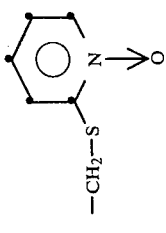 |
| H | —CH$_2$—CH=CH$_2$ | H | OCH$_3$ | 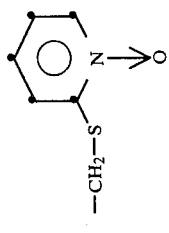 |
| H | H | H | H | 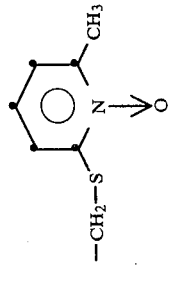 |
| H | —CH$_3$ | —CH$_2$—COOH | H | 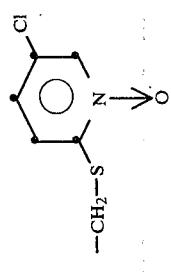 |

-continued

| R₁ | R₂ | R₃ | R₄ | A |
|---|---|---|---|---|
| H | -CH₂-(4-Cl-phenyl) | H | H | -CH₂-S-(4-methylpyridine N-oxide) |
| H | -CH(CH₃)₂ | H | OCH₃ | -CH₂-S-(4-Cl-pyridine N-oxide) |
| H | -CH₃ | -C(CH₃)₃ | H | -CH₂-S-(3-methylpyridine N-oxide) |
| -CH₂-O-C(=O)-(phenyl) | -C(CH₃)₂CH₃ | H | H | -CH₂-S-(3-methylpyridine N-oxide) |
| H-C(=O)- | -CH(cyclopropyl)-COOH | H | H | -CH₂-S-(4-Cl-pyridine N-oxide) |

-continued

| R₁ | R₂ | R₃ | R₄ | A |
|---|---|---|---|---|
| H | CH₃ | H | H | pyridine N-oxide with -CH₂-S- at 4-position and -COOH at 2-position |
| H | -CH-COOH with cyclopentadienyl | H | H | pyridine N-oxide with -CH₂-S- and -COOH |
| Cl-CH₂-C(=O)- | -CH₂-CH=CH₂ | H | H | pyridine N-oxide with -CH₂-S- and -COOH |
| H | -C(CH₃)₂-CH₃ (tert-butyl) | -C(CH₃)₂-CH₃ | H | pyridine N-oxide with -CH₂-S- and -COOH |
| H | pyridyl-C(=O)- | H | H | pyridine N-oxide with -CH₂-S- and -COOH |
| C₄H₉-C(=O)- | -CH₂-CH₂-CH₂-Cl | H | -OCH₃ | pyridine N-oxide with -CH₂-S- and -COOH |

-continued

| R₁ | R₂ | R₃ | R₄ | A |
|---|---|---|---|---|
| H | —CH₂—CH=CH—COOH | H | H | 2-(—CH₂—S—)-pyridine-N-oxide-4-COOH |
| H | —CH₂—CH₂—CH₃ | —CH₂—CO₂C₂H₅ | H | 2-(—CH₂—S—)-5-NO₂-pyridine |
| (phenyl)₃C— | —CH₂—CONH₂ | H | H | 2-(—CH₂—S—)-5-NO₂-pyridine |
| H | —CH(C₆H₅)—COOH | H | H | 2-(—CH₂—S—)-5-NO₂-pyridine |
| H | —C(C₆H₅)(CO₂H)— | H | H | 2-(—CH₂—S—)-3-CH₃-pyridine-6-COOH |
| H | —CH₂—C₆H₄(3-CH₃) | —CH₂—O—C(=O)—C(CH₃)₃ | H | 2-(—CH₂—S—)-3-CH₃-pyridine-6-COOH |

| R₁ | R₂ | R₃ | R₄ | A |
|---|---|---|---|---|
| H | -CH₂-C(=O)-N(morpholine) | H | H | -CH₂S-(3-methylpyridine N-oxide) |
| H | -CH₂-C(=O)-N(CH₃)₂ | H | H | -CH₂S-(2-COOH pyridine N-oxide) |
| H | -CH₂-COOCH₃ | H | H | -CH₂S-(pyridine with COOCH₃, N-oxide) |
| H | -CH₂-CH₃ | H | H | -CH₂S-(COOH-pyridine N-oxide) |
| H | -CH₃ | H | H | -CH₂S-(4-methylpyrimidine) |
| H | -CH₂-(4-NO₂-phenyl) | H | H | -CH₂S-(4,6-dimethylpyrimidine) |

-continued
| R1 | R2 | R3 | R4 | A |
|---|---|---|---|---|
| H | —CH2—CH3 | | H |  |
| Br—CH2—C(=O)— | —CH3 | —CH2—O—C(CH3)2—C(CH3)3 | H |  |
| H | —C(=O)—CH2Cl | H | OCH3 |  |
| H | H |  | H |  |
| H | —CH2—CH=CH—CH3 | H | H |  |
| H | —CH(CH3)2 | H | H |  |
|  | H | H | H |  |

-continued

| R1 | R2 | R3 | R4 | A |
|---|---|---|---|---|
| H₃C—C(=O)— | —CH₂—CH=CH—CH₃ | H | H | —CH₂—S—[pyrimidine: CH₃, N, OCH₃(as CH₃ per image), CH₃]... —CH₂—S-(4,6-dimethylpyrimidin-2-yl) |
| H | —CH(CH₃)—COOH | H | H | —CH₂—S-(4,6-dimethylpyrimidin-2-yl) |
| H | —CH₃ | —CH(OCH₃)—CO₂CH₃ | H | —CH₂—S-(4,6-dimethylpyrimidin-2-yl) |
| H | H | H | OCH₃ | —CH₂—S-(4-methyl-6-ethoxypyrimidin-2-yl) |
| Ph-CH₂—C(=O)— | —C(=O)—CH₃ | H | H | —CH₂—S-(4-methyl-6-ethoxypyrimidin-2-yl) |
| H | —CH₂—C≡CH | H | H | —CH₂—S-(4-methyl-6-(H₅C₂O₂C—CH₂)-pyrimidin-2-yl) |
| H | —CH₂—CH₂—O—CH₃ | —CH₂—CO₂C₂H₅ | H | —CH₂—S-(4-methyl-6-(H₅C₂O₂C—CH₂)-pyrimidin-2-yl) |

| R₁ | R₂ | R₃ | R₄ | A |
|---|---|---|---|---|
| PhCH₂-O-C(=O)- | -CH₂-CH₂-CH₃ | H | H | -CH₂-S-[pyrimidine with CH₂-COOH and N-CH(CH₃)-] |
| H | cyclohexyl-COOH | H | H | -CH₂-S-[pyrimidine with CH₂-COOH and N-CH(CH₃)-] |
| H | -CH(CH₃)₂ | H | H | -CH₂-S-[pyrimidine with N-morpholino] |
| H | -CH(C₂H₅)-CO₂C₂H₅ | H | H | -CH₂-S-[pyrimidine with N-morpholino] |
| H | thiophene-C(=O)- | -CH(CH₃)₂ | H | -CH₂-S-[pyrimidine with N-morpholino] |
| H | H | H | H | -CH₂-S-[pyrimidine] |
| H | CH₃ | H | OCH₃ | -CH₂-S-[pyrimidine] |

-continued

| R₁ | R₂ | R₃ | R₄ | A |
|---|---|---|---|---|
| H | —CH₂—CH₂—CH₃ | —C(CH₃)₃ | H | —CH₂—S—(pyrimidine) |
| Cl—CH₂—C(=O)— | —CH₂—CH₃ | H | H | —CH₂—S—(pyrimidine) |
| H | —CH₂—C₆H₅ | H | H | —CH₂—S—(pyrimidine-CH₃) |
| H | —CH₂—SO₃H | H | H | —CH₂—S—(pyrimidine-CH₃) |
| H | —CH₂—CH₂—OH | H | OCH₃ | —CH₂—S—(pyrimidine-OH) |
| H | —CH₂—CH₂—CH₂—CH₃ | H | H | —CH₂—S—(pyrimidine-OH) |
| H | H | H | H | —CH₂—S—(pyrimidine-O-CH₂—COOH) |
| C₆H₅—CH₂— | —CH₃ | H | H | —CH₂—S—(pyrimidine-OCH₂—COOH) |

-continued
| $R_1$ | $R_2$ | $R_3$ | $R_4$ | A |
|---|---|---|---|---|
| H | 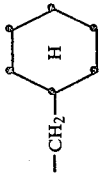 | H | H | 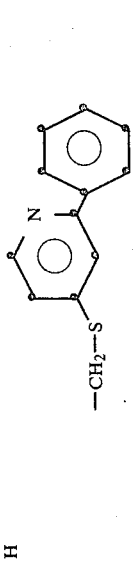 |
| H | —CH$_2$—CH$_3$ |  | H | 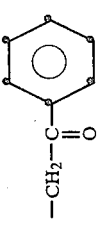 |
| H | 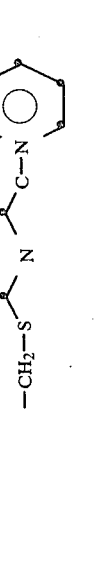 | H | H |  |
| H | —CH$_3$ | H | H | 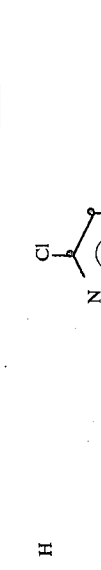 |
| H | —CH$_2$CH$_3$ | H | H |  |
| H | H | H | H | 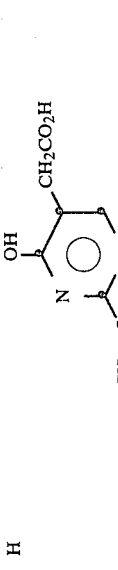 |
| Cl—CH$_2$—C(=O)— | —CH$_3$ | H | H |  |

| R₁ | R₂ | R₃ | R₄ | A |
|---|---|---|---|---|
| H | —CH₃ | H | H | —CH₂—S—[pyridine ring with OH, CH₂—COOH, CH₃] |
| H | —CH₂—CH₃ | [phthalide ring] | H | —CH₂—S—[pyridine ring with OH, CH₂—CH₂—CN, CH₃] |
| H | —CH₂—CH₂—CH₃ | H | H | —CH₂—S—[pyridine ring with OH, CH₂—COOH, CH₃] |
| H | —CH—COOH (with cyclopentyl) | H | H | —CH₂—S—[pyridine ring with CH₂—COOC₂H₅, CH₃] |
| H | —CH₂—CH₃ | H | OCH₃ | —CH₂—S—[pyridine ring] |
| H | —CH₂—[phenyl-OCH₃] | H | H | —CH₂—S—[pyridine ring with OH, COOH] |
| H | —CH₂—CH=CH₂ | —CH₂—O—C(=O)—C(CH₃)₃ | H | —CH₂—S—[pyridine ring with OH, C(=O)N-morpholine] |

-continued

| R₁ | R₂ | R₃ | R₄ | A |
|---|---|---|---|---|
| H | H | H | —CH₂—S— | (1,2,3-thiadiazol-5-yl)thio via CH₂—S |
| H | —C₂H₅ | H | —OCH₃ | (1,2,3-thiadiazol-5-yl)thio via —CH₂—S |
| H | —CH₂—C≡CH | —C(CH₃)₂—CH₂—CH₃ | H | (1,2,3-thiadiazol-5-yl)thio via —CH₂—S |
| (C₆H₅)₂CH— | —CH₂—C(=O)—N(morpholino) | H | H | (1,2,3-thiadiazol-5-yl)thio via —CH₂—S |
| H | —CH(C₃H₇)—COOH | H | H | (1,3-thiazol-2-yl)thio via —CH₂—S |
| H | —CH₃ | H | H | (1,3-thiazol-2-yl)thio via —CH₂—S |
| C₆H₅—O—CH₂—C(=O)— | —CH₂—SO₂NH₂ | H | H | (1,3-thiazol-2-yl)thio via —CH₂—S |
| H | —CH₂—CH₂—S—CH₃ | phthalidyl | H | (1,3-thiazol-2-yl)thio via —CH₂—S |

-continued

| R₁ | R₂ | R₃ | R₄ | A |
|---|---|---|---|---|
| H | -CH(CH₃)(CH₃) | -Si(CH₃)₃ | H | -CH₂-S-[thiadiazole] |
| Cl-CH₂-C(=O)- | -CH₃ | | H | -CH₂-S-[thiadiazole] |
| H | -CH₂-COOH | | H | -CH₂-S-[thiadiazole] |
| H | -CH(-COOH)(cyclopentyl) | -CH₂-C₆H₄-NO₂ | H | -CH₂-S-[thiadiazole] |
| H | (cyclopropyl)-COOH | H | OCH₃ | -CH₂-S-[thiadiazole] |
| H | -CH₂-CH=CH-CH₃ | H | H | -CH₂-S-[thiadiazole] |
| H | H | -CH₂-C(=O)-furyl | H | -CH₂-S-[oxadiazole] |
| H | -CH₂-CH₂-SO₃C₂H₅ | H | H | -CH₂-S-[oxadiazole] |
| H | -CH₂-CH₂-OH | H | OCH₃ | -CH₂-S-[oxadiazole] |

-continued
| $R_1$ | $R_2$ | $R_3$ | $R_4$ | A |
|---|---|---|---|---|
| 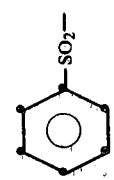 | —CH$_3$ | 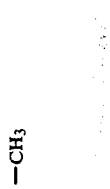 | H | 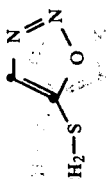 |
| CCl$_3$—C(=O)— | —CH$_2$—CO$_2$CH$_3$ | H | H | 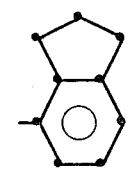 |
| H | H | H | H |  |
| H |  | H | OCH$_3$ |  |
| H |  | H | H | 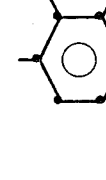 |
| H | —CH$_3$ |  | H | 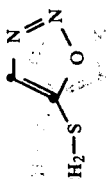 |
|  | 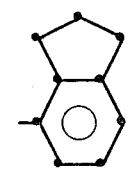 | H | H |  |

-continued

| R₁ | R₂ | R₃ | R₄ | A |
|---|---|---|---|---|
| Br—CH₂—C(=O)— | —CH₂—CH₂—CH₂—CH₃ | H | H | —CH₂—S—C(=N-benzo)O— |
| H | —CH₂—C(=O)—NH—CH₃ | —CH₂—O—C(CH₃)₃(C=O) | H | —CH₂—S—C(=N-benzo)O— |
| H | H | H | H | —CH₂—S—C(=N)O— (phenyl) |
| H | —CH₃ | H | H | —CH₂—S—C(=N)O— (phenyl) |
| H | —CH₂—(phenyl) | —C(CH₃)₂—CH₃ | H | —CH₂—S—C(=N)O— (phenyl) |
| H | —CH₂—CO₂C(CH₃)₃ | —CH₂O—C(=O)—CH₃ | —OCH₃ | —CH₂—S—C(=N)O— (phenyl) |
| (phenyl)—O—CH₂—C(=O)— | —CH(CH₃)₂ | H | H | —CH₂—S—C(=N)O— (phenyl) |
| HC(=O)— | —C(CH₃)₃ | —C₁₂H₂₅ | H | —CH₂—S—C(=N)O— (phenyl) |
| H | | | H | —CH₂—S—C(=N)O— (oxazoline) |

| $R_1$ | $R_2$ | $R_3$ | $R_4$ | A |
|---|---|---|---|---|
| $H_3C-\overset{O}{\underset{\|}{C}}-$ | $-CH_3$ | H | H | $-CH_2-S-\underset{N}{\overset{\diagup\diagdown}{C}}\underset{\diagdown\diagup}{O}$ |
| ⟨C(CH₃)₃-phenyl⟩ | $CH_2-CH_2-O-CH_3$ | H | H | $-CH_2-S-\underset{N}{\overset{\diagup\diagdown}{C}}\underset{\diagdown\diagup}{O}$ |
| H | H | H | H | $-CH_2-S-\underset{N}{\overset{\diagup\diagdown}{C}}\underset{\diagdown\diagup}{N-H}$ |
| H | $-CH_2-CH_3$ | H | $OCH_3$ | $-CH_2-S-\underset{N}{\overset{\diagup\diagdown}{C}}\underset{\diagdown\diagup}{N-H}$ |
| H | $\underset{CH_3}{\overset{CH_3}{\underset{\|}{\overset{\|}{-C-}}}}CH_3$ | $-CH_2-CN$ | H | $-CH_2-S-\underset{N}{\overset{\diagup\diagdown}{C}}\underset{\diagdown\diagup}{N-H}$ |
| H | $-CH_2-CH=CH_2$ | $-CH-CO_2CH_3$ $\underset{\|}{OCH_3}$ | H | $-CH_2-S-\underset{N}{\overset{\diagup\diagdown}{C}}\underset{\diagdown\diagup}{N-H}$ |
| $Cl-CH_2-\overset{O}{\underset{\|}{C}}-$ | $-CH-COOH$ $\underset{\|}{CH_3}$ | H | H | $-CH_2-S-\underset{N}{\overset{\diagup\diagdown}{C}}\underset{\diagdown\diagup}{N-H}$ |
| ⟨phenyl-CH₂-O-C(=O)-⟩ | ⟨cyclohexyl-COOH⟩ | H | H | $-CH_2-S-\underset{N}{\overset{\diagup\diagdown}{C}}\underset{\diagdown\diagup}{N-H}$ |

-continued

| R₁ | R₂ | R₃ | R₄ | A |
|---|---|---|---|---|
| H | -CH₂-C₆H₄-NO₂ (p-nitrobenzyl) | H | H | -CH₂-S-C(=N)-NH-CH₂-CH₂- (cyclic, 2-imidazoline-2-yl-thiomethyl) |
| C₆H₅-CH₂- | -CH₂-CH₂-S-CH₃ | H | H | -CH₂-S-C(=N)-NH-CH₂-CH₂- |
| H | -CH₂-CO₂CH₃ | -CH₂-CO₂CH₃ | H | -CH₂-S-C(=N)-NH-CH₂-CH₂- |
| C₆H₅-O-CH₂-C(=O)- | -CH₃ | (3-methylphthalide group) | -OCH₃ | -CH₂-S-C(=N)-N(CH₃)-CH₂-CH₂- |
| H | H | -CH₂-O-C(=O)-C(CH₃)₃ | H | -CH₂-S-C(=N)-N(CH₃)-CH₂-CH₂- |
| H | -CH(cyclopropyl)-COOH | H | H | -CH₂-S-C(=N)-N(CH₃)-CH₂-CH₂- |
| H | H | H | H | -CH₂-S-C(=N-C₆H₄)-NH- (benzimidazol-2-yl-thiomethyl) |

-continued
| R₁ | R₂ | R₃ | R₄ | A |
|---|---|---|---|---|
| H |  | H | OCH₃ |  |
| H | —CH—COOH<br>    \|<br>    C₂H₅ | H | H |  |
| H | —SO₂—CH₃ | H | H |  |
| H | —CH₂—CO₂—C(CH₃)₃ | —CH₂—O—C—CH₃<br>           ||<br>           O | H |  |
| H | —CH₃ | CH₃<br> |<br>CH₃—C—CH₃ | H |  |
| H | —C—CHCl₂<br>  ||<br>  O |  | —OCH₃ |  |
| C₄H₉—C—<br>     ||<br>     O |  | H | H |  |

-continued

| $R_1$ | $R_2$ | $R_3$ | $R_4$ | A |
|---|---|---|---|---|
| $(H_3C)_3C-O-\overset{\|}{\underset{\|}{C}}=O$ | $-\overset{\|}{\underset{\|}{C}}-CH_2-N(CH_3)_2$ | H | H |  |
| H | $-CH-COOH$ <br>  | H | $-OCH_3$ |  |
| H | H | H | H |  |
| H | $-CH_2-CH=CH_2$ | $-CH-CO_2CH_3$ <br> $\|$ <br> $OCH_3$ | H |  |
| H |  | H | H |  |
| $H_3C-\langle\bigcirc\rangle-SO_2-$ | $-CH_2-CH=CH-CH_3$ | H | H |  |
| H | $\overset{CH_3}{\underset{CH_3}{\overset{\|}{C}}}-\overset{CH_3}{\underset{\|}{C}}$ |  | H |  |
| H | $-CH_3$ | $-CH_2-O-\overset{\|}{\underset{\|}{C}}-CH_3$ <br> $\overset{\|}{O}$ | H |  |
| $Cl-CH_2-\overset{\|}{\underset{\|}{C}}=O$ | $-CH_2-CH_2-CH_3$ | H | H |  |
| H | | | |  |

-continued

| R₁ | R₂ | R₃ | R₄ | A |
|---|---|---|---|---|
| H | $-CH_2-CO_2C(CH_3)_3$ | $-C(CH_3)_3$ (C with three CH₃) | H | $-CH_2-S$ attached to thiadiazole (N=N/S) |
| ![phenyl-O-CH₂-C(=O)-] (C₆H₅-O-CH₂-C(=O)-) | $-CH_3$ | H | H | $-CH_2-S$ attached to thiadiazole (N=N/S) |
| H | H | H | H | $-CH_2-S$ attached to pyrazine |
| H | $-CH-COOH$ with cyclopropyl | H | H | $-CH_2-S$ attached to pyrazine |
| H | $-CH_2-$phenyl | H | H | $-CH_2-S$ attached to pyrazine |
| [cyclohexyl-C(CH₃)₃ group] | $-CH(CH_3)_2$ | $-CH_2-O-C(=O)-CH_3$ | H | $-CH_2-S$ attached to pyrazine |
| H | H | H | H | $-CH_2-S$ attached to N-N ring with CH₃, OH substituents |
| H | $-CH_2-CO_2CH_3$ | H | $OCH_3$ | $-CH_2-S$ attached to N-N ring with CH₃, OH substituents |

-continued

| R₁ | R₂ | R₃ | R₄ | A |
|---|---|---|---|---|
| H | —CH₂—CH=CH₂ | —CH—CO₂CH₃<br>    \|<br>   OCH₃ | H | ![triazine with CH₃, OH, N-N, CH₂-S]—CH₂—S-(triazine: N=N, C-CH₃, C-OH) |
| ![phenyl-CH(C₃H₇)—] | —C₂H₅ | —CH₂—CO₂C₂H₅ | H | —CH₂—S-(triazine as above) |
| Br—CH₂—C(=O)— | —CH(CH₃)-(4-Cl-C₆H₄) | H | H | —CH₂—S-(triazine as above) |
| H | —CH₃ | —C(CH₃)₃ | H | —CH₂—S-(triazine with S—CH₃, N, phenyl, N) |
| H | —CH(CH₃)—COOH | —CH₂—O—C(=O)—CH₃ | H | —CH₂—S-(triazine with S—CH₃, phenyl) |
| H₃C—C(=O)— | —CH₂—CONH₂ | H | H | —CH₂—S-(triazine with S—CH₃, phenyl) |

-continued
| R₁ | R₂ | R₃ | R₄ | A |
|---|---|---|---|---|
| H | —CH₂—CH=CH—CO₂H | —CH₂—O—C(=O)—CH₃ | H | 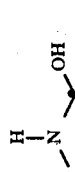 |
| H | —CH₃ | H | H | 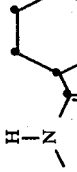 |
| Cl—CH₂—C(=O)— | —CH₂—CH₂—S—CH₃ | H | H | 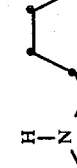 |
|  | (CH₃)₂CH— | H | H |  |
| H | cyclopentyl-COOH | —CH(CH₃)₂ | H |  |
| H | —CH₂—CH=CH₂ | —CH₂—O—C(=O)—C(CH₃)₃ | H |  |

-continued

| R₁ | R₂ | R₃ | R₄ | A |
|---|---|---|---|---|
| H | —CH₃ | —C(CH₃)₃ | H | —CH₂—S— (imidazo-pyrimidine-NH) |
| Ph—O—CH₂—C(=O)— | —CH(CO₂C₂H₅)—C₃H₇ | | H | —CH₂—S— (imidazo-pyrimidine-NH) |
| Cl—CH₂—C(=O)— | —CH(CH₃)₂ | H | H | —CH₂—S— (pyrimidine-C(=NH)—NH) |
| H | —CH₂—CH=CH₂ | —CH₂—CO₂C₂H₅ | H | —CH₂—S— (pyrimidine-C(=NH)—NH) |
| H | —CH(cyclopentyl)—COOH | —CH₂—C₆H₄—NO₂ | H | —CH₂—S— (pyrimidine-C(=NH)—NH) |

The above table also relates to compounds of the general formula XII which contain a —SO$_2$ group instead of the —SO group.

The compounds of the general formula I in which R$_1$ represents hydrogen, R$_2$ represents hydrogen, alkyl with 1–4 C atoms, preferably methyl, ethyl, propyl or butyl, alkenyl with 3–4 C atoms, such as, for example, allyl, or alkyl with 1–4 C atoms which is substituted by carboxyl or alkoxycarbonyl with 1–4 C atoms in the alkoxy radical, in particular carboxymethyl, methoxycarbonylmethyl and ethoxycarbonylmethyl, R$_3$ represents hydrogen, a cation, preferably an alkali metal, in particular sodium, or an ester group, preferably acyloxymethyl, carboxyalkyl or phthalide, R$_4$ represents hydrogen, X represents SO and A represents acetoxymethyl or the group —SR$_5$, R$_5$ having the preferred meanings indicated above, are particularly interesting according to the invention.

The following embodiment examples of syn-compounds which can be manufactured according to the invention serve to further illustrate the invention but do not limit it thereto.

EXAMPLE 1

The 1-S-oxide of 7-[2-(2-tritylaminothiazol-4-yl)-2-methoxyimino-acetamino]-cephalosporanic acid 7 g (0.01 mole) of 7-[2-(2-tritylaminothiazol-4yl)-2-methoxyimino-acetamino]-cephalosporanic acid are dissolved in 25 ccs of tetrahydrofuran. A solution of 2.1 g (0.012 mole) of 3-chloroperoxybenzoic acid in 6 ccs of tetrahydrofuran is added dropwise at 10° C., while stirring, and the solution is further stirred for one hour and poured into 750 ccs of ether. 5.1 g of the title compound precipitate and are washed with ether and are dried in vacuo over phosphorus pentoxide. Decomposition point: from 160° C.

R$_f$ value: 0.51 (Merck thin layer chromatography silica gel, ethyl acetate/i-propanol/water 4:3:2).

NMR (ppm, 60 MHz, (CD$_3$)$_2$SO): 2.05 (3H, s, CH$_3$—CO), 3.88 (3H, s, —OCH$_3$), 6.85 (1H, s, aromatic H) and 7.4 (15 H, trityl-H).

Neutral salts of the alkali metal series and alkaline earth metal series and salts with aromatic bases are obtained by bringing together equivalent amounts of one of these bases and the title compound in water and freeze-drying the filtered solution.

A crystalline sodium salt was obtained as follows: 1.2 g of freeze-dried sodium salt is dissolved in 50 ccs of methanol, the solution is filtered with charcoal and ether is added to the filtrate until the solution starts to become turbid. On trituration, 0.8 g of the sodium salt of the 1-S-oxide of 7-[2-(2-aminothiazol-4-yl)-2-methoxyimino-acetamino]-cephalosporanic acid crystallizes out as the dihydrate:

C$_{16}$H$_{16}$N$_5$NaO$_8$S$_2$.2H$_2$O (529.4). Calculated: C, 36.3; H, 3.8; N, 13.2; S, 12.1. Found: C, 36.2; H, 3.8; N, 13.4; S, 12.0.

EXAMPLE 2

The 1-S-oxide of 7-[2-(2-aminothiazol-4-yl)-2-methoxyimino-acetamino]-cephalosporanic acid (a) 5 g (0.007 mole) of the 1-S-oxide of 7-[2-(2-tritylaminothiazol-4-yl)-2-methoxyimino-acetamino]-cephalosporanic acid (Example 1) are introduced into 30 ccs of 50% strength aqueous formic acid at 50° C., while stirring, the mixture is further stirred for 20 minutes and cooled to room temperature and the triphenylcarbinol is filtered off and rinsed with about 100 ccs of water. On cooling the filtrate, 1.3 g of the title compound crystallize out.

(b) 12.8 g (0.028 mole) of 7-[2-(2-aminothiazol-4-yl)-2-methoxyimino-acetamino]-cephalosporanic acid are dissolved in 85 ccs of formic acid, and 28 ccs of methanol are added. A solution of 5.0 g (0.029 mole) of 3-chloroperoxybenzoic acid in 28 ccs of tetrahydrofuran is added dropwise at room temperature, while stirring, the reaction mixture is further stirred for 50 minutes and poured into 1 l of ether and the precipitate is filtered off. For further purification, the precipitate is dissolved in 45 ccs of formic acid, a mixture of 1 l of methanol and 330 ccs of water is added and, after cooling with ice for half an hour, the crystalline product is filtered off, washed with methanol and dried.

10.5 g of the title compound are obtained.

(c) 5.2 g (0.01 mole) of the formate of 7-[2-(2-aminothiazol-4-yl)-2-methoxyimino-acetamino]-cephalosporinic acid (monohydrate) are dissolved in a mixture of 50 ccs of tetrahydrofuran and 10 ccs of water. A solution of 2.5 g of 82% strength 3-chloro-peroxybenzoic acid (corresponding to 0.012 mole) in 6 ccs of tetrahydrofuran is added dropwise at 10° C., whilst stirring. Some of the reaction product already crystallizes out during the dropwise addition. After stirring for one hour, the precipitate is filtered off, washed with tetrahydrofuran and dried in vacuo. 3.2 g of the 1-S-oxide of 7-[2-(2-aminothiazol-4-yl)-2-methoxyimino-acetamino]-cephalosporanic acid are obtained. The compound slowly becomes discolored from 170° and decomposes completely above 300°. It can optionally be recrystalized from a mixture of formic acid/methanol/H$_2$O.

C$_{16}$H$_{17}$N$_5$O$_8$S$_2$×H$_2$O (489.5). Calculated: C, 39.2; H, 3.9; N, 14.3; S, 13.1. Found: C, 39.4; H, 3.9; N, 14.2; S, 13.3.

NMR (ppm, 60 MHz, (CD$_3$)$_2$SO): 2.05 (3H, S, CH$_3$CO), 3.77 (2H, q, 2—CH$_2$), 3.88 (3H, S, O—CH$_3$), 4.90 (2H, q, 3—C—CH$_2$O), 4.97 (1H, d, 6—H), 5.92 (1H, q, 7—H), 6.85 (1H, S, aromatic H), 7.17 (2H, S, —NH$_2$) and 8.85 (1H, d, CONH—).

R$_f$ value: 0.34 (Merck thin layer chromatography silica gel/ethyl acetate/i-propanol/water 4:3:2), R$_f$ of the starting compound: 0.46.

EXAMPLE 3

The 1-S-oxide of 7-[2-ethoxyimino-2-(2-aminothiazol-4-yl)acetamino]-cephalosporanic acid Stage 1: 7.1 g (0.01 mole) of 7-[2-ethoxyimino-2-(2-tritylaminothiazol-4-yl)-acetamino]-cephalosporanic acid are dissolved in 16 ccs of tetrahydrofuran, and a solution of 1.7 g (0.01 mole) of 3-chloroperoxybenzoic acid in 5 ccs of tetrahydrofuran is added dropwise at 20° C., while stirring. After stirring for one hour, the reaction mixture is poured into 300 ccs of ether. 7.2 g of the 1-S-oxide of 7-[2-ethoxyimino-2-(2-tritylaminothiazol-4-yl)-acetamino]-cephalosporanic acid precipitate and are washed with ether and dried in air. This compound can be used for stage 2 without further purification.

Stage 2: 7.2 g of the 1-S-oxide of 7-[2-ethoxyimino-2-(2-tritylaminothiazol-4-yl)-acetamino]-cephalosporanic acid are dissolved in 32 ccs of 80% strength aqueous formic acid, the solution is stirred at room temperature for two hours, 25 ccs of water are added, the triphenylcarbinol is filtered off and the filtrate is concentrated in vacuo. On trituration with ethanol and standing in a refrigerator, the amorphous residue becomes crystalline. After filtering off and drying in vacuo, 2.7 g of the 1-S-oxide of 7-[2-ethoxyimino-2-(2-aminothiazol-4-yl)-acetamino]-cephalosporanic acid, which slowly decomposes above 250° C., are obtained.

$C_{17}H_{19}N_5O_8S_2 \times 1H_2O$ (503.5) Calculated: C, 40.6; H, 4.2; N, 13.9; S, 12.7, Found: C, 40.7; H, 4.1; N, 13.7; S, 13.2.

NMR (ppm, 60 MHz, $(CD_3)_2SO$): 1.27 (3H, t, C—$CH_3$), 2.07 (3H, S, $COCH_3$), 3.77 (2H, q, 2—$CH_2$), 4.13 (2H, q, O—$CH_2$—), 4.90 (2H, q, 3—C—$CH_2$—O), 4.97 (1H, d, 6—H), 5.92 (1H, q, 7—H), 6.80 (1H, S, aromatic H), 7.17 (2H, S, —$NH_2$) and 8.67 (1H, d, CONH—).

EXAMPLE 4

The 1-S-oxide of 7-[2-(2-aminothiazol-4-yl)-2-propoxyimino-acetamino]-cephalosporanic acid Stage 1: 68 g (0.43 mole) of ethyl 2-hydroxyimino-acetoacetate are dissolved in 350 ccs of acetone, 70.7 g of anhydrous potassium carbonate and 58.9 g (0.43 mole) of propyl mesylate are added and the mixture is boiled under reflux for 9 hours. The salts are filtered off and rinsed with acetone, the solution is concentrated, the residue is taken up in methylene chloride and the methylene chloride solution is washed with sodium carbonate solution and water. Drying and concentrating the methylene chloride solution leaves 70 g of ethyl 2-propoximino-acetoacetate as an oil.

Stage 2: One tenth of a solution of 17.8 ccs (0.35 mole) of bromine in 70 ccs of methylene chloride is added to 70 g (0.35 mole) of ethyl 2-propoxyimino-acetoacetate in 350 ccs of methylene chloride at 25° C., while stirring and irradiating with UV light. After the bromine layer has disappeared, the rest of the bromine solution is slowly added dropwise. The mixture is further stirred for 30 minutes and poured onto ice and the organic phase is separated, washed until neutral and concentrated.

85 g of ethyl 4-bromo-2-propoxyimino-acetoacetate are obtained as an oil.

Stage 3: 85 g of ethyl 4-bromo-2-propoxyimino-acetoacetate are added dropwise to 23 g (0.3 mole) of thiourea in 155 ccs of water and 75 ccs of ethanol at 25°, while stirring. After one hour, the hydrobromide which has precipitated in the meantime is decomposed by adding concentrated ammonia up to pH 6. After filtering off the product, washing with water and diisopropyl ether and drying, 45 g of ethyl 2-(2-aminothiazol-4-yl)-2-propoxyimino-acetate are obtained.

NMR (ppm, 60 MHz, $(CD_3)_2SO$): 0.77–1.8 (8H, m, $2 \times CH_3$, —$CH_2$—), 3.9–4.5 (4H, $2 \times$—O—$CH_2$), 6.97 (1H, S, aromatic H) and 7.27 (2H, S, $NH_2$).

Stage 4: 30 ccs of triethylamine are added to 45 g (0.18 mole) of ethyl 2-(2-aminothiazol-4-yl)-2-propoxyimino-acetate in 120 ccs of dimethylformamide and 175 ccs of methylene chloride, and 59 g (0.21 mole) of trityl chloride (97% pure) are introduced in portions. After stirring the mixture for four hours, 175 ccs of methylene chloride are added and the organic phase is washed with water until free from chlorine ions. The dried solution gives, after concentrating, 90 g of ethyl 2-propoximino-2-(2-tritylaminothiazol-4-yl)-acetate, which is employed for the next stage without purification.

Stage 5: 90 g (0.18 mole) of ethyl 2-propoxyimino-2-(2-tritylaminothiazol-4-yl)-acetate are dissolved in 420 ccs of dioxan, 105 ccs (0.21 mole) of 2N sodium hydroxide solution are added dropwise at 85°, while stirring, and the mixture is kept at this temperature for one hour. On cooling, the sodium salt of 2-propoxyimino-2-(2-tritylaminothiazol-4-yl)-acetic acid crystalline out. It is filtered off, washed with a mixture of dioxan/ether 1:1 and then with acetone and dried at 80° C. The acid is liberated by suspending the sodium salt in chloroform, adding the equivalent amount of 1N hydrochloric acid, shaking the mixture and washing the chloroform solution with water. After stripping off the solvent, 46 g of 2-propoxyimino-2-(2-tritylaminothiazol-4-yl)-acetic acid, which still contains some chloroform but is employed directly for the coupling with 7-aminocephalosporanic acid, are obtained.

Stage 6: 46 g (0.088 mole) of 2-propoxyimino-2-(2-tritylaminothiazol-4-yl)-acetic acid (90% pure) in 120 ccs of chloroform are added dropwise to a solution, cooled to +5°, of 10.7 g of dicyclohexylcarbodiimide in 70 ccs of chloroform, while stirring. After stirring for two hours, the dicyclohexylurea which has precipitated is separated. A solution of 11.9 g of 7-aminocephalosporanic acid and 150 ccs of triethylamine in 180 ccs of methylene chloride is added dropwise to the filtrate, which has been cooled to −10° C., while stirring. After stirring the mixture is at room temperature for three hours, it is carefully acidified with 110 ccs of 1 N hydrochloric acid, unreacted 7-aminocephalosporanic acid is filtered off and the filtrate is washed with water until neutral, dried and concentrated. The residue (about 60 g) is dissolved in 110 ccs of dioxan, the solution is filtered with a little charcoal, and 110 ccs of ether and 13.5 ccs of diethylamine are added to the filtrate. On cooling in ice, 19 g of the diethylamine salt of 2-propoxyimino-2-(2-tritylaminothiazol-4-yl)-acetic acid are precipitated as crystals. After stripping off the solvent, 42 g of residue remain which, when triturated with ether, give 27 g of the crude diethylamine salt of the coupling product. A solution of this salt in 300 ccs of solution is shaken with the equivalent amount of 1N hydrochloric acid, the reaction mixture is added with water until neutral, dried and filtered with charcoal and the filtrate is concentrated. When triturated with ether and dried, the residue gives 20 g of 7-[2-propoxyimino-2-(2-tritylaminothiazol-4-yl)-acetamino]-cephalosporanic acid.

Stage 7: 4.4 g (0.006 mole) of 7-[2-propoxyimino-2-(2-tritylaminothiazol-4-yl)-acetamino]-cephalosporanic acid are dissolved in 25 ccs of 80% strength aqueous formic acid and the solution is stirred at room temperature for 2 hours. On adding 25 ccs of water, triphenylcarbinol precipitates. The filtrate is concentrated and the residue is triturated with ether and dried.

2.3 g of 7-[2-(2-aminothiazol-4-yl)-2-propoxyimino-acetamino]-cephalosporanic acid, which slowly decomposes from 120°, are obtained.

Stage 8: 14.5 g (0.02 mole) of stage 6 are dissolved in 35 ccs of tetrahydrofuran and a solution of 4.85 g (0.022 mole) of 3-chloroperoxybenzoic acid (78.3% pure) in 10 ccs of tetrahydrofuran is added at 20° C. After stirring for one hour, the mixture is poured into 1 l of ether and the precipitate is filtered off and dried. 11.6 g of the 1-S-oxide of 7-[2-propoxyimino-2-(2-tritylaminothiazol-4-yl)-acetamino]-cephalosporanic acid are obtained, the trityl group of which is split off analogously to Example 4, stage 7 using 80% strength formic acid. 6.3 g of the 1-S-oxide of 7-[2-(2-aminothiazol-4-yl)-2-propoxyimino-acetamino]-cephalosporanic acid are obtained:

$C_{18}H_{21}N_5O_8S_2 \cdot \frac{1}{2}H_2O$ (508.5). Calculated: C, 42.5; H, 4.4; N, 13.8; S, 12.6. Found: C, 42.5; H, 4.4; N, 13.5; S, 12.4.

NMR (ppm, 60 MHz, $(CD_3)_2SO$): 0.93 (3H, t, —CH$_2$—$\underline{CH_3}$), 1.66 (2H, m, —CH$_2$—$\underline{CH_2}$—CH$_3$), 2.07 (3H, S, CH$_3$CO), 3.9 (2H, q, 2—CH$_2$), 4.07 (2H, t, O—$\underline{CH_2}$—CH$_2$—), 4.93 (2H, q, 3—C—$\underline{CH_2}$—O), 5.0 (1H, d, 6—H), 5.93 (1H, q, 7—H), 6.80 (1H, s, aromatic H), 7.2 (2H, s, —NH$_2$) and 8.67 (1H, d, CONH—).

EXAMPLE 5

The 1-S-oxide of 7-[2-(2-aminothiazol-4-yl)-2-n-butoxyimino-acetamino]-cephalosporanic acid Stage 1: Analogously to Example 4, stage 1, 79.5 g (0.5 mole) of ethyl 2-hydroxyimino-acetoacetate and 68.3 g (0.45 mole) of n-butyl mesylate give 76 g of ethyl 2-n-butoxyimino-acetoacetate as a colorless oil.

NMR (ppm, 60 MHz, $(CD_3)_2SO$): 0.9–1.8 (10H, m, —CH$_2$—$\underline{CH_3}$, —CH$_2$—CH$_2$—CH$_3$), 2.4 (3H, s, CH$_3$—CO) and 4.1–4.6 (4H, t+q, 2×—O—CH$_2$—).

Stage 2: 76 g (0.35 mole) of ethyl 2-n-butoxyimino-acetoacetate and 18 ccs (0.35 mole) of bromine react analogously to Example 4, stage 2, to give 93 g of ethyl 4-bromo-2-n-butoxyimino-acetoacetate.

Stage 3: 93 g (0.32 mole) of ethyl 4-bromo-2-n-butoxyimino-acetoacetate and 24 g (0.32 mole) of thiourea undergo a condensation reaction analogously to Example 4, stage 3, to give 35.2 g of ethyl 2-(2-aminothiazol-4-yl)-2-n-butoxyimino-acetate of melting point 129.5°–131°.

Stages 4 and 5: 35.2 g (0.13 mole) of ethyl 2-(2-aminothiazol-4-yl)-2-n-butoxyimino-acetate are tritylated with 44.6 g (0.155 mole) of trityl chloride (97% pure) analogously to Example 4, stage 4, and the product is split, without further purification, as described in Example 4, stage 5, to give 37 g of 2-n-butoxyimino-2-(2-tritylaminothiazol-4-yl)-acetic acid.

Stage 6: 37 g of 2-n-butoxyimino-2-(2-tritylaminothiazol-4-yl)-acetic acid are coupled with 7-aminocephalosporanic acid analogously to Example 4, stage 6. The crude diethylamine salt of the coupling product was dissolved in 500 ccs of water, the solution was filtered with charcoal and the filtrate was acidified with 1N hydrochloric acid and extracted with chloroform. The extract was dried and concentrated and the residue was treated with ether. 10.5 g of 7-[2-n-butoxyimino-2-(2-tritylaminothiazol-4-yl)-acetamino]-cephalosporanic acid are obtained.

Stage 7: 3.7 g (0.005 mole) of 7-[2-n-butoxyimino-2-(2-tritylaminothiazol-4-yl)-acetamino]-cephalosporanic acid (stage 6) were detritylated analogously to Example 4, stage 7, to give 1 g of crystalline 7-[2-(2-aminothiazol-4-yl)-2-n-butoxyimino-acetamino]-cephalosporanic acid, decomposition point >250°.

Stage 8: The oxidation and subsequent detritylation of 6.8 g (0.0092 mole) of 7-[2-n-butoxyimino-2-(2-tritylaminothiazol-4-yl)-acetamino]-cephalosporanic acid to give the 1-S-oxide of 7-[2-(2-aminothiazol-4-yl)-2-n-butoxyimino-acetamino]-cephalosporanic acid was carried out analogously to Example 4, stage 8.

$C_{19}H_{23}N_5O_8S_2 \cdot \frac{1}{2}H_2O$ (522.5). Calculated: C, 43.7; H, 4.6; N, 13.4; S, 12.3. Found: C, 43.6; H, 4.5; N, 13.3; S, 12.4.

NMR (ppm, 60 MHz, $(CD_3)_2SO$): 0.7–1.8 (7H, m, —CH$_2$—CH$_2$—CH$_3$), 2.07 (3H, s, CH$_3$CO), 3.9 (2H, q, 2—CH$_2$), 4.1 (2H, t, —O—$\underline{CH_2}$—CH$_2$—), 4.90 (2H, q, 3—C—CH$_2$—O—), 5.0 (1H, d, 6—H), 5.93 (1H, q, 7—H), 6.80 (1H, s, aromatic H), 7.2 (2H, s, —NH$_2$) and 8.67 (1H, d, CONH—).

EXAMPLE 6

Tert.-butyl 7-(2-hydroxybenzylideneamino)-cephalosporanate 3.3 g (0.01 mole) of tert.-butyl 7-aminocephalosporanate are dissolved in 10.4 ccs (0.1 mole) of salicylaldehyde at room temperature, the solution is left to stand for one hour, 100 ccs of petroleum ether are added and the condensation product is filtered of and rinsed with petroleum ether. After recrystallization from methylene chloride/cyclohexane, 3.6 g of the title compound of melting point 156°–167° are obtained. The excess salicylaldehyde can be recovered by distilling the mother liquor.

$C_{21}H_{24}N_2O_6S$ (432.5). Calculated: C, 58.3; H, 5.6; N, 6.5; S, 7.4. Found: C, 58.1; H, 5.6; N, 6.3; S, 7.6.

EXAMPLE 7

The 1-R-oxide of tert.-butyl 7-(2-hydroxybenzylideneamino)cephalosporanate

A solution of 12.6 g (0.06 mole) of 3-chloroperoxybenzoic acid (82% pure) in 10 ccs of tetrahydrofuran is added dropwise to 21.6 g (0.05 mole) of tert.-butyl 7-(2-hydroxybenzylideneamino)-cephalosporanate, dissolved in 100 ccs of tetrahydrofuran, at 10°, while stirring. After stirring at the same temperature for one hour, 500 ccs of water are added and the mixture is adjusted to pH 8 with bicarbonate solution and stirred further until the initially oily precipitate has solidified. The precipitate is filtered off, rinsed successively with bicarbonate, water and ether and dried.

17.8 of the title compound of decomposition point 153°–155° C. are obtained.

$C_{21}H_{24}N_2O_7S$ (448.5) Calculated: C, 56.2; H, 5.4; N, 6.3; S, 7.2. Found: C, 56.3; H, 5.4; N, 6.2; S, 7.2.

$R_f$ value: 0.4 (Merck 60 thin layer chromatography silica gel, ethyl acetate).

Peroxyacetic acid, peroxybenzoic acid and monoperoxyphthalic acid, which can also be produced in situ, and hydrogen peroxide are similarly suitable as oxidizing agents.

EXAMPLE 8

The 1-R-oxide of 7-aminocephalosporanic acid 12 g (0.035 mole) of the 1-R-oxide of tert.-butyl 7-aminocephalosporanate (Example 9), dissolved in 120 ccs of trifluoroacetic acid, are stirred at room temperature for one and a half hours. The red-brown oil which remains after stripping off the trifluoroacetic acid is dissolved in 200 ccs of water, the solution is treated twice with active charcoal, and solid sodium bicarbonate is added to the yellowish filtrate until the pH value is 2.2. The title compound which has crystallized out is filtered off, washed with water and dried in vacuo.

6.7 g of decomposition point 250° are obtained.

$C_{10}H_{12}N_2O_6S$ (288.3). Calculated: C, 41.4; H, 4.2; N, 9.7; O, 33.3; S, 11.1. Found: C, 40.9; H, 4.2; N, 9.5; O, 33.1; S, 11.4.

NMR (ppm, 60 MHz, $D_2O + NaHCO_3$): 2.13 (3H, s, $CH_3$—O—), 4.0 (2H, q, 3—C—$CH_2$—O—), 4.86 (1H, d, 6—H) and 5.03 (1H, d, 7—H).

EXAMPLE 9

The 1-R-oxide of tert.-butyl 7-aminocephalosporanate 35.9 g (0.08 mole) of the 1R-oxide of tert.-butyl 7-(2-hydroxybenzylideneamino)-cephalosporanate are suspended in 480 ccs of methanol, 17.6 g (0.1 mole) of Girard T reagent are introduced and the mixture is warmed briefly to 35°–50° C. until a clear solution forms. After stirring at room temperature for about half an hour, the solution is concentrated and the residue is suspended and stirred in 500 ccs of water. The title compound is filtered off and washed successively with water, isopropanol and ether.

23 g of decomposition point 170° are obtained.

$C_{14}H_{20}N_2O_6S$ (344.4). Calculated: C, 48.8; H, 5.9; N, 8.1; S, 9.3. Found: C, 48.6; H, 6.0; N, 8.0; S, 9.3.

EXAMPLE 10

The 1-R-oxide of tert.-butyl 7-[2-methoxyimino-2-(2-tritylaminothiazol-4-yl)-acetamino]-cephalosporanate 44.3 g (0.1 mole) of 2-methoxyimino-2-(2-tritylaminothiazol-4-yl)-acetic acid in 150 ccs of methylene chloride are added dropwise to a solution of 12.3 g (0.058 mole) of dicyclohexylcarbodiimide (97% pure) in 87 ccs of methylene chloride at 5°, while stirring, the mixture is stirred for a further 40 minutes and the temperature is allowed to rise to 20° in the course of 30 minutes. Dicyclohexylurea which has precipitated is filtered off, and a solution of 17.2 g (0.05 mole) of the 1-R-oxide of tert.-butyl 7-aminocephalosporanate in 150 ccs of methylene chloride is added dropwise to the filtrate at −10°, while stirring. The mixture is further stirred at room temperature for 90 minutes and concentrated, the residue is dissolved in 500 ccs of ethyl acetate, if appropriate a little tetrahydrofuran being added, and 8 ccs (0.075 mole) of diethylamine are added. After cooling the mixture with ice for one hour, 27 g of the diethylamine salt of the starting acid are filtered off and rinsed with ethyl acetate. After clarification with a little charcoal, the filtrate is shaken with 200 ccs of 0.5 N hydrochloric acid and the organic phase is separated, washed with water until neutral, dried over sodium sulfate and concentrated until a thick crystal sludge forms. This is stirred with ether and the solid is filtered off, washed with ether and dried in vacuo. 25.2 g of the title compound of decomposition point 175° are obtained.

$C_{39}H_{39}N_5O_8S_2$ (769.9). Calculated: C, 60.8; H, 5.1; N, 9.1; S, 8.3. Found: C, 60.5; H, 5.0; N, 9.0; S, 8.4.

$R_f$ value: 0.48/thin layer chromatography, Merck 60 silica gel, ethyl acetate.

NMR (ppm, 60 MHz, $(CD_3)_2SO$): 1.5 (9H, s, —$C(CH_3)_3$), 2.07 (3H, s, $CH_3CO$), 3.83 (3H, s, =N—$OCH_3$), 3.93 (2H, q, 2—$CH_2$), 4.73 (2H, q, 3—C—$CH_2$—O), 4.97 (1H, d, 6—H), 5.73 (1H, q, 7—H), 6.87 (1H, s, aromatic H), 7.33 (15H, broad s, trityl), 8.8 (1H, s, NH) and 9.7 (1H, d, CONH—).

EXAMPLE 11

The 1-R-oxide of 7-[2-(2-aminothiazol-4-yl)-2-methoxyimino acetamino]-cephalosporanic acid 3.1 g (0.004 mole) of the 1-R-oxide of tert.-butyl 7-[2-methoxyimino-2-(2-tritylaminothiazol-4-yl)-acetamino]cephalosporanate are introduced in portions into 30 ccs of trifluoroacetic acid at 0°, while stirring, the mixture is stirred for 2 hours, 60 ccs of water are added and the triphenylcarbinol is filtered off. The filtrate is concentrated in vacuo and the residue is triturated with ether. The crude title compound can be purified by column chromatography [Merck $SiO_2$ (particle size 0.06–0.2 mm), solvent: ethyl acetate/isopropanol/water 4:3:2] and is converted into the sodium salt by dissolving in the equivalent amount of bicarbonate or sodium hydroxide solution and freeze-drying. Decomposition point >300°. $R_f$ value (free acid): 0.41 (thin layer chromatography, Merck 60 silica gel, ethyl acetate/isopropanol/water 4:3:2).

NMR (ppm, 60 MHz, $(CD_3)_2SO$): 2.0 (3H, s, $CH_3CO$), 3.37 (2H, q, 2—$CH_2$), 3.87 (3H, s, O—$CH_3$), 4.80(H, d, 6—H), 4.83 (2H, q, 3—C—$CH_2$—O), 5.63 (H, q, 7—H), 6.93 (H, s, aromatic H), 7.17 (2H, s, $NH_2$) and 9.73 (H, d, CONH—).

EXAMPLE 12

The 1-S-oxide of 7-[2-(2-aminothiazol-4-yl)-2-methoxyimino-acetamino]-3-(1-methyltetrazol-5-yl-thiomethyl)-3-cephem-4-carboxylic acid Stage 1: 7.2 g (0.015 mole) of the sodium salt of 7-[2-(2-aminothiazol-4-yl)-2-methoxyimino-acetamino]-cephalosporanic acid and 8.1 g (0.045 mole) of the sodium salt of 5-mercapto-1-methyltetrazole dihydrate are dissolved in 175 ccs of water, the pH value of the solution is adjusted to 7 with sodium bicarbonate solution and the solution is heated to 50° for 18 hours, under nitrogen. The reaction mixture is adjusted to pH 5 with 1N HCl and filtered with charcoal and the filtrate is acidified to pH 2. The precipitate is filtered off, washed with water and dried over pentoxide.

3.4 g of 7-[2-(2-aminothiazol-4-yl)-2-methoxyiminoacetamino]-3-(1-methyltetrazol-5-yl-thiomethyl)-3-cephem-4-carboxylic acid are obtained. A further preparation method for this compound consists in reacting 7-[2-(2-tritylaminothiazol-4-yl)-2-methoxyimino-acetamino]-cephalosporanic acid with 5-mercapto-1-methyl-tetrazole at pH 7±1 under analogous conditions and then splitting off the trityl protective group of the reaction product in 80% strength formic acid analogously to Example 3, stage 2, or with trifluoroacetic acid (0.5 to 1 hour at 0°–10°).

Stage 2: 1.9 g (0.037 mole) of 7-[2-(2-aminothiazol-4-yl)-2-methoxyimino-acetamino]-3-(1-methyltetrazol-5-yl-thiomethyl)-3-cephem-4-carboxylic acid are dissolved in a mixture of 40 ccs of tetrahydrofuran and 25 ccs of formic acid, and 0.7 g (0.004 mole) of 3-chloroperoxybenzoic acid in 3 ccs of tetrahydrofuran is added dropwise at room temperature, while stirring. After stirring for half an hour, the small amount of by-product which has precipitated is filtered off and the reaction product is precipitated with ether.

1.4 g of the title compound of decomposition point >>250° are obtained. The title compound is also obtained by coupling the 1-S-oxide of 7-amino-3-(1- methyltetrazol-5-yl-thiomethyl)-3-cephem-4-carboxylic acid and 2-methoxyimino-2-(2-tritylaminothiazol-4-yl)-acetic acid analogously to Example 4, stage 6, and then splitting off the trityl protective group with 80% strength formic acid or trifluoroacetic acid in the manner described above.

NMR (ppm, 60 MHz, $(CD_3)_2SO$): 3.87 and 3.93 (6H, two s, $-OCH_3$ and $N-CH_3$), 4.35 (2H, q, 3$-CH_2-S-$), 4.93 (1H, d, 6$-H$), 5.83 (1H, q, 7$-H$), 6.80 (1H, s, aromatic H), 7.15 (1H, s, $NH_2$) and 8.80 (1H, d, $CONH-$).

EXAMPLE 13

The 1,1-dioxide of 7-[2-(2-aminothiazol-4-yl)-2-methoxyimino acetamino]-cephalosporanic acid Route 1: A solution of 3.5 g (0.02 mole) of 3-chloroperoxybenzoic acid in 10 ccs of tetrahydrofuran is added dropwise to 4.6 g (0.01 mole) of 7-[2-(2-aminothiazol-4-yl)-2-methoxyiminoacetamino]-cephalosporanic acid in 30 ccs of formic acid and 10 ccs of methanol at 20°, while stirring. After 20 hours, the mixture is poured into 750 ccs of ether and the precipitate is filtered off, washed with ether and dried. For further purification, all the crude product is stirred with 100 ccs of water for about 20 minutes, whereupon the dioxide dissolves. The undissolved impurities are filtered off and the filtrate is freeze-dried. 2.2 g of the title compound are obtained.

Route 2: A solution of 0.76 g (0.0044 mole) of 3-chloroperoxybenzoic acid in 3 ccs of tetrahydrofuran is added dropwise to 1.4 g (0.002 mole) of 7-[2-methoxyimino-2-(2-tritylaminothiazol-4-yl)-acetamino]-cephalosporanic acid in 5 ccs of tetrahydrofuran at room temperature, while stirring, and, after standing for 1.5 hours, the mixture is poured into 200 ccs of ether. The precipitate is filtered off, washed with ether and dried over phosphorus pentoxide. This product (0.9 g) is dissolved in 10 ccs of 80% strength aqueous formic acid, the solution is stirred at room temperature for 2 hours, 5 ccs of water are added and the triphenylcarbinol which has separated out is filtered off. The filtrate is diluted with 50 ccs of water and clarified with charcoal, the formic acid is removed by concentrating the mixture in vacuo, a further 50 ccs of water are added to the residue and the solid is filtered off and freeze-dried.

0.5 g of the title compound is obtained.

Route 3: 4.4 g (0.01 mole) of 2-methoxyimino-2-(2-tritylaminothiazol-4-yl)-acetic acid and 1.8 g (0.005 mole) of the 1,1-dioxide of tert.-butyl 7-aminocephalosporanate are subjected to a condensation reaction analogously to Example 10 to give the 1,1-dioxide of tert.-butyl 7-[2-methoxyimino-2-(2-tritylaminothiazol-4-yl)-acetamino]-cephalosporanate, and the trityl protective group and tert.-butyl protective group are split off with trifluoroacetic acid in the manner already described. $R_f$ value: 0.46 (thin layer chromatography, Merck 60 silica gel, ethyl acetate, isopropanol, water 4:3:2).

NMR (ppm, 60 MHz, $(CD_3)_2SO$): 2.03 (3H, s, $COCH_3$), 3.83 (3H, s, $-OCH_3$), 3.5–5.3 (4H, m, 2$-CH_2$, 3$-CH_2-O-$), 5.43 (1H, d, 6$-H$), 6.03 (1H, q, 7$-H$), 6.77 (1H, s, aromatic H), 7.13 (2H, broad s, $NH_2$) and 9.6 (H, d, $CONH-$).

EXAMPLE 14

The 1,1-dioxide of tert.-butyl 7-amino-cephalosporanate

Stage 1: A solution of 4.2 g (0.024 mole) of 3-chloroperoxybenzoic acid in 15 ccs of tetrahydrofuran is added dropwise to 4.32 g (0.01 mole) of tert.-butyl 7-(2-hydroxy-benzylideneamino)-cephalosporanate (Example 6) in 20 ccs of tetrahydrofuran at room temperature, while stirring, and the mixture is further stirred for 3.5 hours and cooled with ice. The crystals which have separated out (0.35 g) are filtered off. They consist of a mixture of the sulfoxide and sulfone of the starting ester. On adding 200 ccs of ether to the filtrate and cooling further, 0.86 g of the 1,1-dioxide of tert.-butyl 7-(2-hydroxy-benzylideneamino)-cephalosporanate crystallizes out.

$C_{21}H_{24}N_2O_8S$ (464.5). Calculated: C, 54.3; H, 5.2; N, 6.0; S, 6.9. Found: C, 54.4; H, 5.3; N, 5.9; S, 7.1. $R_f$ value: 0.63 (thin layer chromatography, Merck 60 silica gel, ethyl acetate).

Stage 2: The splitting off of the hydroxybenzylidene protective group is carried out analogously to Example 9.

EXAMPLE 15

The 1-S-oxide of ethoxy-ethoxycarbonyl-methyl 7-[2-(2-aminothiazol-4-yl)-2-methoxyimino-acetamino]-cephalosporanate 0.71 g (0.0043 mole) of ethyl 2-ethoxy-2-chloroacetate (boiling point$_{13}$ 82°–83° C.) is added dropwise to a solution of 2 g (0.0043 mole) of the 1-S-oxide of 7-[2-(2-aminothiazol-4-yl)-2-methoxyimino-acetamino]-cephalosporanic acid (Example 2) and 0.6 cc (0.0044 mole) of triethylamine in 20 ccs of dimethylformamide at room temperature, while stirring, the mixture is further stirred for 30 minutes and the solvent is stripped off in vacuo. The residue is dissolved in chloroform and the solution is washed with water and sodium bicarbonate and, after drying with sodium sulfate, is concentrated to 20 ccs. It is poured into 250 ccs of ether, the precipitate is filtered off and, after drying over phosphorus pentoxide, 1.8 g of the title compound, which decomposes above 130° C., are obtained.

$C_{22}H_{27}N_5O_{11}S_2 \times \frac{1}{2} H_2O$ (610.6). Calculated: C, 43.3; H, 4.6; N, 11.5; S, 10.5. Found: C, 43.2; H, 4.6; N, 11.4; S, 10.5.

$R_f$ value: 0.75 (Merck thin layer chromatography silica gel, ethyl acetate/i-propanol/water 4:3:2).

EXAMPLE 16

The 1-S-oxide of methoxy-methoxycarbonyl-methyl 7-[2-(2-aminothiazol-4-yl)-2-methoxyimino-acetamino]-cephalosporanate The title compound, decomposition point >150° C., was obtained analogously to Example 15 by reacting the 1-S-oxide of 7-[2-(2-aminothiazol-4-yl)-2-methoxyimino-acetamino]-cephalosporanic acid (Example 2) with methyl 2-chloro-2-methoxyacetate (boiling point$_{22}$ 75°–77° C.).

$C_{20}H_{23}N_5O_{11}S_2 \times \frac{1}{2} H_2O$ (582.5). Calculated: C, 41.2; H, 4.2; N, 12.0; S, 11.0. Found: C, 41.0; H, 4.2; N, 11.8; S, 11.2.

$R_f$ value: 0.7 (Merck silica gel, ethyl acetate/i-propanol/water 4:3:2).

EXAMPLE 17

The 1-S-oxide of propoxy-propoxycarbonyl-methyl 7-[2-(2-aminothiazol-4-yl)-2-methoxyimino-acetamino]-cephalosporanate The title compound, which slowly decomposes from 140° C., was obtained analogously to Example 15 by reacting the 1-S-oxide of 7-[2-(2-aminothiazol-4-yl)-2-methoxyimino-acetamino]-cephalosporanic acid (Example 2) with propyl 2-chloro-2-propoxyacetate (boiling point₂₃ 115°–117° C.).

$C_{24}H_{31}N_5O_{11}S_2$ (629.6). Calculated: C, 45.8; H, 5.0; N, 11.1; S, 10.2. Found: C, 45.5; H, 5.0; N, 11.0; S, 10.3.

EXAMPLE 18

The 1-S-oxide of n-butoxy-n-butoxycarbonyl-methyl 7-[2-(2-aminothiazol-4-yl)-2-methoxyimino-acetamino]-cephalosporanate The title compound, which decomposes from 145° C., was obtained analogously to Example 15 by reacting the 1-S-oxide of 7-[2-(2-aminothiazol-4-yl)-2-methoxyimino-acetamino]-cephalosporanic acid (Example 2) with n-butyl 2-n-butoxy-2-n-butoxyacetate (boiling point₂₄ 145°–147° C.).

$C_{26}H_{35}N_5O_{11}S_2$ (657.7). Calculated: C, 47.5; H, 5.4; N, 10.7; S, 9.8. Found: C, 47.2; H, 5.4; N, 10.5; S, 9.8.

EXAMPLE 19

The 1-S-oxide of methoxy-methoxycarbonyl-methyl 7-[2-ethoxyimino-2-(2-aminothiazol-4-yl)-acetamino]-cephalosporanate The title compound, which decomposes from 130° C., was obtained analogously to Example 15 by reacting the 1-S-oxide of 7-[2-ethoxyimino-2-(2-aminothiazol-4-yl)-acetamino]-cephalosporanic acid (Example 3) with methyl 2-chloro-2-methoxyacetate (boiling point₂₂ 75°–77° C.).

$C_{21}H_{25}N_5O_{11}S_2$ (587.8). Calculated: C, 42.9; H, 4.3; N, 11.9; S, 10.9. Found: C, 42.5; H, 4.3; N, 11.7; S, 10.6.

EXAMPLE 20

The 1,1-dioxide of tert.-butyl 7-(tert.-butoxycarbonylamino)cephalosporanate

Stage 1: 4.5 g (0.021 mole) of N-(tert.-butoxycarbonyloxy)succinimide are added to 6.6 g (0.02 mole) of tert.-butyl 7-aminocephalosporanate, dissolved in 25 ccs of pyridine. The mixture is stirred at room temperature for 7 hours, the pyridine is stripped off in vacuo and the residue is triturated in water with the addition of 2 N HCl and filtered off. 8.4 g of crude product are obtained which, after recrystallization from methanol/H₂O with the addition of active charcoal, gives 6.5 g of tert.-butyl 7-(tert.-butoxycarbonylamino)-cephalosporanate of melting point 145°–146°.

Stage 2: A solution of 6.7 g (0.0304 mole) of 3-chloroperoxybenzoic acid (78.3% pure) in 10 ccs of tetrahydrofuran is added to 6.5 g (0.0152 mole) of tert.-butyl 7-(tert.-butoxycarbonylamino)-cephalosporanate, dissolved in 30 ccs of tetrahydrofuran, at 20°, while cooling, and the mixture is left to stand at room temperature for 16 hours. The oil which has been precipitated by adding 300 ml of water solidifies on treatment with sodium bicarbonate and, after recrystallization from acetone/water, gives 6 g of the title compound of decomposition point 178°–179°.

$C_{19}H_{28}N_2O_9S$ (460.5). Calculated: C, 49.6; H, 6.1; N, 6.1; O, 31.3; S, 7.0. Found: C, 49.3; H, 5.8; N, 6.2; O, 31.3; S, 7.1.

NMR (ppm, 60 MHz, (CD₃)₂SO): 1.44 and 1.5 (18H, 2S, (CH₃)₃CO—), 2.03 (3H, S, CH₃—CO—), 4.23 (2H, d, 2—CH₂), 4.78 (2H, q, 3—C—CH₂—O—), 5.32 (1H, d, 6H), 5.76 (1H, q, 7H) and 7.11 (1H, d, —CONH—).

EXAMPLE 21

The 1,1-dioxide of 7-aminocephalosporanic acid 2.3 g (0.005 mole) of the 1,1-dioxide of tert.-butyl 7-(tert.-butoxycarbonylamino)-cephalosporanate (Example 20) are dissolved in 23 ccs of trifluoroacetic acid and the solution is left to stand at room temperature for 1.5 hours. The trifluoroacetic acid is stripped off in vacuo, 150 ml of water are added to the residue and the crystals which are obtained are filtered off and dried in vacuo. 1.3 g of the title compound of decomposition point 179°–180° are obtained.

$C_{10}H_{12}N_2O_7S$ (304.3). Calculated: C, 39.5; H, 4.0; N, 9.2; S, 10.5. Found: C, 39.7; H, 4.4; N, 8.9; S, 10.7.

NMR (ppm, 60 MHz, D₂O+NaHCO₃): 2.12 (3H, s, CH₃—CO—), 4.8 (2H, q, 3—C—CH₂—O—), 5.0 (1H, d, 6—H) and 5.16 (1H, d, 7—H).

EXAMPLE 22

The 1,1-dioxide of tert.-butyl 7-aminocephalosporanate 23 g (0.05 mole) of the 1,1-dioxide of tert.-butyl 7-(tert.-butoxycarbonylamino)-cephalosporanate (Example 20) are dissolved in 115 ccs of trifluoroacetic acid at 25° and, after 5 minutes, the reaction mixture is poured into 500 ccs of water. The filtered solution is adjusted to pH 8 with sodium bicarbonate. After filtering off and drying the crystals, 10.6 g of the title compound of decomposition point 173° are obtained.

2.4 g of the 1,1-dioxide of 7-aminocephalosporanic acid (Example 21) are obtained by acidifying the mother liquor (pH 2).

$C_{14}H_{20}N_2O_7S$ (360.4). Calculated: C, 46.7; H, 5.6; N, 7.8; O, 31.1; S, 8.9. Found: C, 46.4; H, 5.4; N, 7.5; O, 30.8; S, 9.2.

NMR (ppm, 60 MHz, (CD₃)₂SO): 1.48 (9H, s, (CH₃)₃CO—), 2.02 (3H, s, CH₃—CO—), 2.83 (2H, s, —NH₂), 4.15 (2H, q, 2—CH₂), 4.77 (2H, q, 3—C—CH₂—O—), 4.98 (1H, d, 6—H) and 5.18 (1H, d, 7—H).

EXAMPLE 23

The 1-S-oxide of 7-aminocephalosporanic acid

A solution of 4.6 g (0.021 mole) of 3-chloroperoxybenzoic acid (72.3% pure) is added dropwise to 5.5 g (0.02 mole) of 7-aminocephalosporanic acid, dissolved in 50 ccs of formic acid, at 20°. The mixture is subsequently stirred for 20 minutes, 40 ml of methanol are added, the mixture is poured into 500 ml of ether and the precipitate is filtered off and dried in vacuo. 4.9 g of the title compound of decomposition point 250° are obtained.

$C_{10}H_{12}N_2O_6S$ (288.3). Calculated: C, 41.7; H, 4.2; N, 9.7; O, 33.3; S, 11.1. Found: C, 41.6; H, 4.4; N, 9.8; O, 33.2; S, 10.9.

EXAMPLE 24

The S-1,1-dioxide of 7-[2-(2-aminothiazol-4-yl)-2-methoxyimino-acetamido]-3-(pyrid-2'-yl-thiomethyl)-3-cephem-4-carboxylic acid The title compound of decomposition point 210° was obtained analogously to Example 12 by reacting 7-[2-(2-aminothiazol-4-yl)-2-methoxyimino-acetamido]-cephalosporanic acid with the 1-oxide of 2-mercapto-pyridine and subsequently oxidizing the product with 3-chloroperoxybenzoic acid.

$C_{19}H_{18}N_6O_7S_3 \cdot 2H_2O$ (574.6). Calculated: C, 39.7; H, 3.9; N, 14.6. Found: C, 39.9; H, 3.7; N, 14.4.

EXAMPLE 25

The 1,1-dioxide of
7-[2-ethoxyimino-2-(2-aminothiazol-4-yl)-acetamido]-cephalosporanic acid 160 ml (0.32 mole) of 2 N sodium hydroxide solution is added dropwise to a suspension of 73 g (0.3 mole) of ethyl 2-ethoxyimino-2-(2-aminothiazol-4-yl)-acetate (prepared analogously to Example 4, stages 1 to 3) in 300 ccs of ethanol, the mixture is stirred at room temperature for 18 hours, 300 ccs of ether are then added dropwise and the sodium salt which has crystallized out is filtered off and washed with tetrahydrofuran and ether. The sodium salt is suspended in 220 ml of methanol, and the equivalent amount of concentrated hydrochloric acid is added. The product is filtered off, washed with ether and dried in vacuo, and 52.6 g of 2-ethoxyimino-2-(2-aminothiazol-4-yl)-acetic acid are obtained. 2-Ethoxyimino-2-(2-aminothiazol-4-yl)-acetic acid is reacted, in the form of the active ester (for example hydroxysuccinimido or pentachlorophenol) with the equivalent amount of the 1,1-dioxide of tert.-butyl 7-aminocephalosporanate (Example 22) in pyridine at room temperature to give the 1,1-dioxide of tert.-butyl 7-[2-ethoxyimino-2-(2-aminothiazol-4-yl)-acetamido]-cephalosporanate of decomposition point 180°.

NMR (ppm, 60 MHz, $(CD_3)_2SO$): 1.22 (3H, t, —O—CH$_2$—CH$_3$), 1.52 (9H, s, —O—C(CH$_3$)$_3$), 2.07 (3H, s, CH$_3$—CO—), 4.08 (2H, q, —O—CH$_2$—CH$_3$), 4.26 (2H, s, 2—CH$_2$), 4.78 (2H, q, 3—C—CH$_2$—O—), 5.43 (1H, d, 6—H), 6.06 (1H, q, 7—H), 6.75 (1H, s, aromatic, H), 7.18 (2H, s, —NH$_2$) and 9.48 (1H, d, —CONH—).

2.4 g (0.0043 mole) of the 1,1-dioxide of tert.-butyl 7-[2-ethoxyimino-2-(2-aminothiazol-4-yl)-acetamido]-cephalosporanate are dissolved in 12 ccs of trifluoroacetic acid and the solution is stirred at room temperature for 1 hour. After stripping off the trifluoroacetic acid in vacuo, grinding the oil residue with ether and filtering off and drying the crystals in vacuo, 2.4 g of the title compound in the form of the trifluoroacetate of decomposition point 138° are obtained.

$C_{19}H_{20}F_3N_5O_{11}S_2$ (615.5). Calculated: C, 37.1; H, 3.3; N, 11.4; S, 10.4. Found: C, 36.8; H, 3.4; N, 11.7; S, 10.4.

NMR (ppm, 60 MHz, $(CD_3)_2SO$): 1.22 (3H, t, —O—CH$_2$—CH$_3$), 2.03 (3H, s, CH$_3$—CO—), 4.11 (2H, q, —O—CH$_2$—CH$_3$), 4.25 (2H, s, 2—CH$_2$), 4.83 (2H, q, 3—C—CH$_2$—O—), 5.43 (1H, d, 6—H), 6.01 (1H, q, 7—H), 6.78 (1H, s, aromatic, H) and 9.50 (1H, d, —CONH—). R$_f$ value: 0.43 (thin layer chromatography on silica gel by ethyl acetate/isopropanol/water 4:3:2).

EXAMPLE 26

The 1,1-dioxide of
7-[2-(2-aminothiazol-4-yl)-2-n-butoxyimino acetamido]-cephalosporanic acid The title compound of decomposition point 120° was obtained analogously to Example 25.

The title compound contains 13.8% of trifluoroacetic acid; the elementary composition was calculated accordingly.

Calculated: C, 40.1; H, 3.9; N, 11.4; S, 10.4. Found: C, 39.9; H, 3.9; N, 11.2; S, 10.4.

NMR (ppm, 60 MHz, $(CD_3)_2SO$): 0.63–1.9 (7H, m, —CH$_2$—CH$_2$—CH$_3$), 2.03 (3H, s, CH$_3$—CO—), 4.08 (2H, t, —O—CH$_2$—CH$_2$—), 4.25 (2H, d, 2—CH$_2$), 4.85 (2H, q, 3—C—CH$_2$—O—), 5.43 (1H, d, 6—H), 6.03 (1H, q, 7—H), 6.80 (1H, s, aromatic, H) and 9.55 (1H, d, —CONH).

EXAMPLE 27

The 1,1-dioxide of
7-[2-allyloxyimino-2-(2-aminothiazol-4-yl)-acetamido]-cephalosporanic acid The title compound of decomposition point 130° was obtained analogously to Example 25. It contains 7.9% of trifluoroacetic acid; the elementary composition was calculated accordingly.

Calculated: C, 40.4; H, 3.5; N, 12.6; S, 11.5. Found: C, 39.4; H, 3.6; N, 12.4; S, 11.3.

NMR (ppm, 60 MHz, $(CD_3)_2SO$): 2.03 (3H, s, CH$_3$—CO—), 4.25 (2H, d, 2—CH$_2$), 4.4–6.4 (5H, m, —OCH$_2$.CH=CH$_2$), 4.85 (2H, q, 3—C—CH$_2$—O—), 5.43 (1H, d, 6—H), 6.01 (1H, q, 7—H), 6.78 (1H, s, aromatic, H) and 9.62 (1H, d, —CONH—).

EXAMPLE 28

The 1,1-dioxide of
7-[2-(2-aminothiazol-4-yl)-2-(2-bromoallyloxyimino)-acetamido]-cephalosporanic acid The title compound of decomposition point 115° was obtained anlogously to Example 25 from 2-(2-bromoallyloxyimino)-2-(2-aminothiazol-4-yl)-acetic acid and the 1,1-dioxide of tert.-butyl 7-aminocephalosporanate. It contains 6.2% of trifluoroacetic acid; the elementary composition was calculated accordingly.

Calculated: C, 35.5; H, 2.9; N, 11.1; Br, 12.7; S, 10.2. Found: C, 35.7; H, 3.2; N, 10.8; Br, 12.0; S, 10.2.

NMR (ppm, 60 MHz, $(CD_3)_2SO$): 2.03 (3H, s, CH$_3$—CO—), 4.25 (2H, d, 2—CH$_2$), 4.67 (2H, s, —O—CH$_2$—C—), 4.85 (2H, q, 3—C—CH$_2$—O—), 5.45 (1H, s, 6—H), 5.85 (2H, q, —C=CH$_2$), 6.01 (1H, q, 7—H), 6.81 (1H, s, aromatic, H) and 9.75 (1H, d, —NHCO—).

EXAMPLE 29

The 1-R-dioxide of
7-[2-ethoxyimino-2-(2-aminothiazol-4-yl)acetamido]-cephalosporanic acid 2.9 g (0.01 mole) of the 1-R-oxide of 7-aminocephalosporanic acid (Example 8) are suspended in 40 ccs of methylene chloride, 2.4 ccs (0.01 mole) of bis-trimethylsilyl-acetamide are added and the mixture is stirred at room temperature for 45 minutes. 0.01 mole of an active ester of 2-ethoxyimino-2-(2-aminothiazol-4-yl)-acetic acid is added to the clear solution and the mixture is stirred at room temperature for about 20 hours. It is filtered and the residue is triturated with water and ethanol. 1.6 g of the title compound of decomposition point 250° are obtained.

$C_{17}H_{19}N_5O_8S_2$ (485.5). Calculated: C, 42.1; H, 3.9; N, 14.4; O, 26.4; S, 13.2. Found: C, 42.2; H, 3.8; N, 14.6; O, 26.5; S, 13.4.

NMR (ppm, 60 MHz, $(CH_3)_2SO$): 1.22 (3H, t, —O—CH$_2$—CH$_3$), 2.05 (3H, s, CH$_3$—CO—), 3.93 (2H, q, 2—CH$_2$), 4.11 (2H, q, —O—CH$_2$—CH$_3$), 4.80 (2H, q, 3—C—CH$_2$—O—), 4.90 (1H, d, 6—H), 5.76 (1H, q, 7—H), 6.80 (1H, s, aromatic, H), 7.18 (2H, s, —NH$_2$) and 9.68 (1H, d, —CONH—).

EXAMPLE 30

The monoformate of the S-oxide of
7β-[2-(2-aminothiazol-4-yl)-2-syn-methoxyimino-acetamido]-3-[2-(β-carboxy-propionylamido)-1,3,4-thiadiazol-5-yl-thiomethyl]-ceph-3-em-4-carboxylic acid 792 mg (1.26 mmoles) of 7β-[2-(2-aminothiazol-4-yl)-2-syn-methoxyimino-acetamido]-3-[2-(β-carboxy-propionylamido)-1,3,4-thiadiazol-5-yl-thiomethyl]-ceph-3-em-4-carboxylic acid are dissolved in 10 ml of formic acid (98–100% strength) at room temperature. A solution of 278 mg (1.26 mmoles) of 78.3% pure m-chloroperbenzoic acid in 5 ml of tetrahydrofuran is added dropwise and the solution is stirred at room temperature for a further 30 minutes. The reaction solution is introduced into 150 ml of diethyl ether, while stirring, and the precipitate is filtered off and washed with ether. After drying in vacuo, 680 mg of the title compound are obtained.

$R_f$: 0.15 (silica gel, Messrs. Merck; ethyl acetate:methanol:glacial acetic acid=20:10:1)

IR (KBr): 1,774 cm$^{-1}$ (β-lactam band) NMR (d$_6$-DMSO, 60 MHz): δ=3.28 ppm (singlet, 3H, =N—OCH$_3$), δ=4.92 ppm (doublet, 1H, 6—CH—), δ=5.82 ppm (quartet, 1H, 7—CH—), δ=6.78 ppm (singlet, 1H, thiazole-H), δ=7.13 ppm (singlet, 2H, —NH$_2$), δ=8.83 ppm (doublet, 1H, —NH—CO—) and δ=8.13 ppm (singlet, 1H, formic acid).

EXAMPLE 31

The monoformate of the 1-S-oxide of
7β-[2-(2-aminothiazol-4-yl)-2-syn-methoxyimino-acetamido]-3-[2-(4-pyridyl)-1,3,4-oxadiazol-5-yl-thiomethyl]-ceph-3-em-4-carboxylic acid 1.15 g (20 mmoles) of 7β-[2-(2-aminothiazol-4-yl)-2-syn-methoxyimino-acetamido]-3-[2-(4-pyridyl)-1,3,4-oxadiazol-5-yl-thiomethyl]-ceph-3-em-4-carboxylic acid are dissolved in 15 ml of formic acid (98–100% strength) at room temperature. A solution of 442 mg (20 mmoles) of 78.3% pure m-chloroperbenzoic acid in 5 ml of tetrahydrofuran is added dropwise and the reaction solution is stirred at room temperature for 30 minutes. The reaction solution is introduced into 250 ml of ether, while stirring, and the precipitate is filtered off, washed with ether and dried in vacuo. 1.1 g of the title compound are obtained.

IR (KBr): 1,770 cm$^{-1}$ (β-lactam band)

NMR (d$_6$-DMSO, 60 MHz): δ=3.83 ppm (singlet, 3H, =N—OCH$_3$), δ=4.95 ppm (doublet, 1H, 6—CH—), δ=5.84 ppm (quartet, 1H, 7—CH—), δ=6.80 ppm (singlet, 1H, thiazole-H), δ=7.14 ppm (singlet, 2H, —NH$_2$), δ=7.89 ppm (multiplet, 2H, pyridyl—H—3,5), δ=8.80 ppm (multiplet, 3H, pyridyl—H—2,6 and —NH—CO—) and δ=8.12 ppm (singlet, 1H, formic acid).

EXAMPLE 32

The monoformate of the 1-S-oxide of
7β-[2-(2-aminothiazol-4-yl)-2-syn-methoxyimino-acetamido]-3-[2-(2-pyridyl)-1,3,4-oxadiazol-5-yl-thiomethyl]-ceph-3-em-4-carboxylic acid 550 mg (10 mmoles) of 7β-[2-(2-aminothiazol-4-yl)-2-syn-methoxyimino-acetamido]-3-[2-(2-pyridyl)-1,3,4-oxadiazol-5-yl-thiomethyl]-ceph-3-em-4-carboxylic acid are dissolved in 10 ml of formic acid (98–100% strength) at room temperature. A solution of 221 mg (10 mmoles) of 78.3% pure m-chloroperbenzoic acid in 5 ml of tetrahydrofuran is added dropwise and the reaction solution is stirred at room temperature for 30 minutes. The reaction solution is introduced into 200 ml of ether, while stirring, and the precipitate is filtered off, washed with ether and dried in vacuo. 480 mg of the title compound are obtained.

$R_f$: 0.16 (silica gel, Messrs. Merck; ethyl acetate:methanol:glacial acetic acid=20:10:1).

IR (KBr): 1,776 cm$^{-1}$ (β-lactam band).

NMR (d$_6$-DMSO); 60 MHz): δ=3.83 ppm (singlet, 3H, =N—OCH$_3$), δ=4.93 ppm (doublet, 1H, 6—CH—), δ=5.81 ppm (quartet, 1H, 7—CH—), δ=6.77 ppm (singlet, 1H, thiazole-H), δ=7.10 ppm (singlet, 2H, —NH$_2$), δ=7.56 ppm (multiplet, 1H, pyridyl—H—5), δ=8.00 ppm (multiplet, 2H, pyridyl—H—3,4), δ=8.70 ppm (multiplet, 1H, pyridyl—H—6), δ=8.82 ppm (doublet, 1H, —NH—CO—) and δ=8.06 ppm (singlet, 1H, formic acid).

EXAMPLE 33

The monoformate of the 1-S-oxide of
7β-[2-(2-aminothiazol-4-yl)-2-syn-methoxyimino-acetamido]-3-(1-ethyl-2-trifluoromethyl-1,3,4-triazol-5-yl-thiomethyl)-ceph-3-em-4-carboxylic acid 593 mg (10 mmoles) of 7β-[2-(2-aminothiazol-4-yl)-2-syn-methoxyimino-acetamido]-3-(1-ethyl-2-trifluoromethyl-1,3,4-triazol-5-yl-thiomethyl)-ceph-3-em-4-carboxylic acid are dissolved in 10 ml of formic acid (98–100% strength) at room temperature. A solution of 232 mg (10 mmoles) of 74% pure m-chloroperbenzoic acid in 5 ml of tetrahydrofuran is added dropwise and the solution is stirred at room temperature for a further 30 minutes. The reaction solution is introduced into 150 ml of ether, while stirring, and the precipitate is filtered off and washed with ether. 520 mg of the title compound are obtained.

$R_f$: 0.47 (silica gel, Messrs. Merck; acetone:glacial acetic acid=10:1) and 0.43 (silica gel, Messrs. Merck; ethyl acetate:methanol:glacial acetic acid=20:10:1)

IR (KBr): 1,774 cm$^{-1}$ (β-lactam band)

NMR (d$_6$-DMSO, 60 MHz): δ=1.28 ppm (triplet, 3H, N—C—CH$_3$), δ=3.81 ppm (singlet, 3H, =N—OCH$_3$), δ=4.18 ppm (quartet, 2H, —N—CH$_2$—C), δ=4.91 ppm (doublet, 1H, 6—CH—), δ=5.83 ppm (quartet, 1H, 7—CH—), δ=6.79 ppm (singlet, 1H, triazole—H), δ=7.16 ppm (singlet, 2H, —NH$_2$), δ=8.76 ppm (doublet, 1H, —NH—CO—) and δ=8.10 ppm (singlet, 1H, H—AM formic acid).

EXAMPLE 34

The monoformate of the 1-S-oxide of
7β-[2-(2-aminothiazol-4-yl)-2-syn-methoxyimino-acetamido]-3-(4,6-diamino-pyrimid-2-yl-thiomethyl)-ceph-3-em-4-carboxylic acid 1.07 g (2 mmoles) of 7β-[2-(2-aminothiazol-4-yl)-2-syn-methoxyimino-acetamido]-3-(4,6-diamino-pyrimid-2-yl-thiomethyl)-ceph-3-em-4-carboxylic acid are dissolved in 15 ml of formic acid (98–100% strength) at room temperature. A solution of 390 mg of 87% pure m-chloroperbenzoic acid in 5 ml of tetrahydrofuran is added dropwise and the mixture is stirred at room temperature for a further 30 minutes. The reaction solution is introduced into 150 ml of diethyl ether, while stirring, and the precipitate is filtered off and washed with a large amount of ether. After drying immediately in vacuo, 910 mg of the title compound are obtained.

R_f cannot be determined exactly—substance scarcely migrates in protic solvents

IR (KBr): 1,770 cm$^{-1}$ ($\beta$-lactam band)

NMR (d$_6$-DMSO, 60 MHz): $\delta=3.83$ ppm (singlet, 1H, =N—OCH$_3$), $\delta=4.89$ ppm (doublet, 1H, 6—CH—), $\delta=5.13$ ppm (singlet, 1H, pyrimidyl—H), $\delta=5.56$ ppm (quartet, 1H, 7—CH—), $\delta=6.11$ ppm (singlet, 2H, pyrimidyl—NH$_2$), $\delta=6.79$ ppm (singlet, 3H, thiazole-H and pyrimidyl—NH$_2$), $\delta=7.13$ ppm (singlet, 2H, thiazole—NH$_2$), $\delta=8.65$ ppm (doublet, 1H, —NH—CO) and $\delta=8.11$ ppm (singlet, 1H, formic acid).

EXAMPLE 35

The monoformate of the 1-S-oxide of 7$\beta$-[2-(2-aminothiazol-4-yl)-2-syn-methoxyimino-acetamido]-3-(1-methyl-2-trifluoromethyl-1,3,4-triazol-5-yl-thiomethyl)-ceph-3-em-4-carboxylic acid 700 mg (1.21 mmoles) of 7$\beta$-[2-(2-aminothiazol-4-yl)-2-syn-methoxyimino-acetamido]-3-(1-methyl-2-trifluoromethyl-1,3,4-triazol-5-yl-thiomethyl)-ceph-3-em-4-carboxylic acid are dissolved in 10 ml of formic acid (98-100% strength) at room temperature. 232 mg of 87% pure m-chloroperbenzoic acid in 5 ml of tetrahydrofuran are added dropwise, while stirring, and the mixture is stirred at room temperature for a further half an hour. It is introduced into 150 ml of ether, while stirring, and the precipitate is filtered off and washed with ether. After drying immediately, 540 mg of the title compound are obtained.

IR (KBr): 1,781 cm$^{-1}$ ($\beta$-lactam band)

NMR (d$_6$-DMSO, 60 MHz): $\delta=3.66$ ppm (singlet, 3H, —N—CH$_3$), $\delta=3.86$ ppm (singlet, 3H, =N—OCH$_3$), $\delta=4.94$ ppm (doublet, 1H, 6—CH—), $\delta=5.83$ ppm (quartet, 1H, 7—CH—), $\delta=6.79$ ppm (singlet, 1H, thiazole-H), $\delta=7.13$ ppm (singlet, 2H, —NH$_2$), $\delta=8.78$ ppm (doublet, 1H, —NH—CO—), and $\delta=8.11$ ppm (singlet, 1H, formic acid).

EXAMPLE 36

The monoformate of the 1-S-oxide of 7$\beta$-[2-(2-amino-thiazol-4-yl)-2-syn-methoxyimino-acetamido]-3-(1-ethyl-1,3,4-triazol-5-yl-thiomethyl)-ceph-3-em-4-carboxylic acid 1.5 g (3 mmoles) of 7$\beta$-[2-(2-aminothiazol-4-yl)-2-syn-methoxyimino-acetamido]-3-(1-ethyl-1,3,4-triazol-5-yl-thiomethyl)-ceph-3-em-4-carboxylic acid are dissolved in 25 ml of 98% strength formic acid at room temperature. 623 mg (3 mmoles+5% excess) of 87% pure m-chloroperbenzoic acid in 10 ml of tetrahydrofuran are added dropwise and the reaction solution is stirred at room temperature for 1.2 hours. The reaction mixture is introduced into 300 ml of ether, while stirring, and the precipitate is filtered off and washed with ether. After drying in vacuo, 1.5 g of the title compound are obtained.

IR (KBr): 1,770 cm$^{-1}$ ($\beta$-lactam band)

NMR (d$_6$-DMSO, 60 MHz): $\delta=4.25$ ppm (triplet, 3H, —N—O—CH$_3$), $\delta=3.74$ ppm (singlet, =N—OCH$_3$), $\delta=4.00$ ppm (multiplet, 2—CH$_2$—+—N—CH$_2$—C), $\delta=4.94$ ppm (doublet, 1H, 6—CH—), $\delta=5.75$ ppm (quartet, 1H, 7—CH—), $\delta=6.72$ ppm (singlet, 1H, thiazole—H), $\delta=7.14$ ppm (singlet, broad, —NH$_2$), $\delta=8.55$ ppm (singlet, 1H, triazole-H), $\delta=8.85$ ppm (doublet, 1H, —CO—NH—) and $\delta=8.18$ ppm (singlet, 1H, formic acid).

EXAMPLE 37

The monoformate of the 1-S-oxide of 7$\beta$-[2-(2-amino-thiazol-4-yl)-2-syn-methoxyimino-acetamido]-3-[2-(3-thienyl)-1H-1,3,4-triazol-5-yl-thiomethyl]-ceph-3-em-4-carboxylic acid 549 mg (0.95 mmole) of 7$\beta$-[2-(2-aminothiazol-4-yl)-2-syn-methoxyimino-acetamido]-3-[2-(3-thienyl)-1H-1,3,4-triazol-5-yl-thiomethyl]-ceph-3-em-4-carboxylic acid are dissolved in 10 ml of 98% strength formic acid at room temperature. 190 mg (0.95 mmole+5% excess) of 87% pure m-chloroperbenzoic acid in 5 ml of tetrahydrofuran are added dropwise, while stirring, and the reaction solution is stirred at room temperature for a further 45 minutes. The reaction mixture is introduced into 250 ml of ether, while stirring, the precipitate is filtered off and the residue is washed with ether. After drying in vacuo at 37° C., 450 mg of the title compound are obtained.

R$_f$: 0.07 (acetone:chloroform:glacial acetic acid=50:50:7), 0.18 (methanol:ethyl acetate:glacial acetic acid=10:20:1) and 0.57 (acetone:glacial acetic acid=10:1)

IR (KBr): 1,778 cm$^{-1}$ ($\beta$-lactam band)

NMR (d$_6$-DMSO, 60 MHz): $\delta=3.84$ ppm (singlet, 3H, =N—OCH$_3$), $\delta=4.91$ ppm (doublet, 1H, 6—CH—), $\delta=5.79$ ppm (quartet, 1H, 7—CH—), $\delta=6.77$ ppm (singlet, 1H, thiazole-H), $\delta=7.13$ ppm (singlet, broad, 2H, —NH$_2$), $\delta=7.60$ ppm (multiplet, 2H, thienyl-H-4,5), $\delta=8.05$ ppm (singlet, 1H, thienyl-H-2), $\delta=8.87$ ppm (doublet, 1H, —CO—NH—) and $\delta=8.05$ ppm (singlet, 1H, formic acid).

EXAMPLE 38

The monoformate of the 1-S-oxide of 7$\beta$-[2-(2-aminothiazol-4-yl)-2-syn-methoxyimino-acetamido]-3-[2-(3-furyl)-1H-1,3,4-triazol-5-yl-thiomethyl]-ceph-3-em-4-carboxylic acid 266 mg (0.47 mmole) of 7$\beta$-[2-(2-aminothiazol-4-yl)-2-syn-methoxyimino-acetamido]-3-[2-(3-furyl)-1H-1,3,4-triazol-5-yl-thiomethyl]-ceph-3-em-4-carboxylic acid are dissolved in 10 ml of 98% strength formic acid at room temperature. 112 mg (0.47 mmole+5% excess) of 87% pure m-chloroperbenzoic acid in 5 ml of tetrahydrofuran are added dropwise and the mixture is stirred at room temperature for a further 30 minutes. The reaction solution is introduced into 100 ml of ether, while stirring, and the precipitate is filtered off and washed with ether. After drying in vacuo at 37° C., 140 mg of the title compound are obtained.

R$_f$: 0.25 (ethyl acetate:methanol:glacial acetic acid=20:10:1)

IR (KBr): 1,775 cm$^{-1}$ ($\beta$-lactam band)

NMR (d$_6$-DMSO, 60 MHz): $\delta=3.33$ ppm (AB spectrum, 2—CH$_2$), $\delta=3.84$ ppm (singlet, =N—OCH$_3$), $\delta=4.18$ ppm (AB spectrum, 3—CH$_2$—S—), $\delta=4.85$ ppm (doublet, 1H, 6—CH—), $\delta=5.75$ ppm (quartet, 1H, 7—CH—), $\delta=6.77$ ppm (multiplet, 2H, thiazole—H+furyl—H—4), $\delta=7.12$ ppm (multiplet, 3H, furyl—H—5+—NH$_2$), $\delta=7.70$ ppm (singlet, 1H, furyl—H—2), $\delta=8.78$ ppm (doublet, 1H, —CO—NH—) and $\delta=8.09$ ppm (singlet, 1H, formic acid).

EXAMPLE 39

The monoformate of the 1-S-oxide of
7β-[2-(2-aminothiazol-4-yl)-2-syn-methoxyimino-acetamido]-3-[2-(2-thienyl)-1H-1,3,4-triazol-5-yl-thiomethyl]-ceph-3-em-4-carboxylic acid 1.16 g (2 mmoles) of 7β-[2-(2-aminothiazol-4-yl)-2-syn-methoxyimino-acetamido]-3-[2-(3-thienyl)-1-H-1,3,4-triazol-5-yl-thiomethyl]-ceph-3-em-4-carboxylic acid are dissolved in 15 ml of 98% strength formic acid at room temperature. A solution of 405 mg (2 mmoles+5% excess) of 87% pure metachloroperbenzoic acid in 15 ml of tetrahydrofuran is added dropwise, while stirring, and the mixture is stirred at room temperature for a further 60 minutes. It is introduced into 200 ml of ether, while stirring, and the precipitate is filtered off, washed with ether and dried in vacuo at 37° C. over KOH. 1.1 g of the title compound are obtained.

$R_f$: 0.10 (acetone:chloroform:glacial acetic acid=50:50:1), 0.19 (ethyl acetate:methanol:glacial acetic acid=20:10:1) and 0.36 (acetone:glacial acetic acid=10:1)

IR (KBr): 1,776 cm$^{-1}$ (β-lactam band).

NMR (d$_6$-DMSO, 6. MHz): δ=3.83 ppm (singlet, =N—OCH$_3$), δ=4.07 ppm (AB spectrum, 3—CH$_2$—S—), δ=4.90 ppm (doublet, 1H, 6—CH—), δ=5.78 ppm (quartet, 1H, 7—CH—), δ=6.77 ppm (singlet, 1H, thiazole-H), δ=7.13 ppm (multiplet, 3H, —NH$_2$+-thienyl—H—4), δ=7.63 ppm (multiplet, 2H, thienyl-H-3,5), δ=8.76 ppm (doublet, 1H, —CO—NH—) and δ=8.00 ppm (singlet, 1H, formic acid).

EXAMPLE 40

The monoformate of the 1-S-oxide of
7β-[2-(2-aminothiazol-4-yl)-2-syn-methoxyimino-acetamido]-3-[1H-1,3,4-triazol-5-yl-thiomethyl]-ceph-3-em-4-carboxylic acid 1.0 g (2 mmoles) of 7β-[2-(2-aminothiazol-4-yl)-2-syn-methoxyimino-acetamido]-3-(1H-1,3,4-triazol-5-yl-thiomethyl)-ceph-3-em-4-carboxylic acid are dissolved in 15 ml of 98% strength formic acid at room temperature. 416 mg of m-chloroperbenzoic acid (87% pure) in 5 ml of tetrahydrofuran are added dropwise, while stirring, and the mixture is stirred at room temperature for a further 75 minutes. It is then introduced into 200 ml of ether, while stirring, and the precipitate is filtered off, washed with ether and dried in vacuo at 37° C. over KOH. 0.98 g of the title compound is obtained.

$R_f$: 0.11 (ethyl acetate:methanol:glacial acetic acid=20:10:1)

IR (KBr): 1,774 cm$^{-1}$ (β-lactam band)

NMR (d$_6$-DMSO, 60 MHz): δ=3.86 ppm (singlet, =N—OCH$_3$), δ=4.88 ppm (doublet, 1H, 6—CH—), δ=5.80 ppm (quartet, 1H, 7—CH—), δ=6.76 ppm (singlet, 1H, thiazole-H), δ=7.13 ppm (singlet, broad, 2H, —NH$_2$), δ=8.36 ppm (singlet, 1H, triazole-H), δ=8.72 ppm (doublet, 1H, —CO—NH—) and δ=8.09 ppm (singlet, 1H, formic acid).

EXAMPLE 41

The monoformate of the 1-S-oxide of
7β-[2-(2-aminothiazol-4-yl)-2-syn-methoxyimino-acetamido]-3-[1-methyl-1,3,4-triazol-5-yl-thiomethyl]-ceph-3-em-4-carboxylic acid 1.02 g (2 mmoles) of 7β-[2-(2-aminothiazol-4-yl)-2-syn-methoxyimino-acetamido]-3-(1-methyl-1,3,4-triazol-5-yl-thiomethyl)-ceph-3-em-4-carboxylic acid are dissolved in 15 ml of 98% strength formic acid at room temperature. A solution of 416 mg (2 mmoles+5% excess) of 87% pure m-chloroperbenzoic acid in 10 ml of tetrahydrofuran is added dropwise and the mixture is stirred at room temperature for a further hour. It is introduced into 300 ml of ether, while stirring, and the precipitate is filtered off, washed thoroughly with ether and dried in vacuo. 920 mg of the title compound are obtained.

$R_f$: 0.04 (acetone:glacial acetic acid=10:1)

IR (KBr): 1,777 cm$^{-1}$ (β-lactam band)

NMR (d$_6$-DMSO, 60 MHz): δ=3.53 ppm (singlet, —N—CH$_3$), δ=3.86 ppm (singlet, —N—OCH$_3$), δ=4.89 ppm (doublet, 1H, C—H—6), δ=5.79 ppm (quartet, 1H, 7—CH—), δ=6.78 ppm (singlet, 1H, thiazole-H), δ=7.14 ppm (singlet, broad, 2H, —NH$_2$), δ=8.50 ppm (singlet, 1H, triazole-H), δ=8.76 ppm (doublet, 1H, —NH—CO—) and δ=8.07 ppm (singlet, 1H, formic acid).

EXAMPLE 42

The monoformate of the 1-S-oxide of
7β-[2-(2-aminothiazol-4-yl)-2-syn-methoxyimino-acetamido]-3-[1,2-dimethyl-1,3,4-triazol-5-yl-thiomethyl]-ceph-3-em-4-carboxylic acid 523 mg (1 mmole) of 7β-[2-(2-aminothiazol-4-yl)-2-syn-methoxyimino-acetamido]-3-(1,2-dimethyl-1,3,4-triazol-5-yl-thiomethyl)-ceph-3-em-4-carboxylic acid are dissolved in 10 ml of 98% strength formic acid at room temperature. A solution of 213 mg (1 mmole+5% excess) of 87% pure m-chloroperbenzoic acid in 5 ml of tetrahydrofuran is added dropwise, while stirring, and the mixture is stirred at room temperature for a further hour. It is introduced into 150 ml of ether and the precipitate is filtered off, washed several times with ether and dried in vacuo. 470 mg of the title compound are obtained.

$R_f$: 0.06 (acetone:glacial acetic acid=10:1)

IR (KBr): 1,775 cm$^{-1}$ (β-lactam band)

NMR (d$_6$-DMSO, 60 MHz): δ=2.33 ppm (singlet, —CH$_3$), δ=3.44 ppm (singlet, —N—CH$_3$), δ=3.86 ppm (singlet, =N—OCH$_3$), δ=4.92 ppm (doublet, 1H, 6—CH—), δ=5.82 ppm (quartet, 1H, 7—CH—), δ=6.79 ppm (singlet, 1H, thiazole—H), δ=7.20 ppm (broad absorption, 2H, —NH$_2$), δ=8.79 ppm (doublet, 1H, —NH—CO—) and δ=8.09 ppm (singlet, 1H, formic acid).

EXAMPLE 43

The monoformate of the 1-S-oxide of
7β-[2-(2-aminothiazol-4-yl)-2-syn-methoxyimino-acetamido]-3-(purin-6-yl-thiomethyl)-ceph-3-em-4-carboxylic acid 550 mg (1 mmole) of 7β-[2-(2-aminothiazol-4-yl)-2-syn-methoxyimino-acetamido]-3-(purin-6-yl-thiomethyl)-ceph-3-em-4-carboxylic acid are dissolved in 10 ml of 98% strength formic acid at room temperature. A solution of 230 mg (1 mmole+5% excess) of 87% pure m-chloroperbenzoic acid in 5 ml of tetrahydrofuran is added dropwise and the mixture is stirred at room temperature for a further 70 minutes. It is introduced into 200 ml of ether, while stirring, and the precipitate is filtered off, washed several times with ether and dried in vacuo. 530 mg of the title compound are obtained.

IR (KBr): 1,770 cm$^{-1}$ (β-lactam band)

NMR (d$_6$-DMSO, 60 MHz): δ=3.85 ppm (singlet, =N—OCH$_3$), δ=4.11 ppm (AB spectrum, 3—CH- 2—S—), δ=4.90 ppm (doublet, 1H, 6—CH—), δ=5.78 ppm (quartet, 1H, 7—CH—), δ=6.77 ppm (singlet, 1H, thiazole-H), δ=7.15 ppm (singlet, broad, 2H, —NH$_2$), δ=8.43 ppm (singlet, purinyl-8-H), δ=8.66 ppm (singlet, 1H, purinyl-2-H), δ=8.77 ppm (doublet, 1H, —NH—CO—) and δ=8.14 ppm (singlet, 1H, formic acid).

EXAMPLE 44

The monoformate of the 1-S-oxide of 7β-[2-(2-aminothiazol-4-yl)-2-syn-methoxyimino-acetamido]-3-(2-phenyl-1H-1,3,4-triazol-5-yl-thiomethyl)-ceph-3-em-4-carboxylic acid 1.15 g (2 mmoles) of 7β-[2-(2-aminothiazol-4-yl)-2-syn-methoxyimino-acetamido]-3-(2-phenyl-1H-1,3,4-triazol-5-yl-thiomethyl)-ceph-3-em-4-carboxylic acid are dissolved in 20 ml of 98% strength formic acid at room temperature. A solution of 480 mg (2 mmoles+5% excess) of 87% pure m-chloroperbenzoic acid in 8 ml of tetrahydrofuran is added dropwise and the mixture is stirred at room temperature for a further 70 minutes. It is introduced into 300 ml of ether, while stirring, and the precipitate is filtered off, washed several times with ether and dried. 1.05 g of the title compound are obtained.

IR (KBr): 1,776 cm$^{-1}$ (β-lactam band)

NMR (d$_6$-DMSO, 60 MHz): δ=3.85 ppm (singlet, =N—OCH$_3$), δ=4.87 ppm (doublet, 1H, 6—CH—), δ=5.77 ppm (quartet, 1H, 7—CH—), δ=6.74 ppm (singlet, 1H, thiazole—H), δ=7.10 ppm (singlet, broad, 2H, —NH$_2$), δ=7.42 ppm (multiplet, 2H, phenyl—H—3,4,5), δ=7.91 ppm (multiplet, 2H, phenyl—H—2,6), δ=8.71 ppm (doublet, 1H, —CO—NH—) and δ=8.07 ppm (singlet, 1H, formic acid).

EXAMPLE 45

The hemiformate of the 1-S-oxide of 7β-[2-(2-aminothiazol-4-yl)-2-syn-methoxyimino-acetamido]-3-(pyrimid-4-yl-thiomethyl)-ceph-3-em-4-carboxylic acid 788 mg (1.55 mmoles) of 7β-[2-(2-aminothiazol-4-yl)-2-syn-methoxyimino-acetamido]-3-(pyrimid-4-yl-thiomethyl)-ceph-3-em-4-carboxylic acid are dissolved in 15 ml of 98% formic acid at room temperature. A solution of 327 mg (1.55 mmoles+5% excess) of 87% pure meta-chloroperbenzoic acid in 8 ml of tetrahydrofuran is added dropwise and the mixture is stirred at room temperature for a further hour. It is introduced into 250 ml of ether and the precipitate is filtered off, washed several times with ether and dried. 720 mg of the title compound are obtained.

IR (KBr): 1,781 cm$^{-1}$ (β-lactam band)

NMR (d$_6$-DMSO, 60 MHz): δ=3.84 ppm (singlet, =N—OCH$_3$), δ=4.76 ppm (AB spectrum, 3—CH$_2$—S—), δ=4.87 ppm (doublet, 6—CH—), δ=5.78 ppm (quartet, 1H, —7—CH—), δ=6.75 ppm (singlet, 1H, thiazole—H), δ=7.12 ppm (singlet, broad, 2H, —NH$_2$), δ=7.41 ppm (quartet, 1H, pyrimidyl—H—5), δ=8.38 ppm (doublet, 1H, pyrimidyl—H—6), δ=8.85 ppm (doublet, 1H, pyrimidyl—H—2), δ=8.73 ppm (doublet, 1H, —CO—NH—) and δ=8.07 ppm (singlet, ½H and ½ mole of formic acid).

EXAMPLE 46

The hemiformate of the 1-S-oxide of 7β-[2-(2-aminothiazol-4-yl)-2-syn-methoxyiminoacetamido]-3-(1-phenyl-1,3,4-triazol-5-yl-thiomethyl)-ceph-3-em-4-carboxylic acid 748 mg (1.3 mmoles) of 7β-[2-(2-aminothiazol-4-yl)-2-syn-methoxyimino-acetamido]-3-(1-phenyl-1,3,4-triazol-5-yl-thiomethyl)-ceph-3-em-4-carboxylic acid are dissolved in 15 ml of 98% strength formic acid. 273 mg (1.3 mmoles+5% excess) of 87% pure m-chloroperbenzoic acid in 8 ml of tetrahydrofuran are added dropwise and the mixture is stirred at room temperature for a further hour. The reaction solution is introduced into 250 ml of ether, while stirring, and the precipitate is filtered off, washed with ether and dried in vacuo. 600 mg of the title compound are obtained.

IR (KBr): 1,776 cm$^{-1}$ (β-lactam band)

NMR (d$_6$-DMSO, 60 MHz): δ=3.85 ppm (singlet, =N—OCH$_3$), δ=4.83 ppm (doublet, 1H, 6—CH—), δ=5.80 ppm (quartet, 1H, 7—CH—), δ=6.77 ppm (singlet, 1H, thiazole-H), δ=7.13 ppm (singlet, broad, 2H, —NH$_2$), δ=7.46 ppm (multiplet, 5H, phenyl-H), δ=8.73 ppm (doublet, 1H, —CO—NH—), δ=8.84 ppm (singlet, 1H, triazole-H), and δ=8.06 ppm (singlet, ½H and ½ mole of formic acid).

EXAMPLE 47

The monoformate of the 1-S-oxide of 7β-[2-(2-aminothiazol-4-yl)-2-syn-methoxyimino-acetamido]-3-(1-phenyl-tetrazol-5-yl-thiomethyl)-ceph-3-em-4-carboxylic acid 589 mg (1.03 mmoles) of 7β-[2-(2-aminothiazol-4-yl)-2-syn-methoxyimino-acetamido]-3-(1-phenyl-tetrazol-5-yl-thiomethyl) ceph-3-em-4-carboxylic acid are dissolved in 10 ml of 98% strength formic acid. 214.5 mg (1.03 mmoles+5% excess) of 87% pure m-chloroperbenzoic acid in 5 ml of tetrahydrofuran are added dropwise at room temperature and the mixture is stirred at room temperature for a further 45 minutes. It is introduced into 250 ml of ether, while stirring, and the precipitate is filtered off, washed with ether and dried in vacuo. 410 mg of the title compound are isolated.

IR (KBr): 1,776 cm$^{-1}$ (β-lactam band)

NMR (d$_6$-DMSO, 60 MHz): δ=3.86 ppm (singlet, =N—OCH$_3$), δ=4.49 ppm (AB spectrum, 3—CH$_2$—S—), δ=4.92 ppm (doublet, 6—CH—), δ=5.82 ppm (quartet, 1H, 7—CH—), δ=6.78 ppm (singlet, 1H, thiazole-H), δ=7.15 ppm (broad absorption, 2H, —NH$_2$), δ=7.66 ppm (multiplet, 5H, phenyl-H), δ=8.79 ppm (doublet, 1H, —CO—NH—) and δ=8.10 ppm (singlet, 1H, formic acid).

EXAMPLE 48

The monoformate of the 1-S-oxide of 7β-[2-(2-aminothiazol-4-yl)-2-syn-methoxyimino-acetamido]-3-(5-carboxymethyl-4-methylthiazol-2-yl-thiomethyl)-ceph-3-em-4-carboxylic acid 500 mg (0.855 mmole) of 7β-[2-(2-aminothiazol-4-yl)-2-syn-methoxyimino-acetamido]-3-(5-carboxymethyl-4-methyl-thiazol-2-yl-thiomethyl)-ceph-3-em-4-carboxylic acid are dissolved in 10 ml of 98% strength formic acid. 178 mg (0.855 mmole+5% excess) of m-chloroperbenzoic acid in 7 ml of tetrahydrofuran are added dropwise and the mixture is stirred at room temperature for a further 45 minutes. It is then introduced into 200 ml of ether, while stirring, and the precipitate is filtered off, washed with ether and dried. 340 mg of the title compound are obtained.

IR (KBr): 1,776 cm$^{-1}$ ($\beta$-lactam band).

NMR (d$_6$-DMSO, 60 MHz): $\delta$=2.21 ppm (singlet, —CH$_3$), $\delta$=3.59 ppm (singlet —CH$_2$—COOH), $\delta$=3.76 ppm (singlet, =N—OCH$_3$), $\delta$=4.89 ppm (doublet, 6—CH—), $\delta$=5.81 ppm (quartet, 1H, 7—CH—), $\delta$=6.78 ppm (singlet, 1H, thiazole-H), $\delta$=7.14 ppm (broad absorption, 2H, —NH$_2$), $\delta$=8.78 ppm (doublet, 1H, —CO—NH—), and $\delta$=8.09 ppm (singlet, 1H, formic acid).

We claim:

1. A cephem compound of the formula

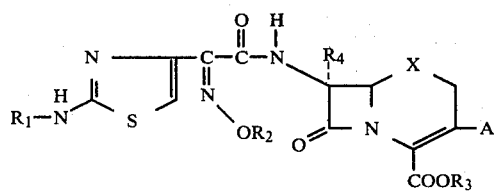

wherein the
OR$_2$ group is in the syn-position and
R$_1$ is hydrogen or an amino protective group known from peptide chemistry;
R$_2$ is hydrogen, alkyl having 1 to 4 carbon atoms, alkenyl having 2 to 6 carbon atoms, alkinyl having 3 to 5 carbon atoms, or such alkyl, alkenyl, or alkinyl substituted by
halogen
lower alkoxy carbonyl
phenoxy carbonyl
carboxyl
carbamyl
lower alkyl carbamyl
hydroxy lower alkyl carbamyl
pyrrolidinyl carbonyl
morpholinyl carbonyl
sulfamyl
sulfonyl
hydroxy
lower alkoxy
lower alkanoyloxy
lower alkyl sulfonyl
cycloalkyl having 3 to 6 carbon atoms
phenyl
nitrophenyl
halophenyl
lower alkoxyphenyl, or
lower alkylphenyl;
—COOR$_3$ is a carboxylic acid group, a physiologically acceptable carboxylic acid ester group, or a physiologically acceptable carboxylate salt group;
R$_4$ is hydrogen or lower alkoxy having 1 to 4 carbon atoms;
X is SO in the S-configuration or is SO$_2$; and
A is hydrogen, halogen, or —CH$_2$Y wherein
Y is a nucleophilic group which is aliphatic carbonyloxy, hydroxy, alkoxy having 1 to 8 carbon atoms, pyridino, quinolino, isoquinolino, such pyridino, quinolino, or isoquinolino substituted by
lower alkyl
lower alkoxy, or by
carbamyl, carbamyloxy, carbamylthio, such carbamyloxy or carbamylthio monosubstituted or disubstituted on the nitrogen atom by lower alkyl or by alkylene forming a 5- or 6-membered ring with the nitrogen atom, which ring may be interrupted by a further oxygen, sulfur, or nitrogen atom,
or Y is —SR$_5$ wherein
R$_5$ is aliphatic carbonyl having 1 to 4 carbon atoms, benzoyl, toluoyl, a 5-membered heteroaromatic ring wherein 1 ring member is sulfur or oxygen and 1 to 3 further ring members are nitrogen and the remaining ring members are carbon or wherein 2 to 4 ring members are nitrogen and the remaining ring members are carbon, such a 5-membered heteroaromatic ring fused to a benzene ring, or such a 5-membered heteroaromatic ring or 5-membered heteroaromatic ring fused to a benzene ring wherein said 5-membered heteroaromatic ring is substituted by
lower alkenyl,
amino,
carboxy,
carboxy lower alkylthio,
cyano lower alkylthio,
lower alkoxy carbonyl lower alkylthio,
sulfonyl lower alkylthio,
pyridyl-N-oxide
hydroxy
cycloalkyl having 3 to 8 carbon atoms,
phenylamino,
carboxy lower alkanoylamino,
pyridyl,
pyridyl lower alkyl,
lower alkanoylamino,
lower alkanoyl lower alkylamino,
carbamyl,
carbamyl lower alkyl,
morpholinyl carbonyl,
phenyl,
halophenyl,
lower alkoxyphenyl,
lower alkylphenyl,
hydroxyphenyl,
sulfamylphenyl,
lower alkyl, or
lower alkyl substituted by
carboxy,
sulfonyl,
sulfamyl,
phenyl,
halophenyl,
carbamyl,
lower alkyl carbamyl,
lower alkoxy carbonyl,
halogen,
amino,
lower alkanoylamino,
hydroxy,
cyano,
lower alkoxy,
carboxy lower alkoxy,
carbamyl lower alkoxy,
lower alkoxy carbamyl lower alkoxy, or
phenoxy,
or wherein said 5-membered heteroaromatic ring is substituted by
a further 5-membered ring containing at least one oxygen, sulfur, or nitrogen atom as a hetero atom or is such a further 5-membered ring substituted by
nitro,
carbamyl, or carboxy,
or wherein
R₅ is a 6-membered heteroaromatic ring wherein 1 to 4 ring members are nitrogen and the remaining ring members are carbon, such a 6-membered heteroaromatic ring fused to a benzene ring, such a 6-membered heteroaromatic ring fused to a further 5-membered or 6-membered heteroaromatic ring wherein 1 to 3 ring members are nitrogen and the remaining ring members are carbon, or such 6-membered heteroaromatic ring or 6-membered heteroaromatic ring fused to benzene or to a further heteroaromatic ring wherein said 6-membered heteroaromatic ring is substituted by
carboxy lower alkoxy,
carboxy lower alkylthio,
lower alkoxy carbonyl lower alkylthio,
hydroxy,
lower alkoxy,
lower alkoxy carbonyl lower alkoxy,
carboxy,
nitro,
halogen,
lower alkoxy carbonyl,
phenyl,
lower alkylthio,
amino,
morpholino,
morpholinyl carbonyl,
lower alkyl, or
lower alkyl substituted by
  carboxy,
  lower alkoxy carboxy,
  carbamyl, or
  cyano.

2. A compound as in claim 1 which is the 1-S-oxide of 7-[2-(2-aminothiazol-4-yl)-2-syn-methoxyimino-acetimido]-cephalosporanic acid.

3. A compound as in claim 1 wherein A is —CH₂Y and Y is a nucleophilic group selected from the group consisting of aliphatic carbonyloxy having 1 to 4 carbon atoms, hydroxy, and alkoxy having 1 to 8 carbon atoms.

4. A compound as in claim 1 wherein R₄ is hydrogen.

5. A compound as in claim 3 wherein R₄ is hydrogen.

6. A cephem compound as in claim 1 wherein X is SO in the S-configuration.

7. A cephem compound as in claim 1 wherein X is SO₂.

8. A pharmaceutical composition for the treatment of bacterial infections comprising an effective amount of a cephem compound as in claim 1 together with a pharmaceutically acceptable carrier.

9. The method of treating a bacterial infection in a patient suffering therefrom which comprises orally or parenterally administering to said patient an effective amount of a cephem compound as in claim 1.

* * * * *